US009725694B2

(12) United States Patent
Edinger et al.

(10) Patent No.: US 9,725,694 B2
(45) Date of Patent: *Aug. 8, 2017

(54) COMPOSITION FOR COLLECTING AND PRESERVING PLACENTAL STEM CELLS AND METHODS OF USING THE COMPOSITION

(75) Inventors: James W. Edinger, Belford, NJ (US); Mohammad Heidaran, Chatham, NJ (US); Wolfgang Hofgartner, White Plains, NY (US)

(73) Assignee: Anthrogenesis Corporation, Warren, NJ (US)

( * ) Notice: Subject to any disclaimer, the term of this patent is extended or adjusted under 35 U.S.C. 154(b) by 667 days.

This patent is subject to a terminal disclaimer.

(21) Appl. No.: 12/846,765

(22) Filed: Jul. 29, 2010

(65) Prior Publication Data
US 2010/0291679 A1    Nov. 18, 2010

Related U.S. Application Data

(63) Continuation of application No. 11/648,812, filed on Dec. 28, 2006, now Pat. No. 9,598,669.

(60) Provisional application No. 60/754,969, filed on Dec. 29, 2005.

(51) Int. Cl.
C12N 5/00          (2006.01)
C12N 5/073         (2010.01)

(52) U.S. Cl.
CPC ........ C12N 5/0605 (2013.01); C12N 2501/48 (2013.01); C12N 2501/999 (2013.01)

(58) Field of Classification Search
None
See application file for complete search history.

(56) References Cited

U.S. PATENT DOCUMENTS

| | | |
|---|---|---|
| 4,798,824 A | 1/1989 | Belzer et al. |
| 5,197,985 A | 3/1993 | Caplan et al. |
| 5,486,359 A | 1/1996 | Caplan et al. |
| 5,552,267 A | 9/1996 | Stern et al. |
| 5,635,517 A | 6/1997 | Muller et al. |
| 5,698,579 A | 12/1997 | Muller |
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 5,985,539 A * | 11/1999 | Takezawa ............... A01N 1/02 435/1.1 |
| 6,281,230 B1 | 8/2001 | Muller et al. |
| 6,288,089 B1 | 9/2001 | Zawada et al. |
| 6,307,056 B1 | 10/2001 | Corbett et al. |
| 6,316,471 B1 | 11/2001 | Muller et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,458,810 B1 | 10/2002 | Muller et al. |
| 6,476,052 B1 | 11/2002 | Muller et al. |
| 6,555,554 B2 | 4/2003 | Muller et al. |
| 6,897,231 B2 | 5/2005 | Bhagwat et al. |
| 6,987,184 B2 | 1/2006 | Sakata et al. |
| 7,045,148 B2 | 5/2006 | Hariri |
| 7,119,114 B1 | 10/2006 | Bennett et al. |
| 7,122,544 B2 | 10/2006 | Kois et al. |
| 7,129,242 B2 | 10/2006 | Satoh et al. |
| 7,147,626 B2 | 12/2006 | Goodman et al. |
| 7,208,513 B2 | 4/2007 | Bhagwat et al. |
| 7,211,594 B2 | 5/2007 | Bhagwat et |
| 7,220,771 B2 | 5/2007 | Bhagwat et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,354,947 B2 | 4/2008 | Sakata et al. |
| 7,429,599 B2 | 9/2008 | Satoh et al. |
| 7,442,699 B2 | 10/2008 | Kois et al. |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |

(Continued)

FOREIGN PATENT DOCUMENTS

| | | |
|---|---|---|
| EP | 1110957 | 6/2001 |
| WO | WO 98/03502 | 1/1998 |

(Continued)

OTHER PUBLICATIONS

Stroh C et al. 2002. The role of caspases in cryoinjury: caspase inhibition strongly improves the recovery of cryopreserved hematopoietic and other cells. FASEB J 16: 1651-1653.*
Warny M et al. 1999. Monocytic cell necrosis is mediated by potassium depletion and caspase-like proteases. Am J Physiol Cell Physiol 276: C717-C724.*
Karkkainen Stem Cells (2014) 32: 1904-1916.*
Lee et al. (J. Cell. Physiol. (2004) 198: 91-99.*
U.S. Appl. No. 09/659,904, filed Sep. 12, 2000, Hariri.
U.S. Appl. No. 12/187,337, filed Aug. 6, 2008, Heidaran et al.
U.S. Appl. No. 12/687,851, filed Jan. 14, 2010, Paludan et al.
Beltrami, et al., "Adult Cardiac Stem Cells Are Multipotent and Support Myocardial Regenerationl," 114:763-776 (2003).

(Continued)

Primary Examiner — Susan Hanley
(74) Attorney, Agent, or Firm — Jones Day

(57) ABSTRACT

The present invention provides improved compositions and methods for the collection of stem cells from an organ, e.g., placenta. The invention provides a stem cell collection composition comprising an apoptosis inhibitor and, optionally, an enzyme such as a protease or mucolytic enzyme, vasodilator, necrosis inhibitor, oxygen-carrying perfluorocarbon, or an organ preserving compound. The invention provides methods of using the stem cell collection composition to collect stem cells and to preserve populations of stem cells.

18 Claims, 7 Drawing Sheets

(56) References Cited

U.S. PATENT DOCUMENTS

Figure 1:
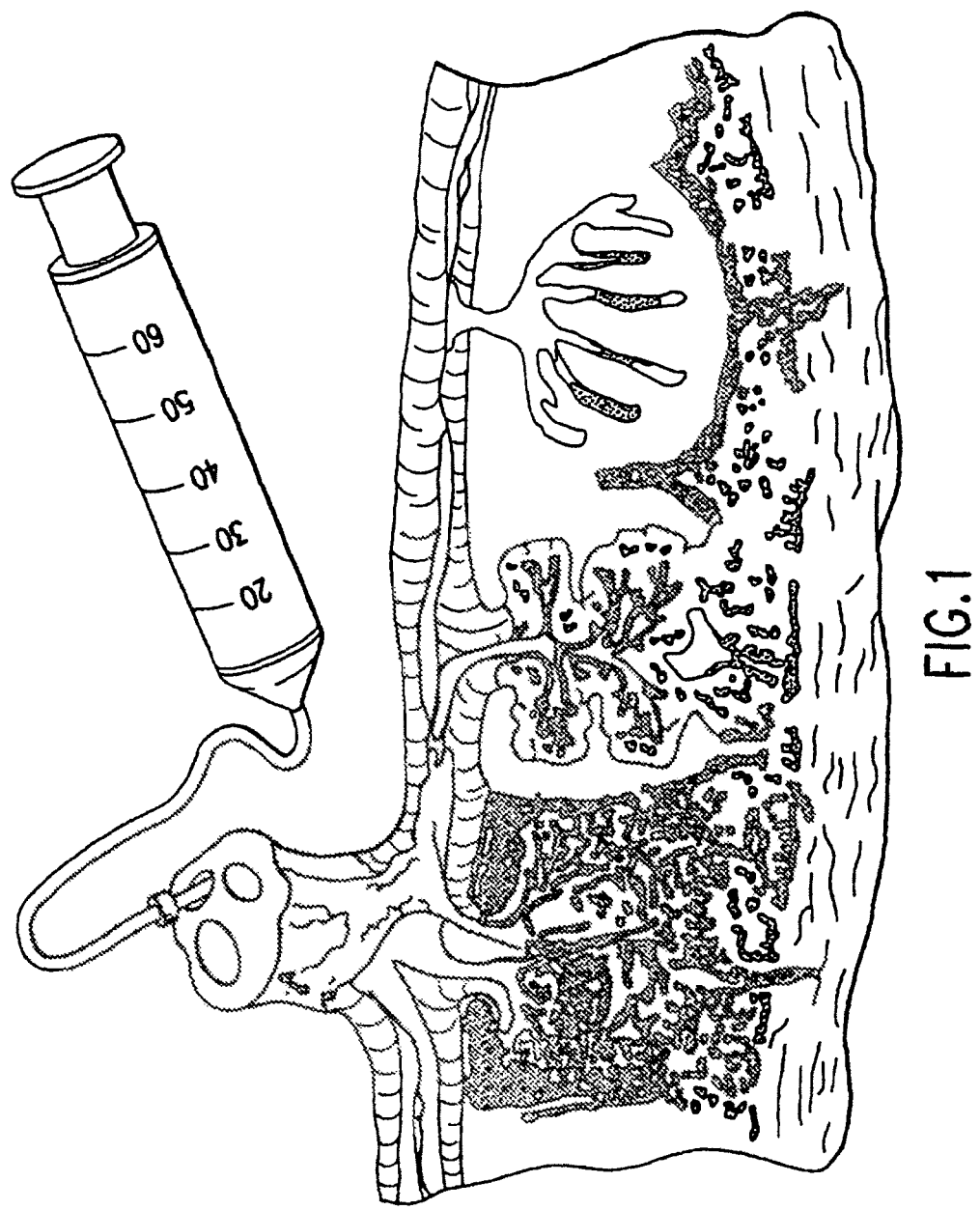
Figure 2A:
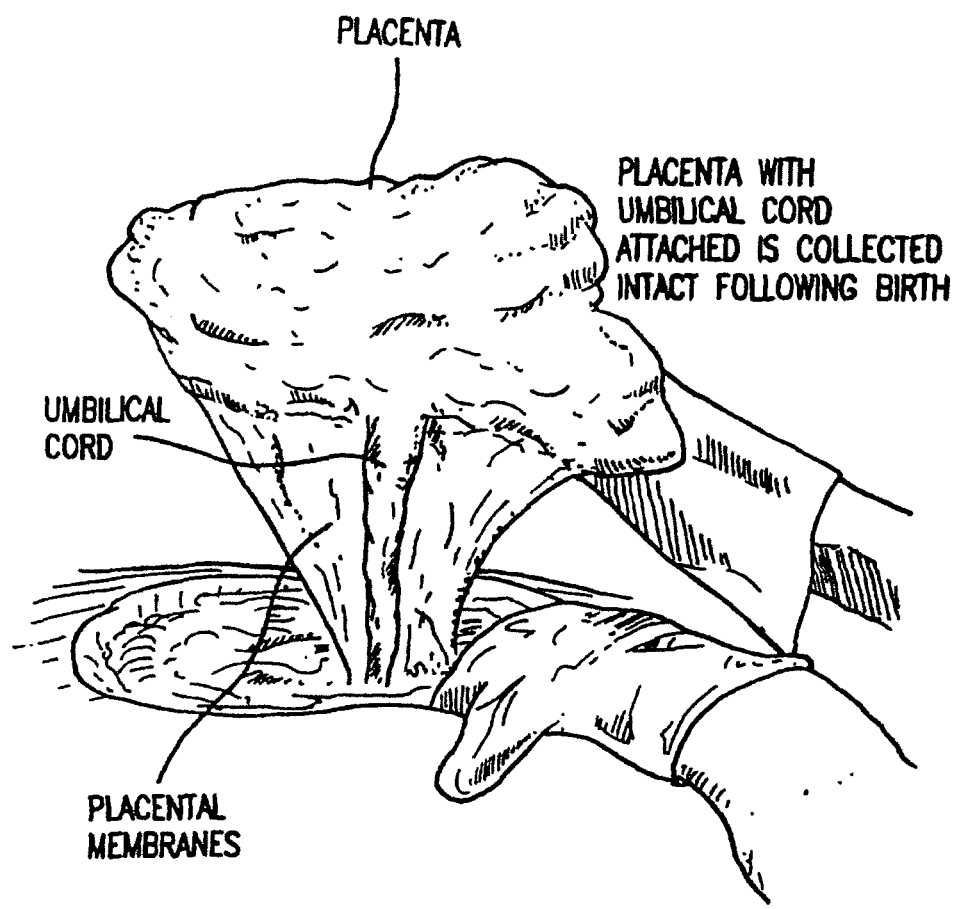
Figure 2B:
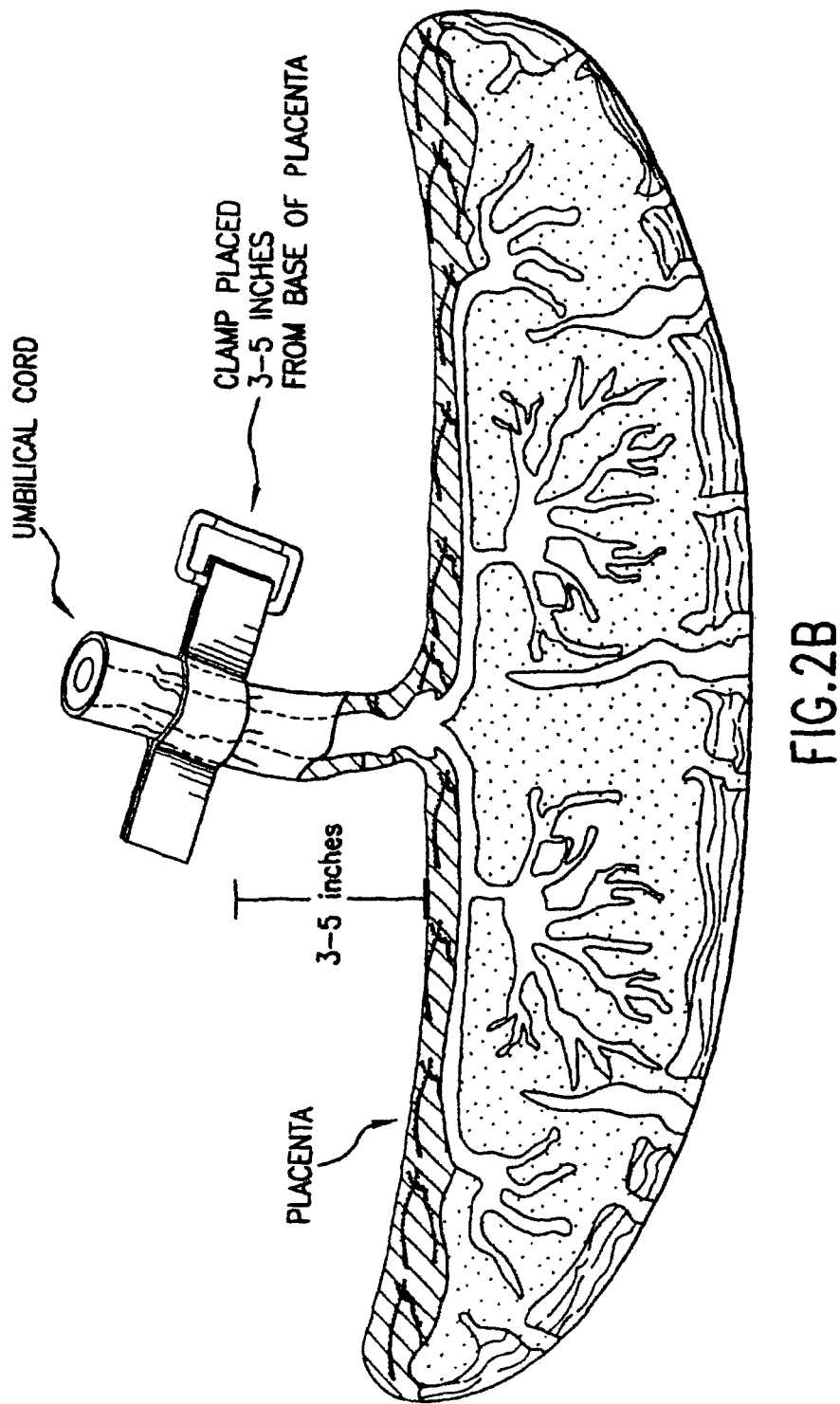
Figure 2D:
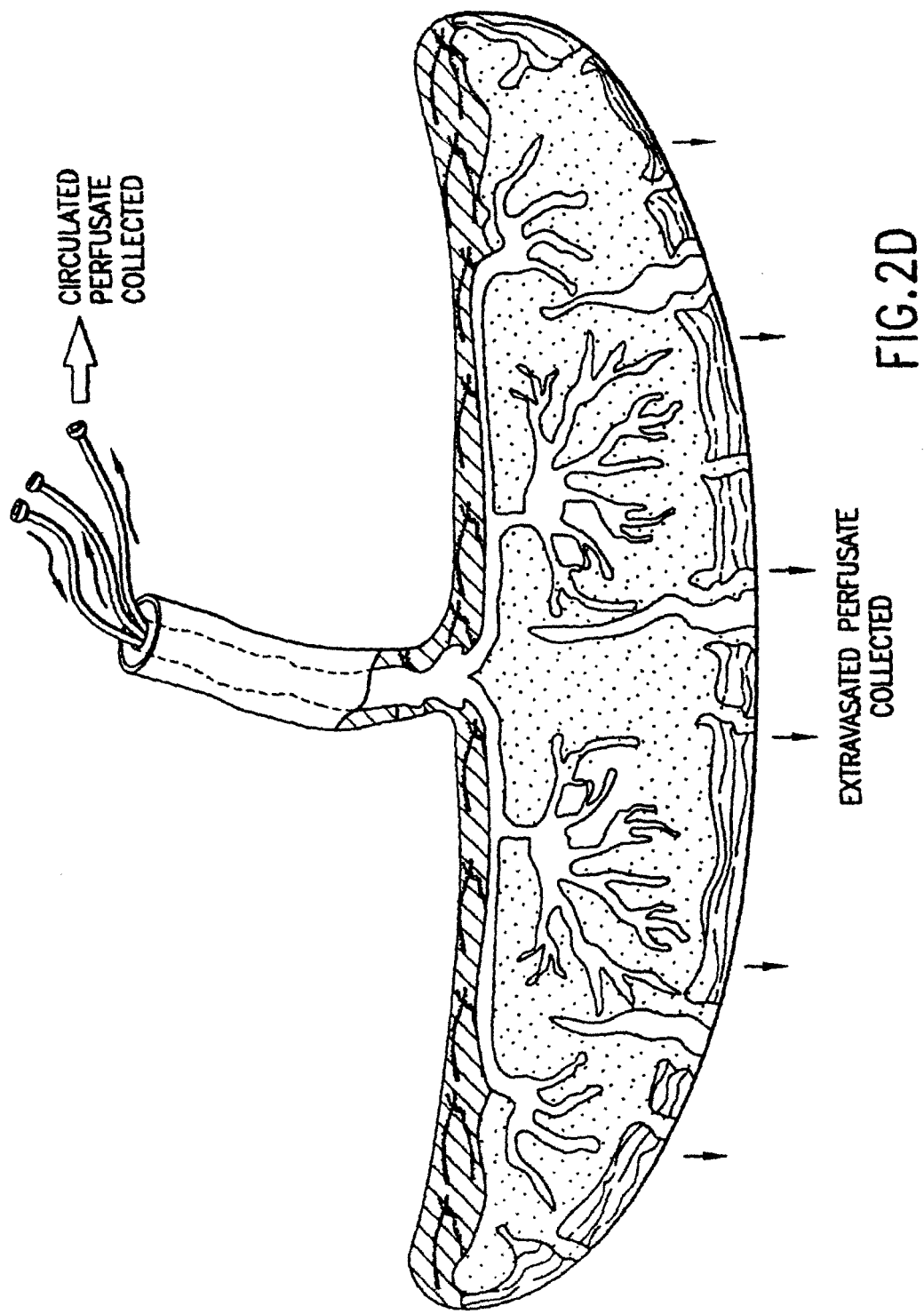

| | | |
|---|---|---|
| 2002/0045643 A1 | 4/2002 | Muller et al. |
| 2002/0061300 A1 | 5/2002 | Gokcen |
| 2002/0123141 A1 | 9/2002 | Hariri |
| 2002/0160510 A1 | 10/2002 | Hariri |
| 2003/0032179 A1 | 2/2003 | Hariri |
| 2003/0045552 A1 | 3/2003 | Robarge et al. |
| 2003/0096841 A1 | 5/2003 | Robarge et al. |
| 2003/0180269 A1 | 9/2003 | Hariri |
| 2003/0235909 A1 | 12/2003 | Hariri |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0072888 A1 | 4/2004 | Bennett et al. |
| 2004/0092562 A1 | 5/2004 | Sakata et al. |
| 2004/0097454 A1 | 5/2004 | Reusch et al. |
| 2004/0171147 A1 | 9/2004 | Hariri |
| 2004/0176434 A1 | 9/2004 | Bennett et al. |
| 2004/0219136 A1 | 11/2004 | Hariri |
| 2004/0241144 A1 | 12/2004 | Kaps et al. |
| 2005/0009876 A1 | 1/2005 | Bhagwat et al. |
| 2005/0019908 A1 | 1/2005 | Hariri |
| 2005/0118715 A1 | 6/2005 | Hariri et al. |
| 2005/0143420 A1 | 6/2005 | Moutouh-de Parseval et al. |
| 2005/0148034 A1 | 7/2005 | Hariri et al. |
| 2005/0158311 A1 | 7/2005 | Lu et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2006/0004043 A1 | 1/2006 | Bhagwat et al. |
| 2006/0060494 A1 | 3/2006 | Goodman et al. |
| 2006/0122179 A1 | 6/2006 | Zeldis et al. |
| 2006/0205771 A1 | 9/2006 | Noble et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0043328 A1 | 2/2007 | Goodman et al. |
| 2007/0053888 A1 | 3/2007 | Hariri |
| 2007/0060616 A1 | 3/2007 | Bennett et al. |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0099178 A1 | 4/2009 | Bhagwat et al. |
| 2009/0104164 A1 | 4/2009 | Zhang et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0143312 A1 | 6/2010 | Hariri |

FOREIGN PATENT DOCUMENTS

| | | | |
|---|---|---|---|
| WO | WO 98/54170 | 12/1998 | |
| WO | WO 00/12468 | 3/2000 | |
| WO | WO 00/35921 | 6/2000 | |
| WO | WO 00/39101 | 7/2000 | |
| WO | WO 00/56738 | 9/2000 | |
| WO | WO 00/64872 | 11/2000 | |
| WO | WO 00/73421 | * 12/2000 | ............ C12N 5/00 |
| WO | WO 00/75118 | 12/2000 | |
| WO | WO 01/12609 | 2/2001 | |
| WO | WO 01/12621 | 2/2001 | |
| WO | WO 01/14375 | 3/2001 | |
| WO | WO 01/23378 | 4/2001 | |
| WO | WO 01/27089 | 4/2001 | |
| WO | WO 01/56993 | 8/2001 | |
| WO | WO 01/58448 | 8/2001 | |
| WO | WO 01/91749 | 12/2001 | |
| WO | WO 02/10137 | 2/2002 | |
| WO | WO 02/16359 | 2/2002 | |
| WO | WO 02/46170 | 6/2002 | |
| WO | WO 02/059106 | 8/2002 | |
| WO | WO 02/064755 | 8/2002 | |
| WO | WO 02/066450 | 8/2002 | |
| WO | WO 03/086373 | * 10/2003 | ............ A61K 31/00 |
| WO | WO 03/102151 | 12/2003 | |
| WO | WO 2007/047468 | 4/2007 | |
| WO | WO 2008/051568 | 5/2008 | |
| WO | WO 2008/100497 | 8/2008 | |

OTHER PUBLICATIONS

Lindberg et al., "Apoptosis in Refractory Anaemia With Ringed Sideroblasts Is Initiated a the Stem Cell Level and Associated With Increased Activation of Caspases," British Journal of Haematology 112(3):714-726 (2001).

Notice of Opposition by Farmindustria S.A. to corresponding claims filed in Peru; English translation Jan. 18, 2008.

Pellegrini, et al., "FADD and Caspase-8 Are Required for Cytokine-Induced Proliferation of Hemopoietic Progenitor Cells," Blood 106(5):1581-1589 (2005).

Rudel, "Caspase Inhibitors in Prevention of Apoptosis," Herz 24:236-41 (1999).

Shi et al., "BAX and Caspase Activity Limit Adult Neural Stem Cell Persistence," Society for Neuroscience Abstract Viewer and Itinerary Planner, vol. 2003, Abstract No. 356-7, & 33rd Annual Meeting of the Society of Neuroscience; New Orleans, LA, USANov. 8-12, 2003.

Wiesmann, et al., "Effects of Caspase Inhibitors on Hematopoietic Engraftment After Short-Term Culture," Cell. Transplant. 11(4):351-358 (2002).

Wiesmann, et al., "No Reduction of TGF-Beta Induced Apoptosis on Hematopoietic Stem and Progenitor Cells in Vitro by Caspase Inhibitors," Blood 98(11) Part 2, p. 141b (2001).

Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).

Notice of Allowance dated Sep. 15, 2005 in U.S. Appl. No. 10/004,942, now U.S. Pat. No. 7,045,148.

Office Action dated Dec. 5, 2003 in U.S. Appl. No. 10/004,942, now U.S. Pat. No. 7,045,148.

Office Action dated Jun. 15, 2004 in U.S. Appl. No. 10/004,942, now U.S. Pat. No. 7,045,148.

Office Action dated Jun. 20, 2005 in U.S. Appl. No. 10/004,942, now U.S. Pat. No. 7,045,148.

Office Action dated May 7, 2003 in U.S. Appl. No. 10/004,942, now U.S. Pat. No. 7,045,148.

Office Action dated Dec. 16, 2004 in U.S. Appl. No. 10/004,942, now U.S. Pat. No. 7,045,148.

Notice of Allowance May 21, 2007 in U.S. Appl. No. 10/640,428, now U.S. Pat. No. 7,255,879.

Office Action dated Jan. 19, 2006 in U.S. Appl. No. 10/640,428, now U.S. Pat. No. 7,255,879.

(56) References Cited

OTHER PUBLICATIONS

Office Action dated Oct. 18, 2006 in U.S. Appl. No. 10/640,428, now U.S. Pat. No. 7,255,879.
Office Action dated Apr. 20, 2007 in U.S. Appl. No. 11/187,400.
Office Action dated Jan. 4, 2008 in U.S. Appl. No. 11/187,400.
Non Final Rejection dated Feb. 22, 2010 in U.S. Appl. No. 11/648,812.

* cited by examiner

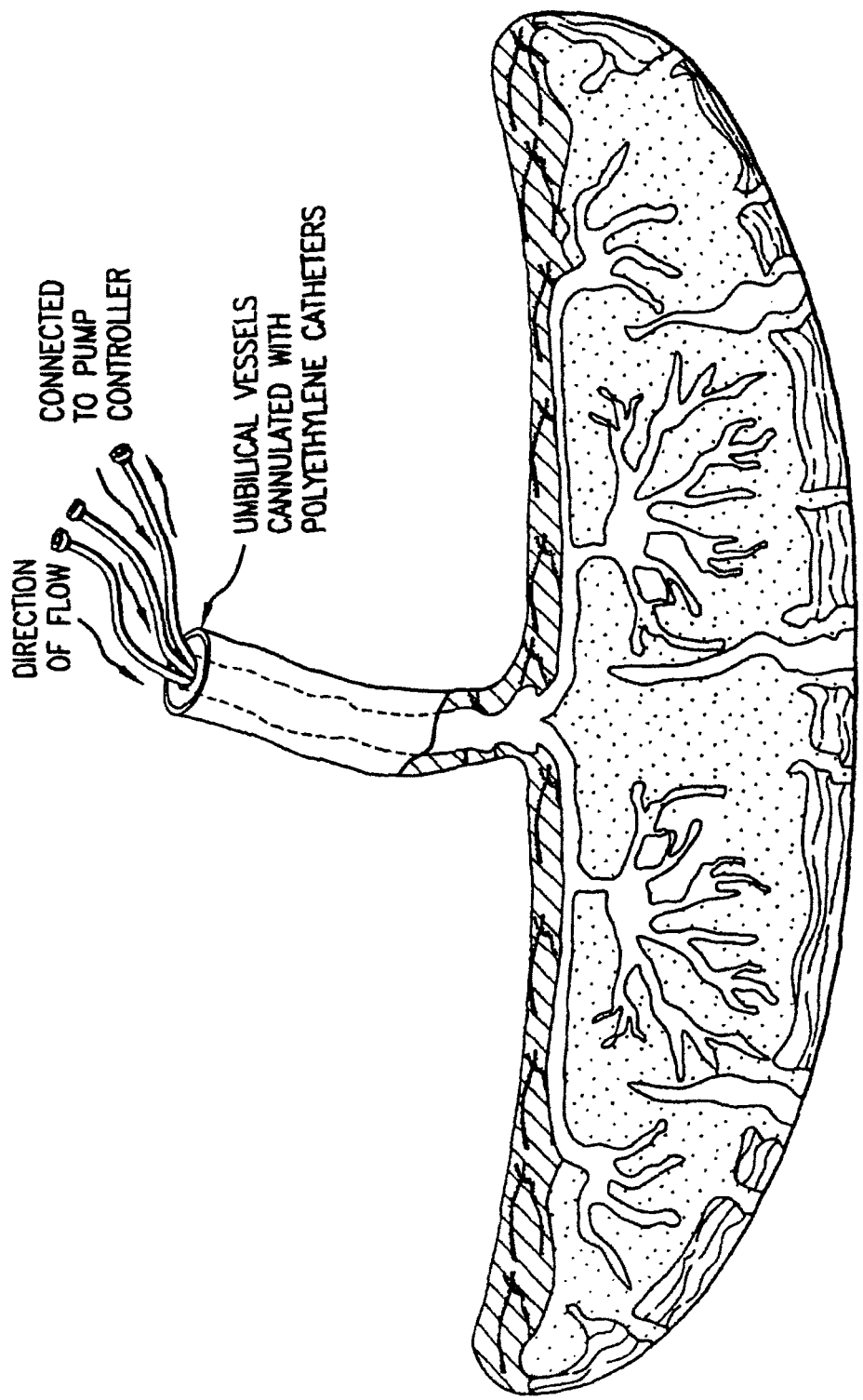

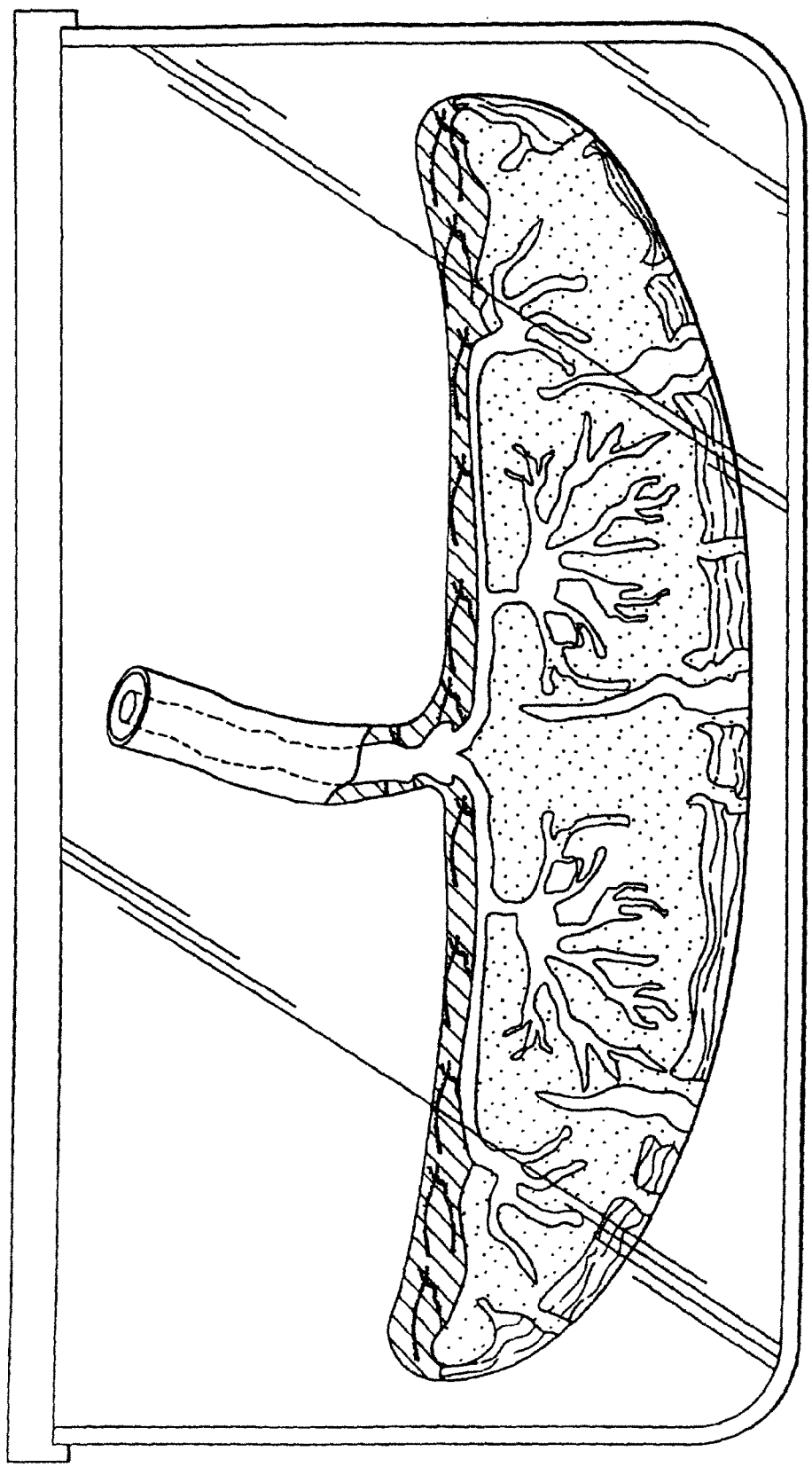

COMPOSITION FOR COLLECTING AND PRESERVING PLACENTAL STEM CELLS AND METHODS OF USING THE COMPOSITION

This application is a continuation of U.S. application Ser. No. 11/648,812, filed Dec. 28, 2006, now U.S. Pat. No. 9,598,669, which claims benefit of U.S. Provisional Application No. 60/754,969, filed Dec. 29, 2005, the entirety of each of which is incorporated herein by reference.

1. INTRODUCTION

The present invention relates to improved methods and compositions for the collection of placental stem cells, e.g., by perfusion or physical and/or enzymatic disruption of a placenta or a part thereof, and methods of collecting the stem cells using the compositions. The compositions disclosed herein comprise a physiologically-acceptable aqueous solution, e.g., a saline solution, one or more proteases and one or more inhibitors of JNK (c-Jun-N-terminal Kinase). Optionally, the composition further comprises a compound that modulates (e.g., inhibits) TNF-α, an immunomodulatory compound, a vasodilator, necrosis inhibitor, oxygen-carrying perfluorocarbon, or a combination of any of the foregoing. The present invention provides methods of using the composition to collect and preserve stem cells and populations of stem cells.

2. BACKGROUND OF THE INVENTION

Human stem cells are totipotential or pluripotential precursor cells capable of generating a variety of mature human cell lineages. Evidence exists that demonstrates that stem cells can be employed to repopulate many, if not all, tissues and restore physiologic and anatomic functionality.

Many different types of mammalian stem cells have been characterized. See, e.g., Caplan et al., U.S. Pat. No. 5,486,359 (human mesenchymal stem cells); Hu et al., WO 00/73421 (methods of isolation, cryopreservation, and therapeutic use of human amniotic epithelial cells); Beltrami et al., *Cell* 114(6):763-766 (2003) (cardiac stem cells); Forbes et al., *J. Pathol.* 197(4):510-518 (2002) (hepatic stem cells). Umbilical cord blood, and total nucleated cells derived from cord blood, have been used in transplants to restore, partially or fully, hematopoietic function in patients who have undergone ablative therapy.

The placenta is a particularly attractive source of stem cells. See, e.g., Hariri, U.S. Patent Application Publication Nos. 2002/0123141 and 2003/0032179. While placentas are readily available, it is desirable to maximize the number of stem cells obtained from each placenta. Stem cells, like other types of cells, are sensitive to environmental changes brought about during collection and storage. These changes can bring about apoptosis or necrosis of the stem cells. There is thus a need for improved compositions and for the collection of placental stem cells from a post-partum mammalian placenta so as to recover increased numbers of stem cells from a single placenta.

3. SUMMARY OF THE INVENTION

The present invention provides improved methods and compositions for the perfusion and preservation of organs, e.g., placenta, to facilitate the recovery of stem cells, as well as methods of collecting stem cells using the compositions.

In one embodiment, the invention provides a method of isolating a stem cell, comprising contacting said stem cell with a solution comprising an inhibitor of apoptosis, and isolating said stem cell. In another embodiment, the invention provides a method of isolating a stem cell, comprising contacting the stem cell with a solution comprising a necrosis inhibitor, and isolating said stem cell.

In a specific embodiment of either of the above embodiments, said inhibitor of apoptosis is a caspase inhibitor. In another specific embodiment, said inhibitor of apoptosis is a c-Jun N-terminal kinase (JNK) inhibitor. In a more specific embodiment, said JNK inhibitor does not modulate the differentiation or proliferation of said stem cell prior to said isolation. In another specific embodiment, the method additionally comprises contacting said stem cell with a compound that inhibits necrosis. In another specific embodiment, said stem cell is isolated from mammalian placenta, umbilical cord, placental blood or umbilical cord blood. In another specific embodiment, the method additionally comprises contacting said stem cell with an oxygen-carrying perfluorocarbon. In another specific embodiment, the method additionally comprises contacting said stem cell with a protease. In a more specific embodiment, said protease is a matrix metalloprotease or a neutral protease. In a more specific embodiment, said matrix metalloprotease is collagenase. In another specific embodiment, said neutral protease is thermolysin or dispase. In another specific embodiment, the method additionally comprises contacting said stem cell with a mucolytic enzyme. In a more specific embodiment, said mucolytic enzyme is hyaluronidase. In another specific embodiment, of the method, said solution is a saline solution or culture medium. In another specific embodiment, said solution additionally comprises hydroxyethyl starch, lactobionic anion and raffinose. In another specific embodiment, said solution comprises UW solution.

In another specific embodiment, said stem cell is isolated from a tissue by physical disruption, including enzymatic digestion, of said tissue. In a more specific embodiment, said stem cell is isolated from the placenta by enzymatic digestion of at least a part of the placenta.

In another specific embodiment, said mammalian placenta is exsanguinated prior to said physical disruption. In another specific embodiment, said stem cell is isolated from said mammalian placenta, and said isolating is performed by perfusing said mammalian placenta with a perfusion solution. In a more specific embodiment, said perfusion is performed by perfusing the mammalian placenta with said perfusion solution in an amount and for a time sufficient to collect a detectable number of stem cells from said mammalian placenta. In more specific embodiment, said mammalian placenta is exsanguinated prior to said perfusing. In more specific embodiment, said perfusing is performed by passing said perfusion solution into one or both of the umbilical artery and umbilical vein of said placenta. In another more specific embodiment, said perfusion solution comprises 0.9% NaCl solution or phosphate buffered saline. In another more specific embodiment, said perfusing uses from about 500 mL to about 2000 mL of said perfusion solution, or about 750 mL of said perfusion solution. In another more specific embodiment, said perfusing is performed a plurality of times.

In another specific embodiment, said stem cell is exposed to a hypoxic condition for less than 72 hours following delivery, wherein a hypoxic condition is a concentration of oxygen that is less than normal blood oxygen concentration. In a more specific embodiment, said stem cell is exposed to said hypoxic condition for less than 48 hours. In another more specific embodiment, said stem cell is exposed to said hypoxic condition for less than 24 hours. In another more specific embodiment, said stem cell is exposed to said hypoxic condition for less than six hours. In another more specific embodiment, said stem cell is not exposed to a hypoxic condition.

In another specific embodiment, said stem cell is not exposed to shear stress during said isolation.

In another specific embodiment, said JNK inhibitor is an indazole. In another specific embodiment, said JNK inhibitor has the structure

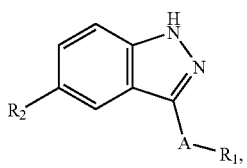

(I)

wherein:

A is a direct bond, —$(CH_2)_a$—, —$(CH_2)_b$CH=CH$(CH_2)_c$—, or —$(CH_2)_b$C≡C$(CH_2)_c$—;

$R_1$ is aryl, heteroaryl or heterocycle fused to phenyl, each being optionally substituted with one to four substituents independently selected from $R_3$;

$R_2$ is —$R_3$, —$R_4$, —$(CH_2)_b$C(=O)$R_5$, —$(CH_2)_b$C(=O)OR$_5$, —$(CH_2)_b$C(=O)NR$_5$R$_6$,
—$(CH_2)_b$C(=O)NR$_5$(CH$_2)_c$C(=O)R$_6$, —$(CH_2)_b$NR$_5$C(=O)R$_6$,
—$(CH_2)_b$NR$_5$C(=O)NR$_6$R$_7$, —$(CH_2)_b$NR$_5$R$_6$, —$(CH_2)_b$OR$_5$,
—$(CH_2)_b$SO$_d$R$_5$ or —$(CH_2)_b$SO$_2$NR$_5$R$_6$;

a is 1, 2, 3, 4, 5 or 6;

b and c are the same or different and at each occurrence independently selected from 0, 1, 2, 3 or 4;

d is at each occurrence 0, 1 or 2;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —C(=O)OR$_8$, —OC(=O)R$_8$, —C(=O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2)_b$OR$_9$, —NR$_8$C(=O)(CH$_2)_b$R$_9$, —O(CH$_2)_b$NR$_8$R$_9$, or heterocycle fused to phenyl;

$R_4$ is alkyl, aryl, arylalkyl, heterocycle or heterocycloalkyl, each being optionally substituted with one to four substituents independently selected from $R_3$, or $R_4$ is halogen or hydroxy;

$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

In another specific embodiment, said JNK inhibitor has the structure

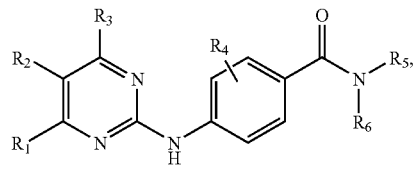

(II)

wherein:

$R_1$ is aryl or heteroaryl optionally substituted with one to four substituents independently selected from $R_7$;

$R_2$ is hydrogen;

$R_3$ is hydrogen or lower alkyl;

$R_4$ represents one to four optional substituents, wherein each substituent is the same or different and independently selected from halogen, hydroxy, lower alkyl and lower alkoxy;

$R_5$ and $R_6$ are the same or different and independently —$R_8$, —$(CH_2)_a$C(=O)R$_9$, —$(CH_2)_a$C(=O)OR$_9$, —$(CH_2)_a$C(=O)NR$_9$R$_{10}$, —$(CH_2)_a$C(=O)NR$_9$(CH$_2)_b$C(=O)R$_{10}$, —$(CH_2)_a$NR$_9$C(=O)R$_{10}$, $(CH_2)_a$NR$_{11}$C(=O)NR$_9$R$_{10}$, —$(CH_2)_a$NR$_9$R$_{10}$, —$(CH_2)_a$OR$_9$, —$(CH_2)_a$SO$_c$R$_9$ or —$(CH_2)_a$SO$_2$NR$_9$R$_{10}$;

or $R_5$ and $R_6$ taken together with the nitrogen atom to which they are attached to form a heterocycle or substituted heterocycle;

$R_7$ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, —C(=O)OR$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2)_b$OR$_9$, —NR$_8$C(=O)(CH$_2)_b$R$_9$, —O(CH$_2)_b$NR$_8$R$_9$, or heterocycle fused to phenyl;

$R_8$, $R_9$, $R_{10}$ and $R_{11}$ are the same or different and at each occurrence independently hydrogen, alkyl, aryl, arylalkyl, heterocycle, heterocycloalkyl;

or $R_8$ and $R_9$ taken together with the atom or atoms to which they are attached to form a heterocycle;

a and b are the same or different and at each occurrence independently selected from 0, 1, 2, 3 or 4; and c is at each occurrence 0, 1 or 2.

In another specific embodiment, said JNK inhibitor has the structure

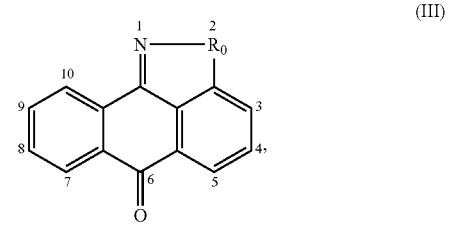

(III)

wherein $R_0$ is —O—, —S—, —S(O)—, —S(O)$_2$—, NH or —CH$_2$—;

the compound of structure (III) being: (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

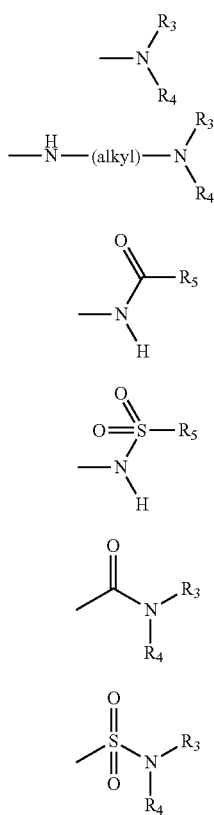

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

In a more specific embodiment, the method additionally comprises contacting the stem cell with an immunomodulatory compound. In a more specific embodiment, said immunomodulatory compound is 3-(4-amino-1-oxo-1,3-dihydroisoindol-2-yl)-piperidine-2,6-dione; 3-(4'aminoisolindoline-1'-onw)-1-piperidine-2,6-dione; 4-(Amino)-2-(2,6-dioxo(3-piperidyl))-isoindoline-1,3-dione; or α-(3-aminophthalimido) glutarimide. In another more specific embodiment, said immunomodulatory compound is a compound having the structure

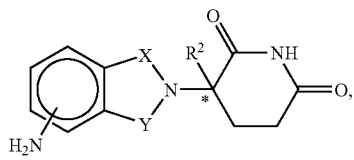

wherein one of X and Y is C=O, the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

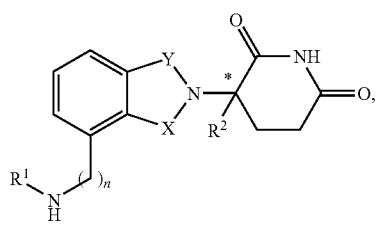

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^3$, $C(S)NR^3R^3$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O-R^5$ or the $R^6$ groups can join to form a heterocycloalkyl group;

n is 0 or 1; and

* represents a chiral-carbon center;

or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

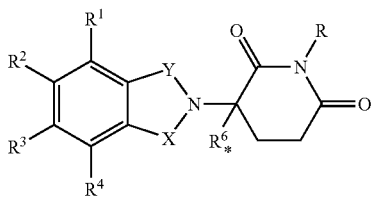

wherein:
one of X and Y is C═O and the other is CH$_2$ or C═O;
R is H or CH$_2$OCOR';
(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, or R$^4$ is nitro or —NHR$^5$ and the remaining of R$^1$, R$^2$, R$^3$, or R$^4$ are hydrogen;
R$^5$ is hydrogen or alkyl of 1 to 8 carbons
R$^6$ hydrogen, alkyl of 1 to 8 carbon atoms, benzo, chloro, or fluoro;
R' is R$^7$—CHR$^{10}$—N(R$^8$R$^9$);
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$_1$CH$_2$CH$_2$— in which X$_1$ is —O—, —S—, or —NH—;
R$^{10}$ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof.

In another specific embodiment of the method, said solution additionally comprises a vasodilator. In a more specific embodiment, said vasodilator is an antihypertensive drug. In another more specific embodiment, said vasodilator activates guanylyl cyclase, ADP-ribosyl transferase or cyclooxygenase, or inhibits lipoxygenase. In another more specific embodiment, said vasodilator is atrial natriuretic peptide (ANP), adrenocorticotropin, corticotropin-releasing hormone, sodium nitroprusside, hydralazine, adenosine triphosphate, adenosine, indomethacin or magnesium sulfate. In a more specific embodiment, said hydralazine is present in a concentration of from about 0.1 mM to about 10 mM. In another more specific embodiment, said adenosine is present at a concentration of about 0.001 mM to about 10.0 mM. In another more specific embodiment, said adenosine triphosphate is present at a concentration of about 0.1 mM to about 1000 mM. In another more specific embodiment, said indomethacin is present at a concentration of about 1 mg/kg to about 20 mg/kg, wherein "kg" is the weight of the placenta. In another more specific embodiment, said magnesium sulfate is present at a concentration of about 0.1 mM to about 20 mM.

In another specific embodiment of the method, said stem cell is a CD34$^+$ stem cell. In a more specific embodiment, CD34$^+$ stem cell is a CD34$^+$CD38$^-$ stem cell. In an more specific embodiment, said CD34$^+$CD38$^-$ stem cell is part of a population of CD34$^+$CD38$^-$ stem cells present in placental perfusate as a higher percentage of total nucleated cells as compared to the percentage of CD34$^+$CD38$^-$ cells in cord blood. In another specific embodiment of the invention, said stem cell is a CD34$^-$ stem cell. In a more specific embodiment, said CD34$^-$ stem cell is additionally CD31$^+$, CD33$^+$, CD44$^-$, CD117$^+$, KDR$^+$, HLA-ABC$^{weak}$, or HLA-DR$^{weak}$. In another more specific embodiment, said CD34$^-$ stem cell is additionally ABC-p$^+$, SSEA3$^+$, and SSEA4$^+$.

The invention also provides compositions, e.g., solutions, that facilitate stem cell collection, for example, collection by perfusion, and/or by tissue disruption, e.g., enzymatic digestion. In one embodiment, the invention provides a composition comprising, in a physiologically-acceptable solution, an inhibitor of apoptosis and a protease, wherein said composition, when contacted with population of stem cells, reduces or prevents apoptosis in said population of stem cells as compared to a population of stem cells not contacted with the composition. In a specific embodiment, said composition is not a naturally-occurring composition. In another specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another specific embodiment, said protease is present in an amount sufficient to detectably dissociate the cells of a tissue from which said stem cells may be derived. In another embodiment, the composition additionally comprises an inhibitor of necrosis. In a more specific embodiment, said inhibitor of necrosis is 2-(1H-Indol-3-yl)-3-pentylamino-maleimide. In another specific embodiment, the composition additionally comprises an oxygen-carrying perfluorocarbon. In another specific embodiment, said physiologically-acceptable solution is a saline solution or culture medium. In a more specific embodiment, said saline solution is 0.9% NaCl solution or phosphate buffered saline. In another more specific embodiment, said protease is a matrix metalloprotease or a neutral protease. In a more specific embodiment, said matrix metalloprotease is collagenase. In another specific embodiment, said neutral protease is thermolysin or dispase. In another specific embodiment, the composition additionally comprises a mucolytic enzyme. In a more specific embodiment, said mucolytic enzyme is hyaluronidase.

In another specific embodiment, the composition additionally comprises hydroxyethyl starch, lactobionic acid and raffinose. In another specific embodiment, the composition additionally comprises UW solution.

In a specific embodiment of the composition, said JNK inhibitor is an indazole. In another specific embodiment, said JNK inhibitor has the structure

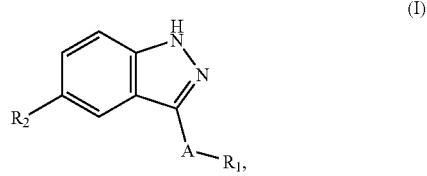

(I)

wherein:
A is a direct bond, —(CH$_2$)$_a$—, —(CH$_2$)$_b$CH═CH (CH$_2$)$_c$—, or —(CH$_2$)$_b$C≡C(CH$_2$)$_c$—;
R$_1$ is aryl, heteroaryl or heterocycle fused to phenyl, each being optionally substituted with one to four substituents independently selected from R$_3$;
R$_2$ is —R$_3$, —R$_4$, —(CH$_2$)$_b$C(═O)R$_5$, —(CH$_2$)$_b$C(═O) OR$_5$, —(CH$_2$)$_b$C(═O)NR$_5$R$_6$,
—(CH$_2$)$_b$C(═O)NR$_5$(CH$_2$)$_c$C(═O)R$_6$, —(CH$_2$)$_b$NR$_5$C (═O)R$_6$, —(CH$_2$)$_b$NR$_5$C(=O)NR$_6$R$_7$, —(CH$_2$)$_b$NR$_5$R$_6$, —(CH$_2$)$_b$OR$_5$, —(CH$_2$)$_b$SO$_d$R$_5$ or —(CH$_2$)$_b$SO$_2$NR$_5$R$_6$, a is 1, 2, 3, 4, 5 or 6;

b and c are the same or different and at each occurrence independently selected from 0, 1, 2, 3 or 4;

d is at each occurrence 0, 1 or 2;

R$_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —C(=O)OR$_8$, —OC(=O)R$_8$, —C(=O)NR$_8$R$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_4$ is alkyl, aryl, arylalkyl, heterocycle or heterocycloalkyl, each being optionally substituted with one to four substituents independently selected from R$_3$, or R$_4$ is halogen or hydroxy;

R$_5$, R$_6$ and R$_7$ are the same or different and at each occurrence independently hydrogen, alkyl, aryl, arylalkyl, heterocycle or heterocycloalkyl, wherein each of R$_5$, R$_6$ and R$_7$ are optionally substituted with one to four substituents independently selected from R$_3$; and R$_8$ and R$_9$ are the same or different and at each occurrence independently hydrogen, alkyl, aryl, arylalkyl, heterocycle, or heterocycloalkyl, or R$_8$ and R$_9$ taken together with the atom or atoms to which they are bonded form a heterocycle, wherein each of R$_8$, R$_9$, and R$_8$ and R$_9$ taken together to form a heterocycle are optionally substituted with one to four substituents independently selected from R$_3$;

or a pharmaceutically acceptable salt, hydrate, solvate, clathrate, enantiomer, diastereomer, racemate, or mixture of stereoisomers thereof In another specific embodiment of the composition, said JNK inhibitor has the structure

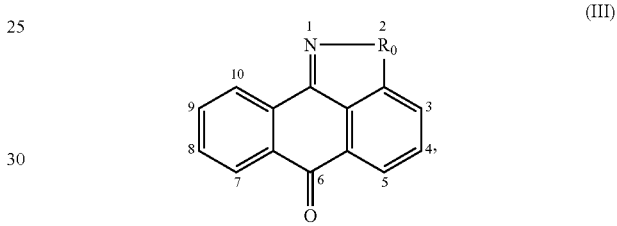

(II)

wherein:

R$_1$ is aryl or heteroaryl optionally substituted with one to four substituents independently selected from R$_7$;

R$_2$ is hydrogen;

R$_3$ is hydrogen or lower alkyl;

R$_4$ represents one to four optional substituents, wherein each substituent is the same or different and independently selected from halogen, hydroxy, lower alkyl and lower alkoxy;

R$_5$ and R$_6$ are the same or different and independently —R$_8$, —(CH$_2$)$_a$C(=O)R$_9$, —(CH$_2$)$_a$C(=O)OR$_9$, —(CH$_2$)$_a$C(=O)NR$_9$R$_{10}$, —(CH$_2$)$_a$C(=O)NR$_9$(CH$_2$)$_b$C(=O)R$_{10}$, —(CH$_2$)$_a$NR$_9$C(=O)R$_{10}$, (CH$_2$)$_a$NR$_{11}$C(=O)NR$_9$R$_{10}$, —(CH$_2$)$_a$NR$_9$R$_{10}$, —(CH$_2$)$_a$OR$_9$, —(CH$_2$)$_a$SO$_c$R$_9$ or —(CH$_2$)$_a$SO$_2$NR$_9$R$_{10}$;

or R$_5$ and R$_6$ taken together with the nitrogen atom to which they are attached to form a heterocycle or substituted heterocycle;

R$_7$ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, —C(=O)OR$_8$, —OC(=O)R$_8$, —C(=O)NR$_8$R$_9$, —C(=O)NR$_8$OR$_9$, —SO$_c$R$_8$, —SO$_c$NR$_8$R$_9$, —NR$_8$SO$_c$R$_9$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_8$, R$_9$, R$_{10}$ and R$_{11}$ are the same or different and at each occurrence independently hydrogen, alkyl, aryl, arylalkyl, heterocycle, heterocycloalkyl;

or R$_8$ and R$_9$ taken together with the atom or atoms to which they are attached to form a heterocycle;

a and b are the same or different and at each occurrence independently selected from 0, 1, 2, 3 or 4; and c is at each occurrence 0, 1 or 2;

or a pharmaceutically acceptable salt, hydrate, solvate, clathrate, enantiomer, diastereomer, racemate, or mixture of stereoisomers thereof.

In another specific embodiment of the composition, said JNK inhibitor has the structure

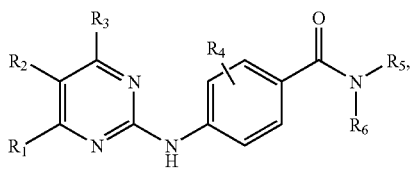

(III)

wherein R$_0$ is —O—, —S—, —S(O)—, —S(O)$_2$—, NH or —CH$_2$—;

the compound of structure (III) being: (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

(a)

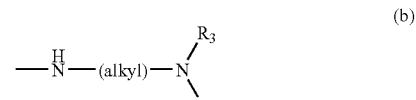

(b)

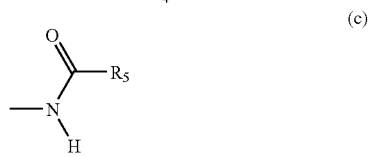

(c)

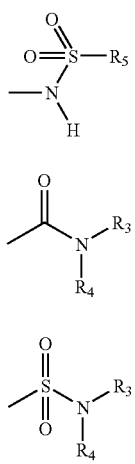

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl;

or a pharmaceutically acceptable salt, hydrate, solvate, clathrate, enantiomer, diastereomer, racemate, or mixture of stereoisomers thereof.

In a more specific embodiment, the composition additionally comprises an immunomodulatory compound. In another more specific embodiment, said immunomodulatory compound is 3-(4-amino-1-oxo-1,3-dihydroisoindol-2-yl)-piperidine-2,6-dione; 3-(4'aminoisolindoline-1'-onw)-1-piperidine-2,6-dione; 4-(Amino)-2-(2,6-dioxo(3-piperidyl))-isoindoline-1,3-dione; or α-(3-aminophthalimido) glutarimide. In another more specific embodiment, said immunomodulatory compound is a compound having the structure

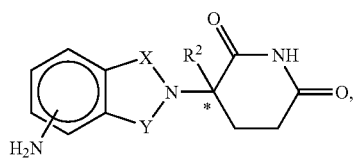

wherein one of X and Y is C=O, the other of X and Y is C=O or CH$_2$, and $R^2$ is hydrogen or lower alkyl, or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

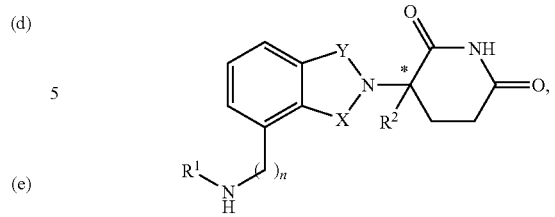

wherein one of X and Y is C=O and the other is CH$_2$ or C=O;

$R^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;

$R^2$ is H, F, benzyl, (C$_1$-C$_8$)alkyl, (C$_2$-C$_8$)alkenyl, or (C$_2$-C$_8$)alkynyl;

$R^3$ and $R^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;

$R^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

$R^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of $R^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;

n is 0 or 1; and

* represents a chiral-carbon center;

or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

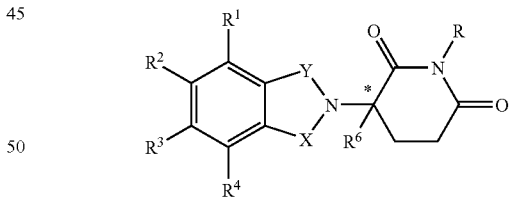

wherein:

one of X and Y is C=O and the other is CH$_2$ or C=O; R is H or CH$_2$OCOR';

(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, or R$^4$ is nitro or —NHR$^5$ and the remaining of R$^1$, R$^2$, R$^3$, or R$^4$ are hydrogen;

$R^5$ is hydrogen or alkyl of 1 to 8 carbons $R^6$ hydrogen, alkyl of 1 to 8 carbon atoms, benzo, chloro, or fluoro;

R' is R$^7$—CHR$^{10}$—N(R$^8$R$^9$);

$R^7$ is m-phenylene or p-phenylene or —(C$_n$H$_{2n}$)— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center;

or a pharmaceutically acceptable salt, hydrate, solvate, clathrate, enantiomer, diastereomer, racemate, or mixture of stereoisomers thereof.

In another specific embodiment, the composition additionally comprises a vasodilator. In a more specific embodiment, said vasodilator is an antihypertensive drug. In another more specific embodiment, said vasodilator activates guanylyl cyclase, ADP-ribosyl transferase or cyclooxygenase, or inhibits lipoxygenase. In another more specific embodiment, said vasodilator is atrial natriuretic peptide (ANP), adrenocorticotropin, corticotropin-releasing hormone, sodium nitroprusside, hydralazine, adenosine triphosphate, adenosine, indomethacin or magnesium sulfate. In an even more specific embodiment, said hydralazine is present in a concentration of from about 0.1 mM to about 10 mM. In another more specific embodiment, said adenosine is present at a concentration of about 0.001 mM to about 10.0 mM. In another more specific embodiment, said adenosine triphosphate is present at a concentration of about 0.1 mM to about 1000 mM. In another more specific embodiment, said indomethacin is present at a concentration of about 1 mg/kg to about 20 mg/kg, wherein "kg" is the weight of the placenta. In another more specific embodiment, said magnesium sulfate is present at a concentration of about 0.1 mM to about 20 mM.

In another aspect, the invention provides a method of preserving a population of stem cells, comprising contacting a population of stem cells with an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another more specific embodiment, said JNK inhibitor and said perfluorocarbon are contained within a single solution prior to said contacting. In another more specific embodiment, said JNK inhibitor is contained within a first solution, and said perfluorocarbon is contained within a second solution, prior to said contacting. In another specific embodiment, said solution, first solution, or second solution additionally comprises hydroxyethyl starch, lactobionic anion and raffinose. The method of claim 95, wherein said JNK inhibitor and said perfluorocarbon are between about 0° C. and about 25° C. at the time of said contacting. In another more specific embodiment, said JNK inhibitor and said perfluorocarbon are between about 2° C. and 10° C., or between about 2° C. and about 5° C., at the time of said contacting. In another more specific embodiment, said contacting is performed during transport of said population of stem cells. In another more specific embodiment, said contacting is performed during freezing and thawing of said population of stem cells.

In another specific embodiment, the method additionally comprises contacting said population of stem cells with an inhibitor of necrosis. In a more specific embodiment, said inhibitor of necrosis is 2-(1H-Indol-3-yl)-3-pentylamino-maleimide.

In another specific embodiment of the method, said population of stem cells is exposed to a hypoxic condition for less than 72 hours during said preservation, wherein a hypoxic condition is a concentration of oxygen that is less than normal blood oxygen concentration. In a more specific embodiment, said population of stem cells is exposed to said hypoxic condition for less than 48 hours during said preservation. In another more specific embodiment, said population of stem cells is exposed to said hypoxic condition for less than 24 hours, or less than 6 hours, or is not exposed to a hypoxic condition, during said preservation. In another specific embodiment, said population of stem cells is not exposed to shear stress during said preservation.

In another specific embodiment, any of the foregoing solutions comprises UW solution.

In another specific embodiment of the method, said population of stem cells is contained within, or isolated from, a placenta.

In a more specific embodiment of the method, said JNK inhibitor has the structure

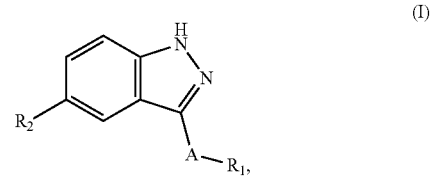

(I)

wherein:

A is a direct bond, —$(CH_2)_a$—, —$(CH_2)_b CH=CH(CH_2)_a$—, or —$(CH_2)_b C\equiv C(CH_2)_c$—;

$R_1$ is aryl, heteroaryl or heterocycle fused to phenyl, each being optionally substituted with one to four substituents independently selected from $R_3$;

$R_2$ is —$R_3$, —$R_4$, —$(CH_2)_b C(=O)R_5$, —$(CH_2)_b C(=O)OR_5$, —$(CH_2)_b C(=O)NR_5R_6$,
—$(CH_2)_b C(=O)NR_5(CH_2)_c C(=O)R_6$, —$(CH_2)_b NR_5 C(=O)R_6$,
—$(CH_2)_b NR_5 C(=O)NR_6R_7$, —$(CH_2)_b NR_5R_6$,
—$(CH_2)_b OR_5$,
—$(CH_2)_b SO_d R_5$ or —$(CH_2)_b SO_2 NR_5R_6$, a is 1, 2, 3, 4, 5 or 6;

b and c are the same or different and at each occurrence independently selected from 0, 1, 2, 3 or 4;

d is at each occurrence 0, 1 or 2;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —$C(=O)OR_8$, —$C(=O)NR_8R_9$, —$C(=O)NR_8OR_9$, —$SO_2NR_8R_9$, —$NR_8SO_2R_9$, —CN, —$NO_2$, —$NR_8R_9$, —$NR_8C(=O)R_9$, —$NR_8C(=O)(CH_2)_b OR_9$, —$NR_8C(=O)(CH_2)_b R_9$, —$O(CH_2)_b NR_8R_9$, or heterocycle fused to phenyl;

$R_4$ is alkyl, aryl, arylalkyl, heterocycle or heterocycloalkyl, each being optionally substituted with one to four substituents independently selected from $R_3$, or $R_4$ is halogen or hydroxy;

$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

In another more specific embodiment of the method, said JNK inhibitor has the structure

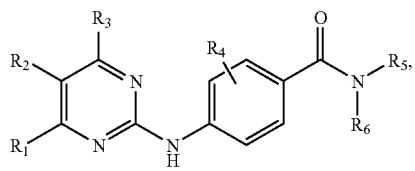
(II)

wherein:

$R_1$ is aryl or heteroaryl optionally substituted with one to four substituents independently selected from $R_7$;

$R_2$ is hydrogen;

$R_3$ is hydrogen or lower alkyl;

$R_4$ represents one to four optional substituents, wherein each substituent is the same or different and independently selected from halogen, hydroxy, lower alkyl and lower alkoxy;

$R_5$ and $R_6$ are the same or different and independently $-R_8$, $-(CH_2)_aC(=O)R_9$, $-(CH_2)_aC(=O)OR_9$, $-(CH_2)_aC(=O)NR_9R_{10}$, $-(CH_2)_aC(=O)NR_9(CH_2)_bC(=O)R_{10}$, $-(CH_2)_aNR_9C(=O)R_{10}$, $(CH_2)_aNR_{11}C(=O)NR_9R_{10}$, $-(CH_2)_aNR_9R_{10}$, $-(CH_2)_aOR_9$, $-(CH_2)_aSO_cR_9$ or $-(CH_2)_aSO_2NR_9R_{10}$;

or $R_5$ and $R_6$ taken together with the nitrogen atom to which they are attached to form a heterocycle or substituted heterocycle;

$R_7$ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, $-C(=O)OR_8$, $-OC(=O)R_8$, $-C(=O)NR_8R_9$, $-SO_cR_8$, $-SO_cNR_8R_9$, $-NR_8SO_cR_9$, $-NR_8R_9$, $-NR_8C(=O)R_9$, $-NR_8C(=O)(CH_2)_bOR_9$, $-NR_8C(=O)(CH_2)_bR_9$, $-O(CH_2)_bNR_8R_9$, or heterocycle fused to phenyl;

$R_8$, $R_9$, $R_{10}$ and $R_{11}$ are the same or different and at each occurrence independently hydrogen, alkyl, aryl, arylalkyl, heterocycle, heterocycloalkyl;

or $R_8$ and $R_9$ taken together with the atom or atoms to which they are attached to form a heterocycle;

a and b are the same or different and at each occurrence independently selected from 0, 1, 2, 3 or 4; and c is at each occurrence 0, 1 or 2.

In another more specific embodiment of the method, said JNK inhibitor has the structure

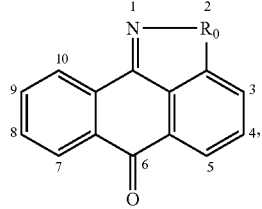
(III)

wherein $R_o$ is $-O-$, $-S-$, $-S(O)-$, $-S(O)_2-$, NH or $-CH_2-$;

the compound of structure (III) being: (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

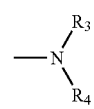
(a)

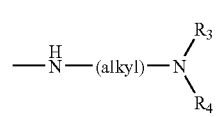
(b)

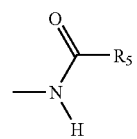
(c)

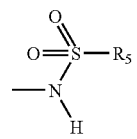
(d)

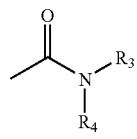
(e)

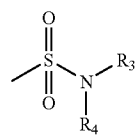
(f)

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

In an even more specific embodiment, the method additionally comprises contacting the stem cells with an immunomodulatory compound. In a more specific embodiment, said immunomodulatory compound is 3-(4-amino-1-oxo-1,3-dihydroisoindol-2-yl)-piperidine-2,6-dione; 3-(4'aminoisolindoline-1'-onw)-1-piperidine-2,6-dione; 4-(Amino)-2-(2,6-dioxo(3-piperidyl))-isoindoline-1,3-dione; or α-(3-aminophthalimido) glutarimide. In another more specific embodiment, said immunomodulatory compound is a compound having the structure

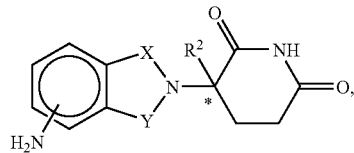

wherein one of X and Y is C=O, the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

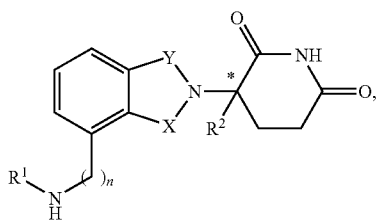

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, C(O)$R^3$, C(S)$R^3$, C(O)O$R^4$, $(C_1-C_8)$alkyl-N$(R^6)_2$, $(C_1-C_8)$alkyl-O$R^5$, $(C_1-C_8)$alkyl-C(O)O$R^5$, C(O)NH$R^3$, C(S)NH$R^3$, C(O)N$R^3R^{3'}$, C(S)N$R^3R^{3'}$ or $(C_1-C_8)$alkyl-O(CO)$R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-N$(R^6)_2$, $(C_1-C_8)$alkyl-O$R^5$, $(C_1-C_8)$alkyl-C(O)O$R^5$, $(C_1-C_8)$alkyl-O(CO)$R^5$, or C(O)O$R^5$;

$R^4$ is $(C_1-C_8)$alkyl, $(C_2-C_8)$alkenyl, $(C_2-C_8)$alkynyl, $(C_1-C_4)$alkyl-O$R^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group;

n is 0 or 1; and
* represents a chiral-carbon center;

or a pharmaceutically acceptable salt, hydrate, solvate, clathrate, enantiomer, diastereomer, racemate, or mixture of stereoisomers thereof. In another more specific embodiment, said immunomodulatory compound is a compound having the structure

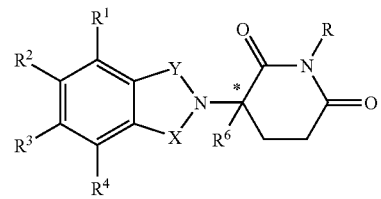

wherein:
one of X and Y is C=O and the other is $CH_2$ or C=O;
R is H or $CH_2OCOR'$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —NH$R^5$ and the remaining of $R^1$, $R^2$, $R^3$, or $R^4$ are hydrogen;
$R^5$ is hydrogen or alkyl of 1 to 8 carbons
$R^6$ hydrogen, alkyl of 1 to 8 carbon atoms, benzo, chloro, or fluoro;
R' is $R^7$—CHR$^{10}$—N(R$^8$R$^9$);
$R^7$ is m-phenylene or p-phenyle2ne or —$(C_nH_{2n})$— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;
$R^{10}$ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof.

In another specific embodiment of any of the above methods or compositions, said JNK inhibitor is present at a concentration of from about 0.5 μM to about 10 μM. In another specific embodiment of the above methods or compositions, said protease is present at a concentration of about 0.1 mg/mL to about 10 mg/mL. In another specific embodiment of the above methods or compositions, said mucolytic enzyme is present at a concentration of from about 0.1 mg/mL to about 10 mg/mL. In another specific embodiment of the above methods or compositions, said immunomodulatory compound is present at a concentration of from about 0.5 μM to about 10 μM. In another specific embodiment of the above methods or compositions, said vasodilator is atrial natriuretic peptide (ANP), adrenocorticotropin, corticotropin-releasing hormone, sodium nitroprusside, hydralazine, adenosine triphosphate, adenosine, indomethacin or magnesium sulfate. In an even more specific embodiment, said hydralazine is present in a concentration of from about 0.1 mM to about 10 mM. In another more specific embodiment, said adenosine is present at a concentration of about 0.001 mM to about 10.0 mM. In another more specific embodiment, said adenosine triphosphate is present at a concentration of about 0.1 mM to about 1000 mM.

In another specific embodiment, any of the compositions described herein can comprise a physiologically-acceptable solution comprising sodium chloride, potassium chloride, magnesium sulfate, calcium chloride, sodium sulfate, potassium sulfate, sodium carbonate, and glucose. Any of the composition can comprise one or more essential or non-essential amino acids, alone or in combination.

3.1 Definitions

As used herein, the term "embryonic stem cell" refers to a cell that is derived from the inner cell mass of a blastocyst (e.g., a 4- to 5-day-old human embryo) and that is pluripotent.

As used herein, the term "placental stem cell" refers to a stem cell or progenitor cell that is derived from a mammalian placenta, regardless of cellular morphology, cell surface markers, or the number of passages after a primary culture. The term does not, however, encompass stem cells derived solely from another tissue, e.g., placental blood or umbilical cord blood.

As used herein, the term "exsanguinated" or "exsanguination," when used with respect to the placenta, refers to the removal and/or draining of substantially all cord blood from the placenta.

As used herein, the term "perfusate" refers to the fluid collected following its passage through an organ or tissue. In a preferred embodiment, the perfusate contains one or more anticoagulants.

As used herein, the term "stem cell" encompasses pluripotent and multipotent cells, and progenitor cells, including committed progenitor cells. Multipotent and pluripotent stem cells retain the ability to proliferate and expand in culture.

"Alkyl" means a saturated straight chain or branched non-cyclic hydrocarbon having from 1 to 10 carbon atoms. "Lower alkyl" means alkyl, as defined above, having from 1 to 4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

An "alkenyl group" or "alkylidene" mean a straight chain or branched non-cyclic hydrocarbon having from 2 to 10 carbon atoms and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. An alkenyl group can be unsubstituted or substituted. A "cyclic alkylidene" is a ring having from 3 to 8 carbon atoms and including at least one carbon-carbon double bond, wherein the ring can have from 1 to 3 heteroatoms.

An "alkynyl group" means a straight chain or branched non-cyclic hydrocarbon having from 2 to 10 carbon atoms and including at lease one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. An alkynyl group can be unsubstituted or substituted.

The terms "Halogen" and "Halo" mean fluorine, chlorine, bromine or iodine.

"Haloalkyl" means an alkyl group, wherein alkyl is defined above, substituted with one or more halogen atoms.

"Keto" means a carbonyl group (i.e., C=O).

"Acyl" means an —C(O)alkyl group, wherein alkyl is defined above, including —C(O)CH$_3$, —C(O)CH$_2$CH$_3$, —C(O)(CH$_2$)$_2$CH$_3$, —C(O)(CH$_2$)$_3$CH$_3$, —C(O)(CH$_2$)$_4$CH$_3$, —C(O)(CH$_2$)$_5$CH$_3$, and the like.

"Acyloxy" means an —OC(O)alkyl group, wherein alkyl is defined above, including —OC(O)CH$_3$, —OC(O)CH$_2$CH$_3$, —OC(O)(CH$_2$)$_2$CH$_3$, —OC(O)(CH$_2$)$_3$CH$_3$, —OC(O)(CH$_2$)$_4$CH$_3$, —OC(O)(CH$_2$)$_5$CH$_3$, and the like.

"Ester" means and —C(O)Oalkyl group, wherein alkyl is defined above, including —C(O)OCH$_3$, —C(O)OCH$_2$CH$_3$, —C(O)O(CH$_2$)$_2$CH$_3$, —C(O)O(CH$_2$)$_3$CH$_3$, —C(O)O(CH$_2$)$_4$CH$_3$, —C(O)O(CH$_2$)$_5$CH$_3$, and the like.

"Alkoxy" means —O-(alkyl), wherein alkyl is defined above, including —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(CH$_2$)$_5$CH$_3$, and the like. "Lower alkoxy" means —O-(lower alkyl), wherein lower alkyl is as described above.

"Alkoxyalkoxy" means —O-(alkyl)-O-(alkyl), wherein each alkyl is independently an alkyl group defined above, including —OCH$_2$OCH$_3$, —OCH$_2$CH$_2$OCH$_3$, —OCH$_2$CH$_2$OCH$_2$CH$_3$, and the like.

"Alkoxycarbonyl" means —C(=O)O-(alkyl), wherein alkyl is defined above, including —C(=O)O—CH$_3$, —C(=O)O—CH$_2$CH$_3$, —C(=O)O—(CH$_2$)$_2$CH$_3$, —C(=O)O—(CH$_2$)$_3$CH$_3$, —C(=O)O—(CH$_2$)$_4$CH$_3$, —C(=O)O—(CH$_2$)$_5$CH$_3$, and the like.

"Alkoxycarbonylalkyl" means -(alkyl)-C(=O)O-(alkyl), wherein each alkyl is independently defined above, including —CH$_2$—C(=O)O—CH$_3$, —CH$_2$—C(=O)O—CH$_2$CH$_3$, —CH$_2$—C(=O)O—(CH$_2$)$_2$CH$_3$, —CH$_2$—C(=O)O—(CH$_2$)$_3$CH$_3$, —CH$_2$—C(=O)O—(CH$_2$)$_4$CH$_3$, —CH$_2$—C(=O)O—(CH$_2$)$_5$CH$_3$, and the like.

"Alkoxyalkyl" means -(alkyl)-O-(alkyl), wherein each alkyl is independently an alkyl group defined above, including —CH$_2$OCH$_3$, —CH$_2$OCH$_2$CH$_3$, —(CH$_2$)$_2$OCH$_2$CH$_3$, —(CH$_2$)$_2$O(CH$_2$)$_2$CH$_3$, and the like.

"Aryl" means a carbocyclic aromatic group containing from 5 to 10 ring atoms. Representative examples include, but are not limited to, phenyl, tolyl, anthracenyl, fluorenyl, indenyl, azulenyl, pyridinyl and naphthyl, as well as benzo-fused carbocyclic moieties including 5,6,7,8-tetrahydronaphthyl. A carbocyclic aromatic group can be unsubstituted or substituted. In one embodiment, the carbocyclic aromatic group is a phenyl group.

"Aryloxy" means —O-aryl group, wherein aryl is as defined above. An aryloxy group can be unsubstituted or substituted. In one embodiment, the aryl ring of an aryloxy group is a phenyl group.

"Arylalkyl" means -(alkyl)-(aryl), wherein alkyl and aryl are as defined above, including —(CH$_2$)phenyl, —(CH$_2$)$_2$phenyl, —(CH$_2$)$_3$phenyl, —CH(phenyl)$_2$, —CH (phenyl)₃, —(CH₂)tolyl, —(CH₂)anthracenyl, —(CH₂)fluorenyl, —(CH₂)indenyl, —(CH₂)azulenyl, —(CH₂)pyridinyl, —(CH₂)naphthyl, and the like.

"Arylalkyloxy" means —O-(alkyl)-(aryl), wherein alkyl and aryl are defined above, including —O—(CH₂)₂phenyl, —O—(CH₂)₃phenyl, —O—CH(phenyl)₂, —O—CH(phenyl)₃, —O—(CH₂)tolyl, —O—(CH₂)anthracenyl, —O—(CH₂)fluorenyl, —O—(CH₂)indenyl, —O—(CH₂)azulenyl, —O—(CH₂)pyridinyl, —O—(CH₂)naphthyl, and the like.

"Aryloxyalkyl" means -(alkyl)-O-(aryl), wherein alkyl and aryl are defined above, including —CH₂—O-(phenyl), —(CH₂)₂—O-phenyl, —(CH₂)₃—O-phenyl, —(CH₂)—O-tolyl, —(CH₂)—O-anthracenyl, —(CH₂)—O-fluorenyl, —(CH₂)—O-indenyl, —(CH₂)—O-azulenyl, —(CH₂)—O-pyridinyl, —(CH₂)—O-naphthyl, and the like.

"Cycloalkyl" means a monocyclic or polycyclic saturated ring having carbon and hydrogen atoms and having no carbon-carbon multiple bonds. Examples of cycloalkyl groups include, but are not limited to, (C₃-C₇)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. In one embodiment, the cycloalkyl group is a monocyclic ring or bicyclic ring.

"Cycloalkyloxy" means —O-(cycloalkyl), wherein cycloalkyl is defined above, including —O-cyclopropyl, —O-cyclobutyl, —O-cyclopentyl, —O-cyclohexyl, —O-cycloheptyl and the like.

"Cycloalkylalkyloxy" means —O-(alkyl)-(cycloalkyl), wherein cycloalkyl and alkyl are defined above, including —O—CH₂-cyclopropyl, —O—(CH₂)₂-cyclopropyl, —O—(CH₂)₃-cyclopropyl, —O—(CH₂)₄-cyclopropyl, O—CH₂-cyclobutyl, O—CH₂-cyclopentyl, O—CH₂-cyclohexyl, O—CH₂-cycloheptyl, and the like.

"Aminoalkoxy" means —O-(alkyl)-NH₂, wherein alkyl is defined above, such as —O—CH₂—NH₂, —O—(CH₂)₂—NH₂, —O—(CH₂)₃—NH₂, —O—(CH₂)₄—NH₂, —O—(CH₂)₅—NH₂, and the like.

"Mono-alkylamino" means —NH(alkyl), wherein alkyl is defined above, such as —NHCH₃, —NHCH₂CH₃, —NH(CH₂)₂CH₃, —NH(CH₂)₃CH₃, —NH(CH₂)₄CH₃, —NH(CH₂)₅CH₃, and the like.

"Di-alkylamino" means —N(alkyl)(alkyl), wherein each alkyl is independently an alkyl group defined above, including —N(CH₃)₂, —N(CH₂CH₃)₂, —N((CH₂)₂CH₃)₂, —N(CH₃)(CH₂CH₃), and the like.

"Mono-alkylaminoalkoxy" means —O-(alkyl)-NH(alkyl), wherein each alkyl is independently an alkyl group defined above, including —O—(CH₂)—NHCH₃, —O—(CH₂)—NHCH₂CH₃, —O—(CH₂)—NH(CH₂)₂CH₃, —O—(CH₂)—NH(CH₂)₃CH₃, —O—(CH₂)—NH(CH₂)₄CH₃, —O—(CH₂)—NH(CH₂)₅CH₃, —O—(CH₂)₂—NHCH₃, and the like.

"Di-alkylaminoalkoxy" means —O-(alkyl)-N(alkyl)(alkyl), wherein each alkyl is independently an alkyl group defined above, including —O—(CH₂)—N(CH₃)₂, —O—(CH₂)—N(CH₂CH₃)₂, —O—(CH₂)—N((CH₂)₂CH₃)₂, —O—(CH₂)—N(CH₃)(CH₂CH₃), and the like.

"Arylamino" means —NH(aryl), wherein aryl is defined above, including —NH(phenyl), —NH(tolyl), —NH(anthracenyl), —NH(fluorenyl), —NH(indenyl), —NH(azulenyl), —NH(pyridinyl), —NH(naphthyl), and the like.

"Arylalkylamino" means —NH-(alkyl)-(aryl), wherein alkyl and aryl are defined above, including —NH—CH₂-(phenyl), —NH—CH₂-(tolyl), —NH—CH₂-(anthracenyl), —NH—CH₂-(fluorenyl), —NH—CH₂-(indenyl), —NH—CH₂-(azulenyl), —NH—CH₂-(pyridinyl), —NH—CH₂-(naphthyl), —NH—(CH₂)₂-(phenyl) and the like.

"Alkylamino" means mono-alkylamino or di-alkylamino as defined above, such as —N(alkyl)(alkyl), wherein each alkyl is independently an alkyl group defined above, including —N(CH₃)₂, —N(CH₂CH₃)₂, —N((CH₂)₂CH₃)₂, —N(CH₃)(CH₂CH₃) and —N(alkyl)(alkyl), wherein each alkyl is independently an alkyl group defined above, including —N(CH₃)₂, —N(CH₂CH₃)₂, —N((CH₂)₂CH₃)₂, —N(CH₃)(CH₂CH₃) and the like.

"Cycloalkylamino" means —NH-(cycloalkyl), wherein cycloalkyl is as defined above, including —NH-cyclopropyl, —NH-cyclobutyl, —NH-cyclopentyl, —NH-cyclohexyl, —NH-cycloheptyl, and the like.

"Carboxyl" and "carboxy" mean —COOH.

"Cycloalkylalkylamino" means —NH-(alkyl)-(cycloalkyl), wherein alkyl and cycloalkyl are defined above, including —NH—CH₂-cyclopropyl, —NH—CH₂-cyclobutyl, —NH—CH₂-cyclopentyl, —NH—CH₂-cyclohexyl, —NH—CH₂-cycloheptyl, —NH—(CH₂)₂-cyclopropyl and the like.

"Aminoalkyl" means -(alkyl)-NH₂, wherein alkyl is defined above, including CH₂—NH₂, —(CH₂)₂—NH₂, —(CH₂)₃—NH₂, —(CH₂)₄—NH₂, —(CH₂)₅—NH₂ and the like.

"Mono-alkylaminoalkyl" means -(alkyl)-NH(alkyl), wherein each alkyl is independently an alkyl group defined above, including —CH₂—NH—CH₃, —CH₂—NHCH₂CH₃, —CH₂—NH(CH₂)₂CH₃, —CH₂—NH(CH₂)₃CH₃, —CH₂—NH(CH₂)₄CH₃, —CH₂—NH(CH₂)₅CH₃, —(CH₂)₂—NH—CH₃, and the like.

"Di-alkylaminoalkyl" means -(alkyl)-N(alkyl)(alkyl), wherein each alkyl is independently an alkyl group defined above, including —CH₂—N(CH₃)₂, —CH₂—N(CH₂CH₃)₂, —CH₂—N((CH₂)₂CH₃)₂, —CH₂—N(CH₃)(CH₂CH₃), —(CH₂)₂—N(CH₃)₂, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

"Heteroarylalkyl" means -(alkyl)-(heteroaryl), wherein alkyl and heteroaryl are defined above, including —CH₂-triazolyl, —CH₂-tetrazolyl, —CH₂-oxadiazolyl, —CH₂-pyridyl, —CH₂-furyl, —CH₂-benzofuranyl, —CH₂-thiophenyl, —CH₂-benzothiophenyl, —CH₂-quinolinyl, —CH₂-pyrrolyl, —CH₂-indolyl, —CH₂-oxazolyl, —CH₂-benzoxazolyl, —CH₂-imidazolyl, —CH₂-benzimidazolyl, —CH₂-thiazolyl, —CH₂-benzothiazolyl, —CH₂-isoxazolyl, —CH₂-pyrazolyl, —CH₂-isothiazolyl, —CH₂-pyridazinyl, —CH₂-pyrimidinyl, —CH₂-pyrazinyl, —CH₂-triazinyl, cinnolinyl, —CH₂-phthalazinyl, —CH₂-quinazolinyl, —CH₂-pyrimidyl, —CH₂-oxetanyl, —CH₂-azepinyl, —CH₂-piperazinyl, —CH₂-morpholinyl, —CH₂-dioxanyl, —CH₂-thietanyl, —CH₂-oxazolyl, —(CH₂)₂-triazolyl, and the like.

"Heterocycle" means a 5- to 7-membered monocyclic, or 7- to 10-membered bicyclic, heterocyclic ring which is either saturated, unsaturated, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined above. Representative heterocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycle fused to phenyl" means a heterocycle, wherein heterocycle is defined as above, that is attached to a phenyl ring at two adjacent carbon atoms of the phenyl ring.

"Heterocycloalkyl" means -(alkyl)-(heterocycle), wherein alkyl and heterocycle are defined above, including —$CH_2$-morpholinyl, —$CH_2$-pyrrolidinonyl, —$CH_2$-pyrrolidinyl, —$CH_2$-piperidinyl, —$CH_2$-hydantoinyl, —$CH_2$-valerolactamyl, —$CH_2$-oxiranyl, —$CH_2$-oxetanyl, —$CH_2$-tetrahydrofuranyl, —$CH_2$-tetrahydropyranyl, —$CH_2$-tetrahydropyridinyl, —$CH_2$-tetrahydroprimidinyl, —$CH_2$-tetrahydrothiophenyl, —$CH_2$-tetrahydrothiopyranyl, —$CH_2$-tetrahydropyrimidinyl, —$CH_2$-tetrahydrothiophenyl, —$CH_2$-tetrahydrothiopyranyl, and the like.

The term "substituted" as used herein means any of the above groups (i.e., aryl, arylalkyl, heterocycle and heterocycloalkyl) wherein at least one hydrogen atom of the moiety being substituted is replaced with a substituent. In one embodiment, each carbon atom of the group being substituted is substituted with no more that two substituents. In another embodiment, each carbon atom of the group being substituted is substituted with no more than one substituent. In the case of a keto substituent, two hydrogen atoms are replaced with an oxygen which is attached to the carbon via a double bond. Substituents include halogen, hydroxyl, alkyl, haloalkyl, mono- or di-substituted aminoalkyl, alkyloxyalkyl, aryl, arylalkyl, heterocycle, heterocycloalkyl, —$NR_aR_b$, —$NR_aC(=O)R_b$, —$NR_aC(=O)NR_aR_b$, —$NR_aC(=O)OR_b$—$NR_aSO_2R_b$, —$OR_a$, —$C(=O)R_a$, $C(=O)OR_a$—$C(=O)NR_aR_b$, —$OC(=O)R_a$, —$OC(=O)OR_a$, —$OC(=O)NR_aR_b$, —$NR_aSO_2R_b$, or a radical of the formula —Y—Z—$R_a$ where Y is alkanediyl, or a direct bond, Z is —O—, —S—, —N($R_b$)—, —C(=O)—, —C(=O)O—, —OC(=O)—, —N($R_b$)C(=O)—, —C(=O)N($R_b$)— or a direct bond, wherein $R_a$ and $R_b$ are the same or different and independently hydrogen, amino, alkyl, haloalkyl, aryl, arylalkyl, heterocycle, or heterocylealkyl, or wherein $R_a$ and $R_b$ taken together with the nitrogen atom to which they are attached form a heterocycle.

"Haloalkyl" means alkyl, wherein alkyl is defined as above, having one or more hydrogen atoms replaced with halogen, wherein halogen is as defined above, including —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and the like.

"Hydroxyalkyl" means alkyl, wherein alkyl is as defined above, having one or more hydrogen atoms replaced with hydroxy, including —$CH_2OH$, —$CH_2CH_2OH$, —$(CH_2)_2CH_2OH$, —$(CH_2)_3CH_2OH$, —$(CH_2)_4CH_2OH$, —$(CH_2)_5CH_2OH$, —CH(OH)—$CH_3$, —$CH_2CH(OH)CH_3$, and the like.

"Hydroxy" means —OH.

"Sulfonyl" means —$SO_3H$.

"Sulfonylalkyl" means —$SO_2$— (alkyl), wherein alkyl is defined above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

"Sulfinylalkyl" means —SO-(alkyl), wherein alkyl is defined above, including —SO—$CH_3$, —SO—$CH_2CH_3$, —SO—$(CH_2)_2CH_3$, —SO—$(CH_2)_3CH_3$, —SO—$(CH_2)_4CH_3$, —SO—$(CH_2)_5CH_3$, and the like.

"Sulfonamidoalkyl" means —$NHSO_2$-(alkyl), wherein alkyl is defined above, including —$NHSO_2$—$CH_3$, —$NHSO_2$—$CH_2CH_3$, —$NHSO_2$—$(CH_2)_2CH_3$, —$NHSO_2$—$(CH_2)_3CH_3$, —$NHSO_2$—$(CH_2)_4CH_3$, —$NHSO_2$—$(CH_2)_5CH_3$, and the like.

"Thioalkyl" means —S-(alkyl), wherein alkyl is defined above, including —S—$CH_3$, —S—$CH_2CH_3$, —S—$(CH_2)_2CH_3$, —S—$(CH_2)_3CH_3$, —S—$(CH_2)_4CH_3$, —S—$(CH_2)_5CH_3$, and the like.

As used herein, the term "JNK inhibitor(s)" encompasses, but is not limited to, compounds disclosed herein. A JNK inhibitor can be in the form of a pharmaceutically acceptable salt, free base, solvate, hydrate, stereoisomer, clathrate or prodrug thereof. Such inhibitory activity can be determined by an assay or animal model well-known in the art including those set forth in Section 5. In one embodiment, the JNK inhibitor is a compound of structure (I)-(III).

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of JNK inhibitors that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of a JNK inhibitor that comprise —NO, —$NO_2$, —ONO, or —$ONO_2$ moieties. Prodrugs can typically be prepared using well-known methods, such as those described in 1 *Burger's Medicinal Chemistry and Drug*

*Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

Various JNK inhibitors and immunomodulatory compounds contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of JNK inhibitors or immunomodulatory compounds may be used in methods and compositions of the invention. The purified (R) or (S) enantiomers of the specific compounds disclosed herein may be used substantially free of its other enantiomer.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound.

As used herein and unless otherwise indicated, the term "enantiomerically pure" means a stereomerically pure composition of a compound having one chiral center. Similarly, the term "enantiomerically enriched" means a stereomerically enriched composition of a compound having one chiral center.

4. BRIEF DESCRIPTION OF THE FIGURES

FIG. 1 is a cross-sectional view of the cannulation of the vein and artery of a placenta to perfuse the placenta and then collect the perfusate.

FIGS. 2*a-e* are schematics showing the collection, clamping, perfusion, collection and storage of an exsanguinated and perfused placenta.

Figure 3:
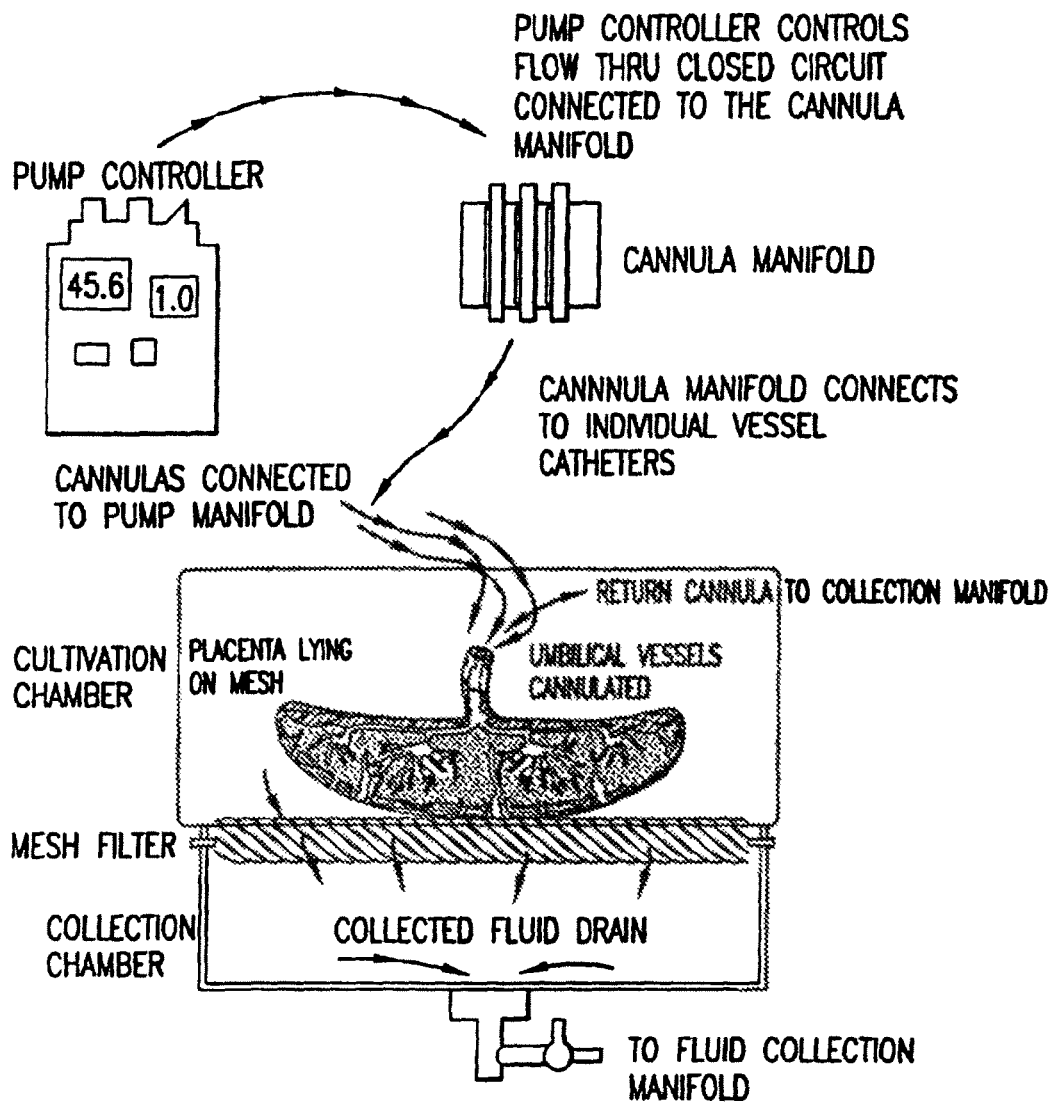

FIG. 3 is a cross-sectional schematic of a perfused placenta in a device for use as a bioreactor.

5. DETAILED DESCRIPTION OF THE INVENTION

5.1 Stem Cell Collection Compositions

In one aspect, the present invention provides compositions for the collection of stem cells, including pluripotent and multipotent stem cells, and committed progenitor cells, from organs, e.g., mammalian placenta, either through physical disruption, e.g., enzymatic digestion, or by perfusion. The compositions facilitate collection of the stem cells, and inhibit apoptosis and/or necrosis of the stem cells, preferably during both collection and subsequent storage. Methods for collecting stem cells, e.g., placental stem cells, using the stem cell collection compositions are discussed below.

In one embodiment, the invention provides a composition for the collection of stem cells from an organ, e.g., placental stem cells, comprising a physiologically-acceptable aqueous solution, and an inhibitor of apoptosis, wherein said composition, when contacted with a population of stem cells, reduces or prevents apoptosis in said population of stem cells as compared to a population of stem cells not contacted with the composition. In one embodiment, the composition is not a naturally-occurring composition. Preferably, the physiologically-acceptable aqueous solution is suitable for the maintenance of a stem cell. The physiologically acceptable aqueous solution can be, for example, an aqueous isotonic solution, such as a physiologically-acceptable aqueous solution, e.g., a buffered saline solution such as 0.9% NaCl solution, phosphate buffered saline, Dulbecco's Modified Eagle's Medium (DMEM), high-glucose Dulbecco's Modified Eagle's Medium (h.DMEM), Krebs solution, and the like. The physiologically-acceptable aqueous solution can be a culture medium, that is, any medium ordinarily used for the culture of mammalian cells, wherein the medium either includes or lacks, e.g., antibiotics or serum. In a specific embodiment, the physiologically acceptable aqueous solution comprises sodium chloride, potassium chloride, magnesium sulfate, calcium chloride, sodium sulfate, potassium sulfate, sodium carbonate, and glucose. The physiologically-acceptable aqueous solution can also comprise, or lack, any essential or non-essential amino acid, or combinations of amino acids.

The stem cell collection composition preferably comprises an enzyme capable of disrupting tissue, e.g., a protease, for example, a protease described in Section 5.1.1, below. The stem cell collection composition comprises an inhibitor of apoptosis, which can be any inhibitor of apoptosis known in the art, e.g., a caspase inhibitor, e.g., a caspase inhibitor described in Section 5.1.2.1, below. Preferably, the inhibitor of apoptosis is a INK inhibitor, e.g., a INK inhibitor described in Section 5.1.2.2, below. In another embodiment, the physiologically-acceptable aqueous solution can also comprise an immunomodulatory compound, e.g., an immunomodulatory compound described in Section 5.1.3, below. The physiologically-acceptable aqueous solution can also comprise a vasodilator, e.g., a vasodilator described in Section 5.1.4, below. The physiologically-acceptable aqueous solution can comprise an inhibitor of necrosis, e.g., an inhibitor of necrosis described in Section 5.1.5, below. The physiologically-acceptable solution can comprise an oxygen-carrying perfluorocarbon, e.g., a perfluorocarbon described in Section 5.1.6, below. The physiologically-acceptable solution can comprise one or a combination of any of the foregoing compounds.

When used as a perfusion solution, the stem cell collection composition of the invention preferably comprises an anticoagulant, such as heparin, citrate, citrate phosphate, citrate phosphate dextrose, CPDA (citrate phosphate dextrose adenine), or the like, at a concentration sufficient to prevent the formation of clots of any residual cord or placental blood. In a specific embodiment, from about 1 to about 100 units of heparin is employed for the collection of stem cells from a single mammalian placenta, and preferably about 1 to about 10 units of heparin per ml is employed.

5.1.1 Enzymes

The composition can comprise one or more enzymes that act to disrupt tissue and/or the junctions between cells, or between cells and a basement membrane. In one embodiment, the enzyme is present in an amount sufficient to dissociate a detectable plurality of stem cells from an organ or tissue, e.g., a placenta, from which stem cells may be derived. Such an enzyme can be, for example, a protease or a polypeptide having protease activity. The protease may be human, mammalian, bacterial, etc., and can be a native protease polypeptide, or a modified polypeptide (e.g., sequence variant, truncation, fusion protein, analog) having protease activity. In various embodiments, the protease is a matrix metalloprotease or a neutral protease. In other embodiments, the enzyme is collagenase (e.g., collagenase I, collagenase IV, a collagenase from *Clostridium histolyticum*, etc.), trypsin (e.g., trypsin-EDTA), thermolysin, elastase, dispase, LIBERASE™ or a combination thereof. Such enzymes may be obtained from commercial sources, e.g., SigmaAldrich (St. Louis, Mo.); Roche Diagnostics (LIBERASE™; Indianapolis, Ind.); Clinalfa (Bloomington, Ind.). Enzymes can be used in any effective concentration, e.g., about 0.1 mg/mL to about 10 mg/mL. In various specific embodiments, trypsin-EDTA (GibcoBRL) can be used at a concentration of about 0.25% (w/v); collagenase-IA (Sigma) can be used at a concentration of about 1 mg/mL; collagenase-I (Worthington) can be used at a concentration of about 0.5 mg/mL; elastase can be used at a concentration of about 1 mg/ml; collagenase-IV can be used at a concentration of about 0.5 mg/mL, and dispase (Worthington) can be used at a concentration of about 0.1 mg/mL. Preferred combinations of enzymes include collagenase I+trypsin; collagenase 1A+trypsin, and elastase+collagenase 1+collagenase IV+dispase. Persons of skill in the art will understand that the example working concentrations provided above can be increased or decreased to optimize a particular digestion or perfusion protocol.

The composition can also comprise a nuclease, e.g., a DNase or RNase. The composition can additionally comprise a mucolytic enzyme. In a specific embodiment, said mucolytic enzyme is hyaluronidase.

5.1.2 Apoptosis Inhibitors

The stem cell collection composition of the present invention comprises an agent that reduces, suppresses or eliminates apoptosis of placental cells, particularly the stem cells to be collected, e.g., an apoptosis inhibitor. Preferably, the agent reduces, suppresses or eliminates apoptosis of placental stem cells during collection and during subsequent storage. The inhibitor of apoptosis may be any known apoptosis inhibitor, e.g., a caspase inhibitor, but is preferably a JNK inhibitor.

5.1.2.1 Caspase Inhibitors

The stem cell collection composition of the invention can comprise a caspase inhibitor. The caspase inhibitor can be an inhibitor of a particular caspase, e.g., caspase 1, caspase 2, caspase 3, caspase 4, caspase 5, caspase 6, caspase 7, caspase 8, caspase 9, caspase 10, caspase 11, caspase 12, or caspase 13. The caspase inhibitor can inhibit several caspases, or can inhibit all known caspases (e.g., pan-caspase inhibitors). The caspase inhibitor can be an inhibitor of a caspase protein, or an inhibitor of activation of a caspase, e.g., inhibitor of a gene encoding a caspase. Examples of caspase inhibitors include, but are not limited to, 2,2'-methylenebis(1,3-cyclohexanedione), a peptide having the sequence Z-Val-Ala-Asp(OMe)-$CH_2F$. a peptide having the sequence Biotin-X-Val-Ala-Asp(OMe)-$CH_2F$ where X is a linker, a peptide having the sequence Ac-Val-Ala-Asp-CHO, Boc-Asp(OMe)-$CH_2F$, a peptide having the sequence Z-Val-Asp(OMe)-Val-Ala-Asp(OMe)-$CH_2F$, a peptide having the sequence Ac-Asp-Glu-Val-Asp-CHO, a peptide having the sequence Ac-Leu-Glu-Cal-Asp-CHO, a peptide having the sequence Z-Trp-Glu(OMe)-His-Asp(OMe)-$CH_2F$, and the like. Caspase inhibitors may be obtained from, e.g., CalBiochem (San Diego, Calif.), BioVision (Mountain View, Calif.); Clontech (Mountain View, Calif.), or R&D Systems, Inc. (Minneapolis, Minn.).

5.1.2.2 JNK Inhibitors

The apoptosis inhibitor of the stem cell collection composition is preferably a JNK inhibitor; more preferably, the JNK inhibitor is a compound disclosed herein. Without wishing to be bound by theory, the addition of an apoptosis inhibitor, particularly a JNK inhibitor, facilitates the collection of stem cells from mammalian placenta by increasing the numbers of viable stem cells that may be collected, and more closely maintaining the cellular environment surrounding such stem cells during the process of collection and isolation.

In a specific embodiment, the JNK inhibitor does not modulate the differentiation or proliferation of a stem cell or population of stem cells contacted with the stem cell collection composition comprising the JNK inhibitor; that is, the JNK inhibitor does not cause a detectable difference in the proliferation or differentiation of the stem cell or stem cell population as compared to a stem cell not contacted with the JNK inhibitor.

JNK inhibitors used in the compositions and methods of the invention include racemic, stereomerically pure and stereomerically enriched JNK inhibitors, stereomerically and enantiomerically pure compounds that have selective JNK inhibitory activities, and pharmaceutically acceptable salts, solvates, hydrates, stereoisomers, clathrates, and prodrugs thereof. Such INK inhibitors can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques.

In one embodiment, a JNK inhibitor has the following structure (I):

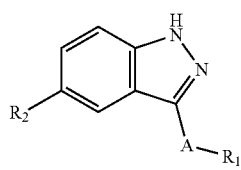

wherein:

A is a direct bond, —(CH$_2$)$_a$—, —(CH$_2$)$_b$CH═CH(CH$_2$)$_c$—, or —(CH$_2$)$_b$C≡C(CH$_2$)$_c$—;

R$_1$ is aryl, heteroaryl or heterocycle fused to phenyl, each being optionally substituted with one to four substituents independently selected from R$_3$;

R$_2$ is —R$_3$, —R$_4$, —(CH$_2$)$_b$C(═O)R$_5$, —(CH$_2$)$_b$C(═O)OR$_5$, —(CH$_2$)$_b$C(═O)NR$_5$R$_6$,
—(CH$_2$)$_b$C(═O)NR$_5$(CH$_2$)$_c$C(═O)R$_6$, —(CH$_2$)$_b$NR$_5$C(═O)R$_6$,
—(CH$_2$)$_b$NR$_5$C(═O)NR$_6$R$_7$, —(CH$_2$)$_b$NR$_5$R$_6$,
—(CH$_2$)$_b$OR$_5$,
—(CH$_2$)$_b$SO$_d$R$_5$ or —(CH$_2$)$_b$SO$_2$NR$_5$R$_6$;

a is 1, 2, 3, 4, 5 or 6;

b and c are the same or different and at each occurrence independently selected from 0, 1, 2, 3 or 4;

d is at each occurrence 0, 1 or 2;

R$_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —C(═O)OR$_8$, —C(═O)NR$_8$R$_9$, —C(═O)NR$_8$OR$_9$, —SO$_2$NR$_8$R$_9$, —NR$_8$SO$_2$R$_9$, —CN, —NO$_2$, —NR$_8$R$_9$, —NR$_8$C(═O)R$_9$, —NR$_8$C(═O)(CH$_2$)$_b$OR$_9$, —NR$_8$C(═O)(CH$_2$)$_b$R$_9$, —O(CH$_2$)$_b$NR$_8$R$_9$, or heterocycle fused to phenyl;

R$_4$ is alkyl, aryl, arylalkyl, heterocycle or heterocycloalkyl, each being optionally substituted with one to four substituents independently selected from R$_3$, or R$_4$ is halogen or hydroxy;

R$_5$, R$_6$ and R$_7$ are the same or different and at each occurrence independently hydrogen, alkyl, aryl, arylalkyl, heterocycle or heterocycloalkyl, wherein each of R$_5$, R$_6$ and R$_7$ are optionally substituted with one to four substituents independently selected from R$_3$; and R$_8$ and R$_9$ are the same or different and at each occurrence independently hydrogen, alkyl, aryl, arylalkyl, heterocycle, or heterocycloalkyl, or R$_8$ and R$_9$ taken together with the atom or atoms to which they are bonded form a heterocycle, wherein each of R$_8$, R$_9$, and R$_8$ and R$_9$ taken together to form a heterocycle are optionally substituted with one to four substituents independently selected from R$_3$.

In one embodiment, -A-R$_1$ is phenyl, optionally substituted with one to four substituents independently selected from halogen, alkoxy, —NR8C(═O)R9, —C(═O)NR8R9, and —O(CH2)bNR8R9, wherein b is 2 or 3 and wherein R8 and R9 are defined above.

In another embodiment, R2 is —R4, —(CH2)bC(═O)R5, —(CH2)bC(═O)OR5, —(CH2)bC(═O)NR5R6, —(CH2)bC(═O)NR5(CH2)cC(═O)R6, —(CH2)bNR5C(═O)R6, —(CH2)bNR5C(═O)NR6R7, —(CH2)bNR5R6, —(CH2)bOR5, —(CH2)bSOdR5 or —(CH2)bSO2NR5R6, and b is an integer ranging from 0-4.

In another embodiment, R2 is —(CH2)bC(═O)NR5R6, —(CH2)bNR5C(═O)R6, 3-triazolyl or 5-tetrazolyl, wherein b is 0 and wherein R8 and R9 are defined above.

In another embodiment, R2 is 3-triazolyl or 5-tetrazolyl.

In another embodiment:
(a) -A-R$_1$ is phenyl, optionally substituted with one to four substituents independently selected from halogen, alkoxy, —NR$_8$C(═O)R$_9$, —C(═O)NR$_8$R$_9$, and —O(CH$_2$)$_b$NR$_8$R$_9$, wherein b is 2 or 3; and
(b) R$_2$ is —(CH$_2$)$_b$C(═O)NR$_5$R$_6$, —(CH$_2$)$_b$NR$_5$C(═O)R$_6$, 3-triazolyl or 5-tetrazolyl, wherein b is 0 and wherein R$_8$ and R$_9$ are defined above.

In another embodiment:
(a) -A-R$_1$ is phenyl, optionally substituted with one to four substituents independently selected from halogen, alkoxy, —NR$_8$C(═O)R$_9$, —C(═O)NR$_8$R$_9$, and —O(CH$_2$)$_b$NR$_8$R$_9$, wherein b is 2 or 3; and
(b) R$_2$ is 3-triazolyl or 5-tetrazolyl.

In another embodiment, R$_2$ is R$_4$, and R$_4$ is 3-triazolyl, optionally substituted at its 5-position with:
(a) a C$_1$-C$_4$ straight or branched chain alkyl group optionally substituted with a hydroxyl, methylamino, dimethylamino or 1-pyrrolidinyl group; or
(b) a 2-pyrrolidinyl group.

In another embodiment, R$_2$ is R$_4$, and R$_4$ is 3-triazolyl, optionally substituted at its 5-position with: methyl, n-propyl, isopropyl, 1-hydroxyethyl, 3-hydroxypropyl, methylaminomethyl, dimethylaminomethyl, 1-(dimethylamino)ethyl, 1-pyrrolidinylmethyl or 2-pyrrolidinyl.

In another embodiment, the compounds of structure (I) have structure (IA) when A is a direct bond, or have structure (IB) when A is —(CH$_2$)$_a$—:

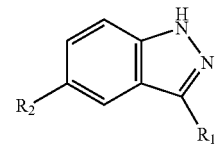

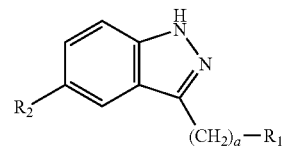

In other embodiments, the compounds of structure (I) have structure (IC) when A is a —(CH$_2$)$_b$CH═CH(CH$_2$)$_c$—, and have structure (ID) when A is —(CH$_2$)$_b$C≡C(CH$_2$)$_a$—:

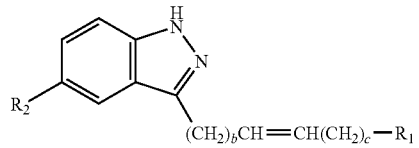

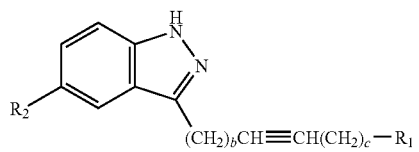

In further embodiments of this invention, $R_1$ of structure (I) is aryl or substituted aryl, such as phenyl or substituted phenyl as represented by the following structure (IE):

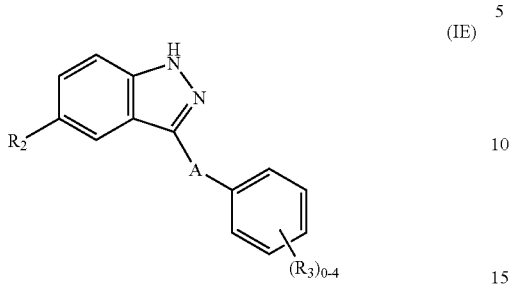

(IE)

In another embodiment, $R_2$ of structure (I) is $-(CH_2)_b NR_4(C=O)R_5$. In one aspect of this embodiment, b=0 and the compounds have the following structure (IF):

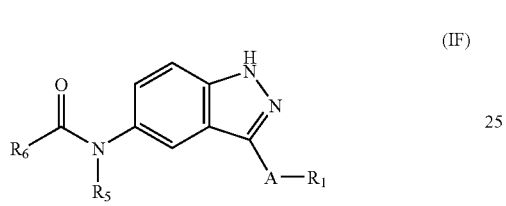

(IF)

Representative $R_2$ groups of the compounds of structure (I) include alkyl (such as methyl and ethyl), halo (such as chloro and fluoro), haloalkyl (such as trifluoromethyl), hydroxy, alkoxy (such as methoxy and ethoxy), amino, arylalkyloxy (such as benzyloxy), mono- or di-alkylamine (such as $-NHCH_3$, $-N(CH_3)_2$ and $-NHCH_2CH_3$), $-NHC(=O)R_4$ wherein $R_6$ is a substituted or unsubstituted phenyl or heteroaryl (such as phenyl or heteroaryl substituted with hydroxy, carboxy, amino, ester, alkoxy, alkyl, aryl, haloalkyl, halo, $-CONH_2$ and $-CONH$ alkyl), $-NH$ (heteroarylalkyl) (such as $-NHCH_2(3$-pyridyl), $-NHCH_2$ (4-pyridyl), heteroaryl (such as pyrazolo, triazolo and tetrazolo), $-C(=O)NHR_6$ wherein $R_6$ is hydrogen, alkyl, or as defined above (such as $-C(=O)NH_2$, $-C(=O)NHCH_3$, $-C(=O)NH(H$-carboxyphenyl), $-C(=O)N(CH_3)_2$), arylalkenyl (such as phenylvinyl, 3-nitrophenylvinyl, 4-carboxyphenylvinyl), heteroarylalkenyl (such as 2-pyridylvinyl, 4-pyridylvinyl).

Representative $R_3$ groups of the compounds of structure (I) include halogen (such as chloro and fluoro), alkyl (such as methyl, ethyl and isopropyl), haloalkyl (such as trifluoromethyl), hydroxy, alkoxy (such as methoxy, ethoxy, n-propyloxy and isobutyloxy), amino, mono- or di-alkylamino (such as dimethylamine), aryl (such as phenyl), carboxy, nitro, cyano, sulfinylalkyl (such as methylsulfinyl), sulfonylalkyl (such as methylsulfonyl), sulfonamidoalkyl (such as $-NHSO_2CH_3$), $-NR_8C(=O)(CH_2)_bOR_9$ (such as NHC $(=O)CH_2OCH_3$), $NHC(=O)R_9$ (such as $-NHC(=O)CH_3$, $-NHC(=O)CH_2C_6H_5$, $-NHC(=O)(2$-furanyl)), and $-O(CH_2)_6NR_8R_9$(such as $-O(CH_2)_2N(CH_3)_2$).

The compounds of structure (I) can be made using organic synthesis techniques known to those skilled in the art, as well as by the methods described in International Publication No. WO 02/10137 (particularly in Examples 1-430, at page 35, line 1 to page 396, line 12), published Feb. 7, 2002, which is incorporated herein by reference in its entirety. Further, specific examples of these compounds are found in this publication.

Illustrative examples of JNK inhibitors of structure (I) are:

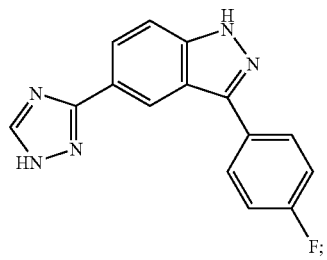

3-(4-Fluoro-phenyl)-5-(1H-
[1,2,4]triazol-3-yl)-1H-indazole

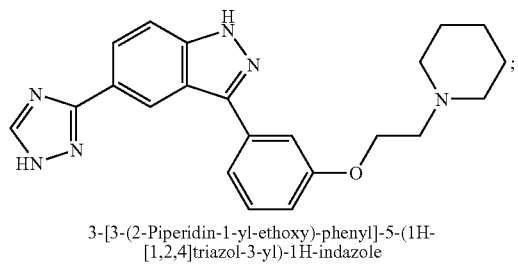

3-[3-(2-Piperidin-1-yl-ethoxy)-phenyl]-5-(1H-
[1,2,4]triazol-3-yl)-1H-indazole

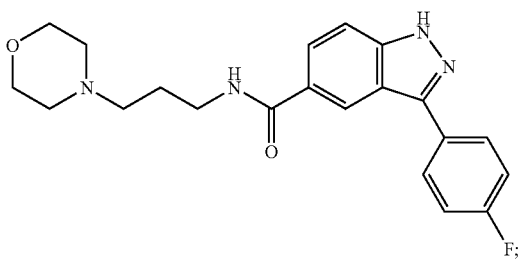

3-(4-Fluoro-phenyl)-1H-indazole-5-carboxylic acid
(3-morpholin-4-yl-propyl)-amide

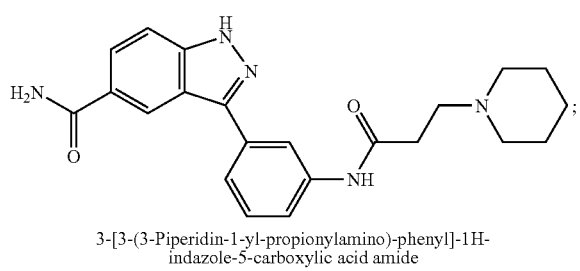

3-[3-(3-Piperidin-1-yl-propionylamino)-phenyl]-1H-
indazole-5-carboxylic acid amide

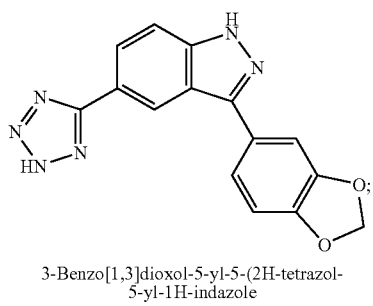

3-Benzo[1,3]dioxol-5-yl-5-(2H-tetrazol-
5-yl-1H-indazole

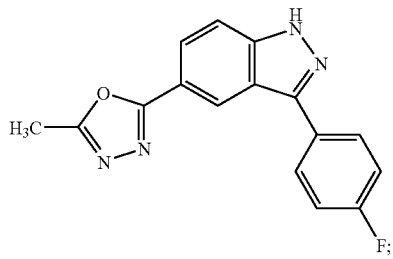

3-(4-Fluoro-phenyl)-5-(5-methyl-[1,3,4]oxadiazol-2-yl)-1H-indazole

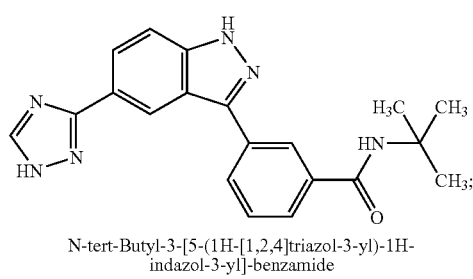

N-tert-Butyl-3-[5-(1H-[1,2,4]triazol-3-yl)-1H-indazol-3-yl]-benzamide

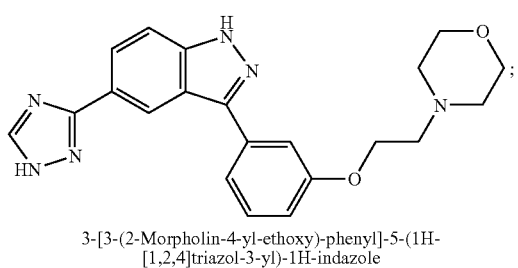

3-[3-(2-Morpholin-4-yl-ethoxy)-phenyl]-5-(1H-[1,2,4]triazol-3-yl)-1H-indazole

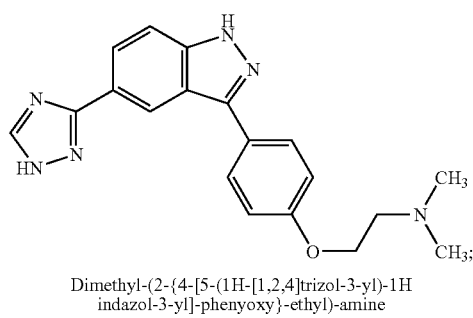

Dimethyl-(2-{4-[5-(1H-[1,2,4]trizol-3-yl)-1H-indazol-3-yl]-phenyoxy}-ethyl)-amine

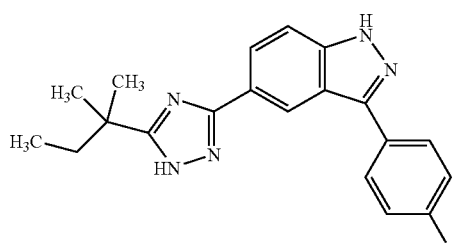

5-[5-(1,1-Dimethyl-propyl)-1H-[1,2,4]triazol-3-yl]-3-(4-fluoro-phenyl)-1H-indazole

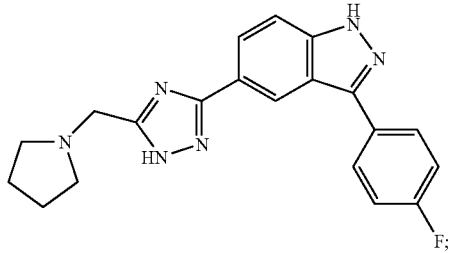

3-(4-Fluoro-phenyl)-5-(5-pyrrolidin-1-ylmethyl-1H-[1,2,4]triazol-3-yl)-1H-indazole

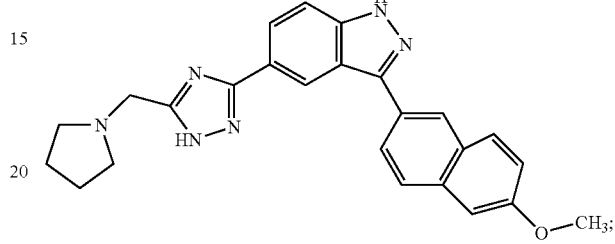

3-(6-Methoxy-naphthalen-2-yl)-5-(5-pyrrolidin-1-ylmethyl-1H-[1,2,4]triazol-3-yl)-1H-indazole

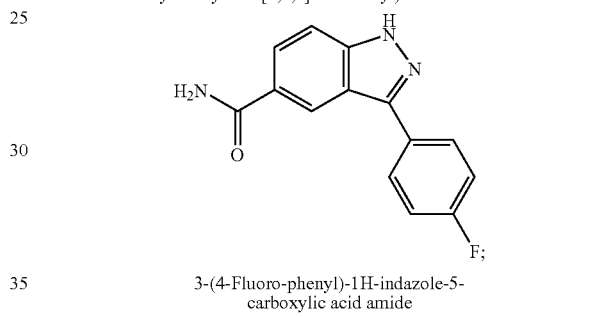

3-(4-Fluoro-phenyl)-1H-indazole-5-carboxylic acid amide and pharmaceutically acceptable salts thereof.

In another embodiment, the JNK inhibitor has the following structure (II):

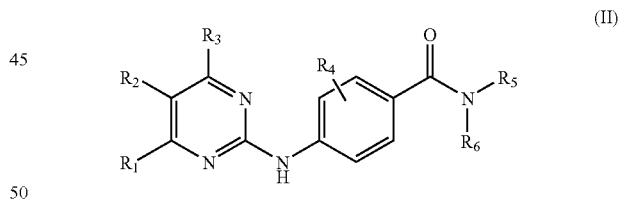

(II)

wherein:

$R_1$ is aryl or heteroaryl optionally substituted with one to four substituents independently selected from $R_7$;

$R_2$ is hydrogen;

$R_3$ is hydrogen or lower alkyl;

$R_4$ represents one to four optional substituents, wherein each substituent is the same or different and independently selected from halogen, hydroxy, lower alkyl and lower alkoxy;

$R_5$ and $R_6$ are the same or different and independently —$R_8$, —$(CH_2)_aC(=O)R_9$, —$(CH_2)_aC(=O)OR_9$, —$(CH_2)_aC(=O)NR_9R_{10}$, —$(CH_2)_aC(=O)NR_9(CH_2)_bC(=O)R_{10}$, —$(CH_2)_aNR_9C(=O)R_{10}$, $(CH_2)_aNR_{11}C(=O)NR_9R_{10}$, —$(CH_2)_aNR_9R_{10}$, —$(CH_2)_aOR_9$, —$(CH_2)_aSO_cR_9$ or —$(CH_2)_aSO_2NR_9R_{10}$;

or R₅ and R₆ taken together with the nitrogen atom to which they are attached to form a heterocycle or substituted heterocycle;

R₇ is at each occurrence independently halogen, hydroxy, cyano, nitro, carboxy, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, —C(=O)OR₈, —OC(=O)R₈, —C(=O)NR₈R₉, —C(=O)NR₈OR₉, —SO_cR₈, —SO_cNR₈R₉, —NR₈SO_cR₉, —NR₈R₉, —NR₈C(=O)R₉, —NR₈C(=O)(CH₂)_bOR₉, —NR₈C(=O)(CH₂)_bR₉, —O(CH₂)_bNR₈R₉, or heterocycle fused to phenyl;

R₈, R₉, R₁₀ and R₁₁ are the same or different and at each occurrence independently hydrogen, alkyl, aryl, arylalkyl, heterocycle, heterocycloalkyl;

or R₈ and R₉ taken together with the atom or atoms to which they are attached to form a heterocycle;

a and b are the same or different and at each occurrence independently selected from 0, 1, 2, 3 or 4; and c is at each occurrence 0, 1 or 2.

In one embodiment, R₁ is a substituted or unsubstituted aryl or heteroaryl. When R₁ is substituted, it is substituted with one or more substituents defined below. In one embodiment, when substituted, R₁ is substituted with a halogen, —SO₂R₈ or —SO₂R₈R₉.

In another embodiment, R₁ is substituted or unsubstituted aryl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl or quinazolinyl.

In another embodiment R₁ is substituted or unsubstituted aryl or heteroaryl. When R₁ is substituted, it is substituted with one or more substituents defined below. In one embodiment, when substituted, R₁ is substituted with a halogen, —SO₂R₈ or —SO₂R₈R₉.

In another embodiment, R₁ is substituted or unsubstituted aryl, preferably phenyl. When R₁ is a substituted aryl, the substituents are defined below. In one embodiment, when substituted, R₁ is substituted with a halogen, —SO₂R₈ or —SO₂R₈R₉.

In another embodiment, R₅ and R₆, taken together with the nitrogen atom to which they are attached form a substituted or unsubstituted nitrogen-containing non-aromatic heterocycle, in one embodiment, piperazinyl, piperidinyl or morpholinyl.

When R₅ and R₆, taken together with the nitrogen atom to which they are attached form substituted piperazinyl, piperadinyl or morpholinyl, the piperazinyl, piperadinyl or morpholinyl is substituted with one or more substituents defined below. In one embodiment, when substituted, the substituent is alkyl, amino, alkylamino, alkoxyalkyl, acyl, pyrrolidinyl or piperidinyl.

In one embodiment, R₃ is hydrogen and R₄ is not present, and the JNK inhibitor has the following structure (IIA):

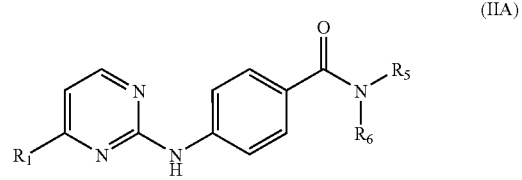

and pharmaceutically acceptable salts thereof.

In a more specific embodiment, R₁ is phenyl optionally substituted with R₇, and having the following structure (IIB):

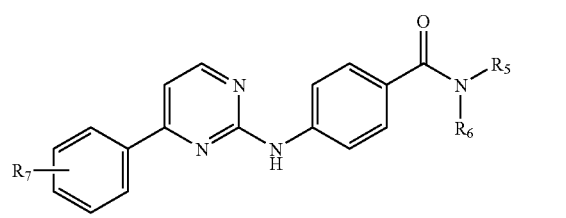

and pharmaceutically acceptable salts thereof.

In still a further embodiment, R₇ is at the para position of the phenyl group relative to the pyrimidine, as represented by the following structure (IIC):

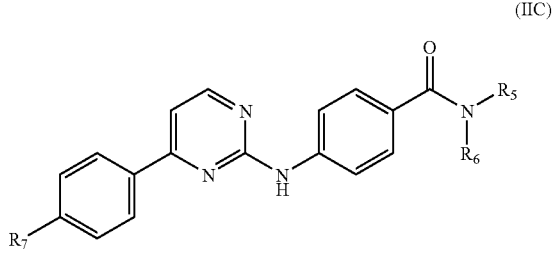

and pharmaceutically acceptable salts thereof.

The JNK inhibitors of structure (II) can be made using organic synthesis techniques known to those skilled in the art, as well as by the methods described in International Publication No. WO 02/46170 (particularly Examples 1-27 at page 23, line 5 to page 183, line 25), published Jun. 13, 2002, which is hereby incorporated by reference in its entirety. Further, specific examples of these compounds are found in the publication.

Illustrative examples of JNK inhibitors of structure (II) are:

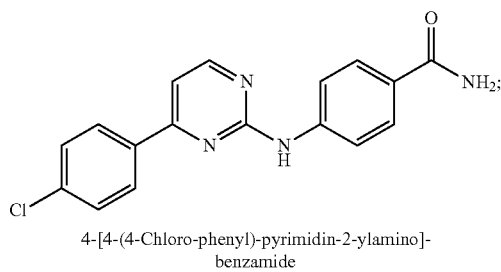

4-[4-(4-Chloro-phenyl)-pyrimidin-2-ylamino]-benzamide

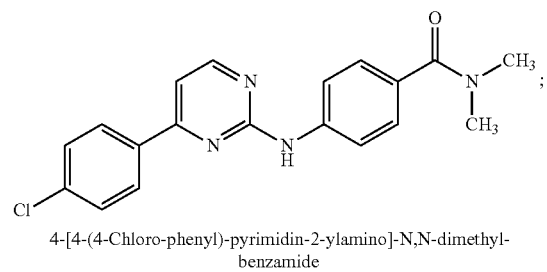

4-[4-(4-Chloro-phenyl)-pyrimidin-2-ylamino]-N,N-dimethyl-benzamide

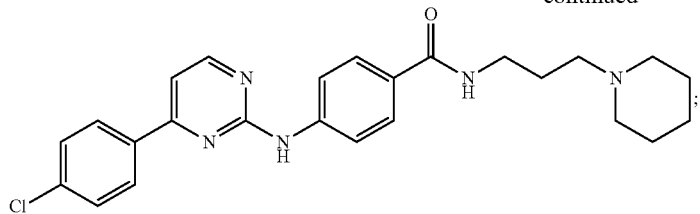

4-[4-(4-Chloro-phenyl)-pyrimidin-2-ylamino]-N-(3-piperidin-1-yl-propyl)-benzamide

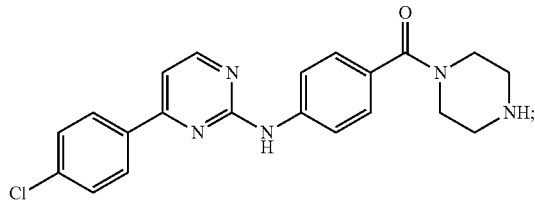

{4-[4-(4-Chloro-phenyl)-pyrimidin-2-ylamino]-phenyl}-piperazin-1-yl-methanone

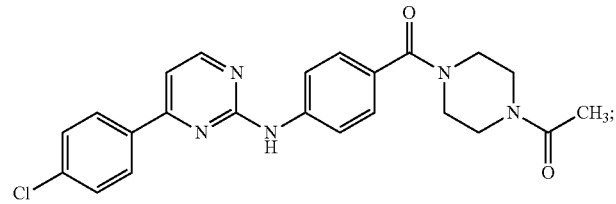

1-(4-{4-[4-(4-Chloro-phenyl)-pyrimidin-2-ylamino]-benzoyl}-piperazin-1-yl)-ethanone

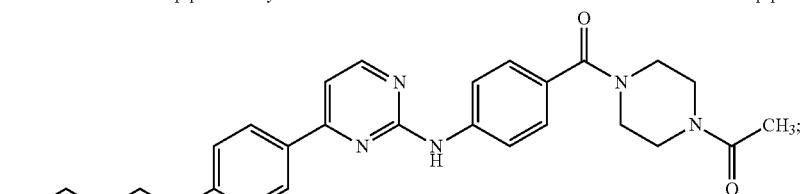

1-[4-(4-{4-[4-(3-Hydroxy-propylsulfanyl)-phenyl]-pyrimidin-2-ylamino}-benzoyl})-piperazin-1-yl]-ethanone

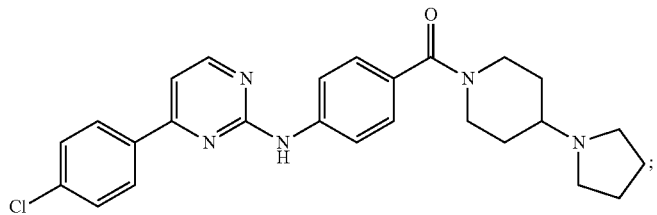

{4-[4-(4-Chloro-phenyl)-pyrimidin-2-ylamino]-phenyl}-(4-pyrrolidin-1-yl-piperidin-1-yl)-methanone and pharmaceutically acceptable salts thereof.

In another embodiment, the JNK inhibitor has the following structure (III):

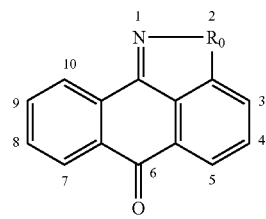

(III)

wherein $R_0$ is —O—, —S—, —S(O)—, —S(O)$_2$—, NH or —CH$_2$—;

the compound of structure (III) being: (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

(a)

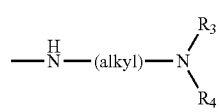

(b)

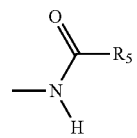

(c)

-continued

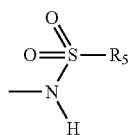
(d)

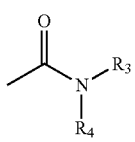
(e)

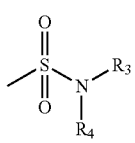
(f)

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

In another embodiment, the JNK inhibitor has the following structure (IIIA):

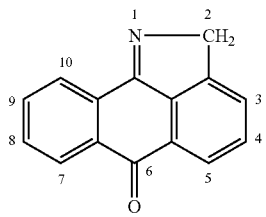

2H-Dibenzo[cd,g]indol-6-one (IIIA)

being: (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

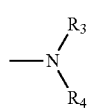
(a)

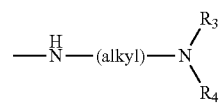
(b)

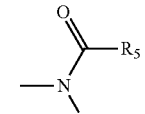
(c)

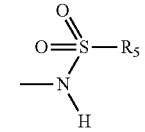
(d)

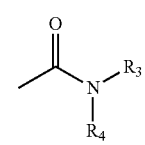
(e)

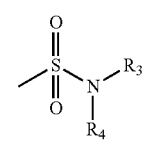
(f)

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

A subclass of the compounds of structure (IIIA) is that wherein the first or second substituent is present at the 5, 7, or 9 position. In one embodiment, the first or second substituent is present at the 5 or 7 position.

A second subclass of compounds of structure (IIIA) is that wherein the first or second substituent is present at the 5, 7, or 9 position;

the first or second substituent is independently alkoxy, aryloxy, aminoalkyl, mono-alkylaminoalkyl, di-alkylaminoalkyl, or a group represented by the structure (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

In another embodiment, the JNK inhibitor has the following structure (IIIB):

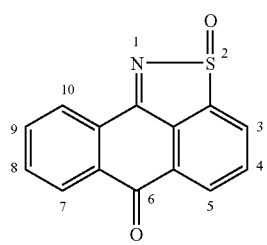

2-Oxo-2H-21⁴-anthra[9,1-cd]
isothiazol-6-one being (i) unsubstituted, (ii) monosubstituted and having a first substituent, or (ii) disubstituted and having a first substituent and a second substituent;

the first or second substituent, when present, is at the 3, 4, 5, 7, 8, 9, or 10 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b) (c), (d), (e), or (f):

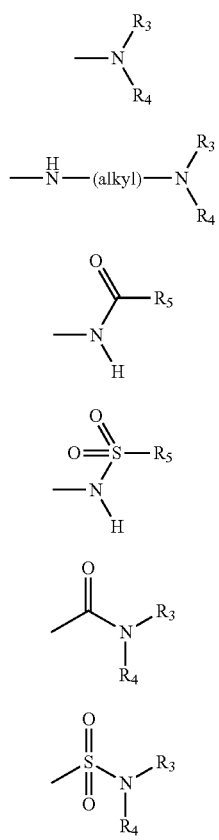

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

A subclass of the compounds of structure (IIIB) is that wherein the first or second substituent is present at the 5, 7, or 9 position. In one embodiment, the first or second substituent is present at the 5 or 7 position.

A second subclass of the compounds of structure (IIIB) is that wherein the first or second substituent is independently alkoxy, aryloxy, or a group represented by the structure (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

In another embodiment, the JNK inhibitor has the following structure (IIIC):

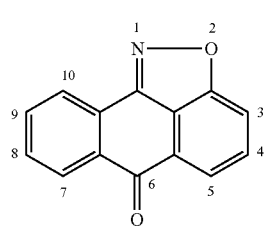

2-Oxa-1-aza-aceanthrylen-6-one being (i) monosubstituted and having a first substituent or (ii) disubstituted and having a first substituent and a second substituent;

the first or second substituent, when present, is at the 3, 4, 5, 7, 8, 9, or 10 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c) (d), (e), or (f):

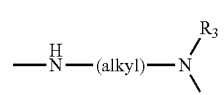

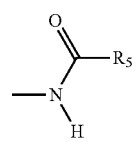

(d)
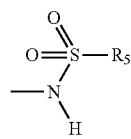

(e)
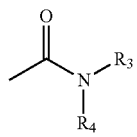

(f)
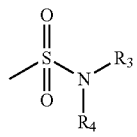

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

A subclass of the compounds of structure (IIIC) is that wherein the first or second substituent is present at the 5, 7, or 9 position. In one embodiment, the first or second substituent is present at the 5 or 7 position.

A second subclass of the compounds of structure (IIIC) is that wherein the first or second substituent is independently alkoxy, aryloxy, aminoalkyl, mono-alkylaminoalkyl, di-alkylaminoalkyl, or a group represented by the structure (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, or cycloalkylalkyl.

In another embodiment, the JNK inhibitor has the following structure (IIID):

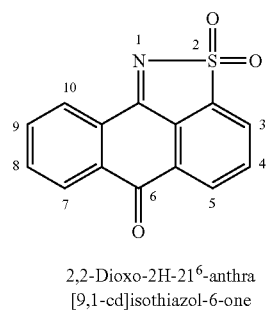

(IIID)

2,2-Dioxo-2H-21$^6$-anthra[9,1-cd]isothiazol-6-one being (i) monosubstituted and having a first substituent present at the 5, 7, or 9 position, (ii) disubstituted and having a first substituent present at the 5 position and a second substituent present at the 7 position, (iii) disubstituted and having a first substituent present at the 5 position and a second substituent present at the 9 position, or (iv) disubstituted and having a first substituent present at the 7 position and a second substituent present at the 9 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

(a)
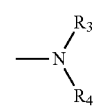

(b)
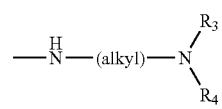

(c)
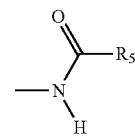

(d)
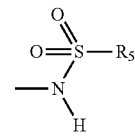

(e)
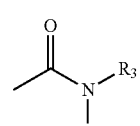

(f)
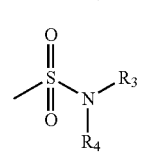

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

A subclass of the compounds of structure (IIID) is that wherein the first or second substituent is present at the 5 or 7 position.

A second subclass of the compounds of structure (IIID) is that wherein the first or second substituent is independently alkyl, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (c), (d), (e), or (f).

Another subclass of the compounds of structure (IIID) is that wherein the first and second substituent are independently alkoxy, aryloxy, or a group represented by the structure (a), (c), (d), (e), or (f);

$R_3$ and $R_4$ are independently hydrogen, alkyl, cycloalkyl, aryl, arylalkyl, or cycloalkylalkyl; and $R_5$ is hydrogen, alkyl, cycloalkyl, aryl, arylalkyl, alkoxycarbonyl, or cycloalkylalkyl.

In another embodiment, the JNK inhibitor has the following structure (IIIE):

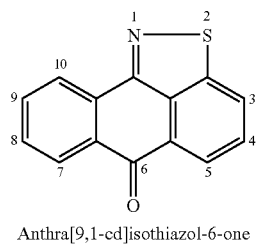

Anthra[9,1-cd]isothiazol-6-one being (i) monosubstituted and having a first substituent present at the 5, 7, or 9 position, (ii) disubstituted and having a first substituent present at the 5 position and a second substituent present at the 9 position, (iii) disubstituted and having a first substituent present at the 7 position and a second substituent present at the 9 position, or (iv) disubstituted and having a first substituent present at the 5 position and a second substituent present at the 7 position;

wherein the first and second substituent, when present, are independently alkyl, halogen, hydroxy, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

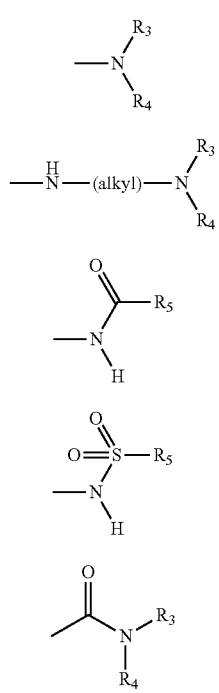

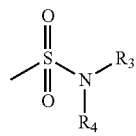

wherein $R_3$ and $R_1$ are taken together and represent alkylidene or a heteroatom-containing cyclic alkylidene or $R_3$ and $R_1$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

A subclass of the compounds of structure (IIIE) is that wherein the first or second substituent is present at the 5 or 7 position.

A second subclass of the compounds of structure (IIIE) is that wherein the compound of structure (IIIE) is disubstituted and at least one of the substituents is a group represented by the structure (d) or (f).

Another subclass of the compounds of structure (IIIE) is that wherein the compounds are monosubstituted. Yet another subclass of compounds is that wherein the compounds are monosubstituted at the 5 or 7 position with a group represented by the structure (e) or (f).

In another embodiment, the JNK inhibitor has the following structure (IIIF):

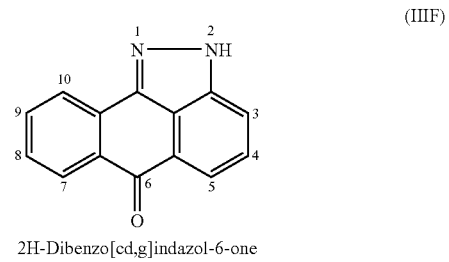 [SMILES: O=C1c2ccccc2-c2n[nH]c3cccc1c23]

2H-Dibenzo[cd,g]indazol-6-one being (i) unsubstituted, (ii) monosubstituted and having a first substituent, or (iii) disubstituted and having a first substituent and a second substituent;

the first or second substituent, when present, is at the 3, 4, 5, 7, 8, 9, or 10 position;

wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, or a group represented by structure (a), (b), (c), (d), (e), or (f):

Illustrative examples of JNK inhibitors of structure (III) are:

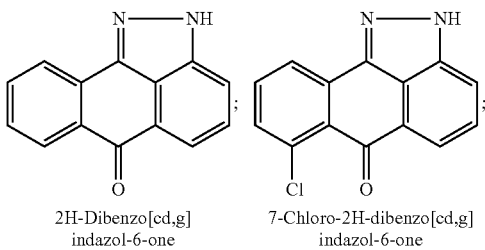

2H-Dibenzo[cd,g]indazol-6-one

7-Chloro-2H-dibenzo[cd,g]indazol-6-one

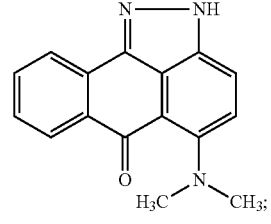

5-Dimethylamino-2H-dibenzo[cd,g]indazol-6-one

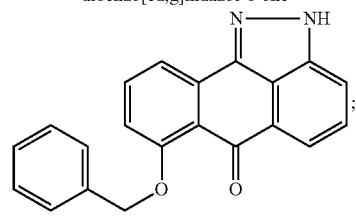

7-Benzyloxy-2H-dibenzo[cd,g]indazol-6-one

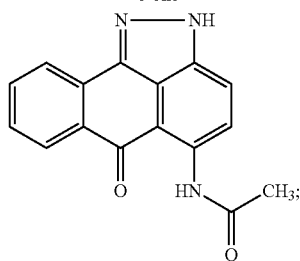

N-(6-Oxo-2,6-dihydro-dibenzo[cd,g]indazol-5-yl)-acetamide

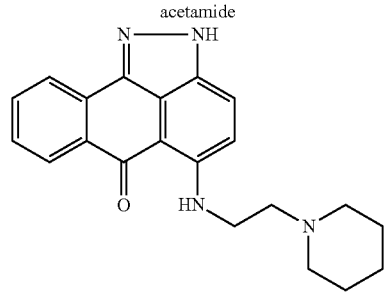

5-(2-Piperidin-1-yl-ethylamino-2H-dibenzo[cd,g]indazol-6-one

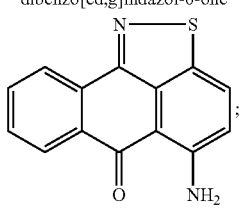

5-Amino-anthra[9,1-cd]isothiazol-6-one

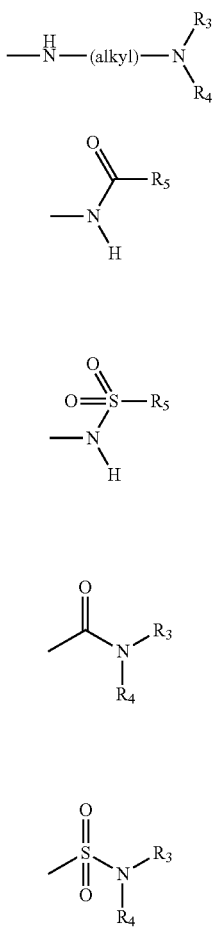

wherein $R_3$ and $R_4$ are taken together and represent alkylidene or a heteroatom-containing cyclic alkylidene or $R_3$ and $R_4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R_5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl.

In one embodiment, the compound of structure (IIIF), or a pharmaceutically acceptable salt thereof is unsubstituted at the 3, 4, 5, 7, 8, 9, or 10 position.

The JNK inhibitors of structure (III) can be made using organic synthesis techniques known to those skilled in the art, as well as by the methods described in International Publication No. WO 01/12609 (particularly Examples 1-7 at page 24, line 6 to page 49, line 16), published Feb. 22, 2001, as well as International Publication No. WO 02/066450 (particularly compounds AA-HG at pages 59-108), published Aug. 29, 2002, each of which is hereby incorporated by reference in its entirety. Further, specific examples of these compounds can be found in the publications.

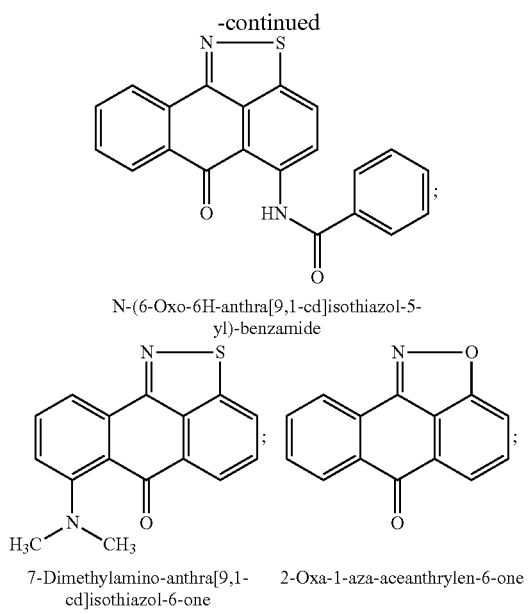

N-(6-Oxo-6H-anthra[9,1-cd]isothiazol-5-yl)-benzamide

7-Dimethylamino-anthra[9,1-cd]isothiazol-6-one

2-Oxa-1-aza-aceanthrylen-6-one and pharmaceutically acceptable salts thereof.

Other JNK inhibitors that are useful in the present compositions and methods include, but are not limited to, those disclosed in International Publication No. WO 00/39101, (particularly at page 2, line 10 to page 6, line 12); International Publication No. WO 01/14375 (particularly at page 2, line 4 to page 4, line 4); International Publication No. WO 00/56738 (particularly at page 3, line 25 to page 6, line 13); International Publication No. WO 01/27089 (particularly at page 3, line 7 to page 5, line 29); International Publication No. WO 00/12468 (particularly at page 2, line 10 to page 4, line 14); European Patent Publication 1 110 957 (particularly at page 19, line 52 to page 21, line 9); International Publication No. WO 00/75118 (particularly at page 8, line 10 to page 11, line 26); International Publication No. WO 01/12621 (particularly at page 8, line 10 to page 10, line 7); International Publication No. WO 00/64872 (particularly at page 9, line 1 to page, 106, line 2); International Publication No. WO 01/23378 (particularly at page 90, line 1 to page 91, Line 11); International Publication No. WO 02/16359 (particularly at page 163, line 1 to page 164, line 25); U.S. Pat. No. 6,288,089 (particularly at column 22, line 25 to column 25, line 35); U.S. Pat. No. 6,307,056 (particularly at column 63, line 29 to column 66, line 12); International Publication No. WO 00/35921 (particularly at page 23, line 5 to page 26, line 14); International Publication No. WO 01/91749 (particularly at page 29, lines 1-22); International Publication No. WO 01/56993 (particularly in at page 43 to page 45); and International Publication No. WO 01/58448 (particularly in at page 39), each of which is incorporated by reference herein in its entirety.

The stem cell collection composition of the invention may comprise one or more solvents or co-solvents to facilitate solvation of a JNK inhibitor. Examples of solvents or co-solvents that can be included in the stem cell collection composition include, but are not limited to, dimethylsulfoxide, ethanol, dimethylformamide, ethylene glycol, propylene glycol, and polyethylene glycol. Generally, only as much solvent or co-solvent is used as necessary to achieve a particular concentration of a particular JNK inhibitor. Preferably, only solvents or co-solvents, or concentrations of solvents or co-solvents, that are compatible with stem cell collection and culture are used.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.1.2.3 Other Apoptosis Inhibitors

Any other inhibitor of apoptosis can be included within the stem cell composition of the invention. For example, in various embodiments, the apoptosis inhibitor can be 2,2'-methylenebis(1,3-cyclohexanedione) (CalBiochem); apoptosis inhibitor 3 protein (i.e., XIAP, Baculoviral IAP repeat containing protein 4, API3, Mammalian IAP homolog A, MIHA, inhibitor of apoptosis protein 3, X-linked inhibitor of apoptosis protein, X-linked IAP, HILP, IAP Like protein, ILP); protein Mcl-1; and the like.

5.1.3 TNF Alpha Inhibitors/Immunomodulatory Compounds

The composition of the invention can include one or more inhibitors of TNF-α, e.g., an immunomodulatory compound. The immunomodulatory compound can be, e.g., thalidomide or a thalidomide derivative.

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), including, but not limited to, those disclosed in U.S. Pat. Nos. 5,635,517, 6,476,052, 6,555,554, and 6,403,613; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; and isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds do not include thalidomide.

Other specific immunomodulatory compounds include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference.

These compounds have the structure I:

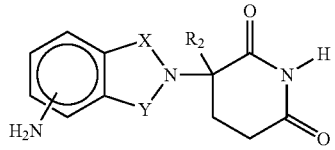

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline; and
1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

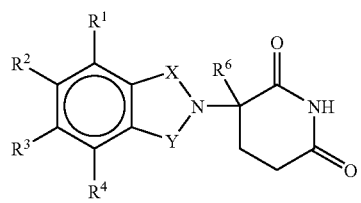

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.
Compounds representative of this class are of the formulas:

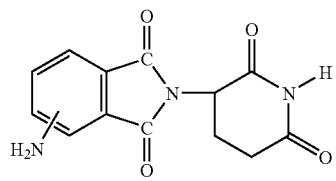

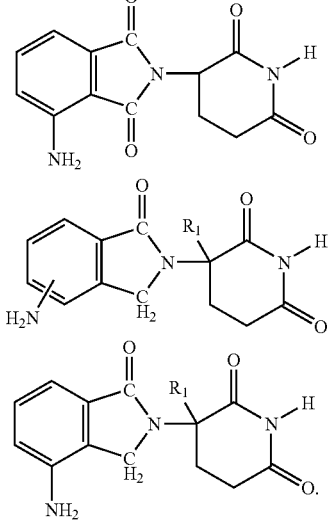

wherein R$^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

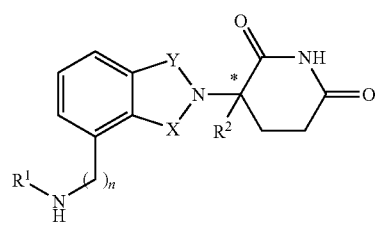

and pharmaceutically acceptable salts, hydrates, solvates, clathrates, enantiomers, diastereomers, racemates, and mixtures of stereoisomers thereof, wherein:
one of X and Y is C=O and the other is CH$_2$ or C=O;
R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;
R$^2$ is H, F, benzyl, (C$_1$-C$_8$)alkyl, (C$_2$-C$_8$)alkenyl, or (C$_2$-C$_8$)alkynyl;
R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_4$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;
R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R⁵ is (C₁-C₈)alkyl, (C₂-C₈)alkenyl, (C₂-C₈)alkynyl, benzyl, aryl, or (C₂-C₅)heteroaryl;

each occurrence of R⁶ is independently H, (C₁-C₈)alkyl, (C₂-C₈)alkenyl, (C₂-C₈)alkynyl, benzyl, aryl, (C₂-C₅)heteroaryl, or (C₀-C₈)alkyl-C(O)O—R⁵ or the R⁶ groups can join to form a heterocycloalkyl group;

n is 0 or 1; and

\* represents a chiral-carbon center.

In specific compounds of formula II, when n is 0 then R¹ is (C₃-C₇)cycloalkyl, (C₂-C₈)alkenyl, (C₂-C₈)alkynyl, benzyl, aryl, (C₀-C₄)alkyl-(C₁-C₆)heterocycloalkyl, (C₀-C₄)alkyl-(C₂-C₅)heteroaryl, C(O)R³, C(O)OR⁴, (C₁-C₈)alkyl-N(R⁶)₂, (C₁-C₈)alkyl-OR⁵, (C₁-C₈)alkyl-C(O)OR⁵, C(S)NHR³, or (C₁-C₈)alkyl-O(CO)R⁵;

R² is H or (C₁-C₈)alkyl; and

R³ is (C₁-C₈)alkyl, (C₃-C₇)cycloalkyl, (C₂-C₈)alkenyl, (C₂-C₈)alkynyl, benzyl, aryl, (C₀-C₄)alkyl-(C₁-C₆)heterocycloalkyl, (C₀-C₄)alkyl-(C₂-C₅)heteroaryl, (C₅-C₈)alkyl-N(R⁶)₂; (C₀-C₈)alkyl-NH—C(O)O—R⁵; (C₁-C₈)alkyl-OR⁵, (C₁-C₈)alkyl-C(O)OR⁵, (C₁-C₈)alkyl-O(CO)R⁵, or C(O)OR⁵; and the other variables have the same definitions.

In other specific compounds of formula II, R² is H or (C₁-C₄)alkyl.

In other specific compounds of formula II, R¹ is (C₁-C₈) alkyl or benzyl.

In other specific compounds of formula II, R¹ is H, (C₁-C₈)alkyl, benzyl, CH₂OCH₃, CH₂CH₂OCH₃, or

[structure: furan-CH₂-]

In another embodiment of the compounds of formula II, R¹ is

[structures: furan-CH₂-, thiophene-CH₂-, or substituted heterocycle-CH(R⁷)-]

wherein Q is O or S, and each occurrence of R⁷ is independently H, (C₁-C₈)alkyl, (C₃-C₇)cycloalkyl, (C₂-C₈)alkenyl, (C₂-C₈)alkynyl, benzyl, aryl, halogen, (C₀-C₄)alkyl-(C₁-C₆)heterocycloalkyl, (C₀-C₄)alkyl-(C₂-C₅)heteroaryl, (C₀-C₈)alkyl-N(R⁶)₂, (C₁-C₈)alkyl-OR⁵, (C₁-C₈)alkyl-C(O)OR⁵, (C₁-C₈)alkyl-O(CO)R⁵, or C(O)OR⁵, or adjacent occurrences of R⁷ can be taken together to form a bicyclic alkyl or aryl ring.

In other specific compounds of formula II, R¹ is C(O)R³.

In other specific compounds of formula II, R³ is (C₀-C₄)alkyl-(C₂-C₅)heteroaryl, (C₁-C₈)alkyl, aryl, or (C₀-C₄)alkyl-OR⁵.

In other specific compounds of formula II, heteroaryl is pyridyl, furyl, or thienyl.

In other specific compounds of formula II, R¹ is C(O)OR⁴.

In other specific compounds of formula II, the H of C(O)NHC(O) can be replaced with (C₁-C₄)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{2-(2,6-dioxo(3-piperidyl))-1,3-dioxoisoindolin-4-yl)methyl}cyclopropyl-carboxamide; 2-chloro-N-{(2-(2,6-dioxo-(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-[1-oxo-4-(benzylamino)isoindolin-2-yl]piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds of the invention belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

[structure III]

and pharmaceutically acceptable salts, hydrates, solvates, clathrates, enantiomers, diastereomers, racemates, and mixtures of stereoisomers thereof, wherein:

one of X and Y is C=O and the other is CH₂ or C=O;

R is H or CH₂OCOR';

(i) each of R¹, R², R³, or R⁴, independently of the others, is halo, alkyl of 1 to 4 carbon atoms, or alkoxy of 1 to 4 carbon atoms or (ii) one of R¹, R², R³, or R⁴ is nitro or —NHR⁵ and the remaining of R¹, R², R³, or R⁴ are hydrogen;

R⁵ is hydrogen or alkyl of 1 to 8 carbons

R⁶ hydrogen, alkyl of 1 to 8 carbon atoms, benzo, chloro, or fluoro; R' is R⁷—CHR¹⁹—N(R⁸R⁹);

R⁷ is m-phenylene or p-phenylene or —(C$_n$H$_{2n}$)— in which n has a value of 0 to 4; each of R⁸ and R⁹ taken independently of the other is hydrogen or alkyl of 1 to 8 carbon atoms, or R⁸ and R⁹ taken together are tetramethylene, pentamethylene, hexamethylene, or —CH$_2$CH$_2$X$_1$CH$_2$CH$_2$— in which X$_1$ is —O—, —S—, or —NH—;

R$^{10}$ is hydrogen, alkyl of to 8 carbon atoms, or phenyl; and

* represents a chiral-carbon center.

Other representative compounds are of formula:

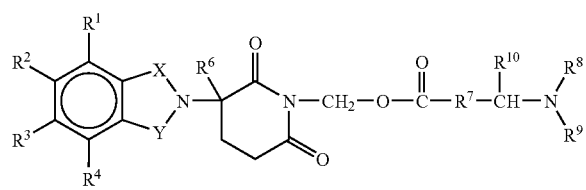

wherein:

one of X and Y is C=O and the other of X and Y is C=O or CH$_2$;

(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzo, chloro, or fluoro;

R$^7$ is m-phenylene or p-phenylene or —(C$_n$H$_{2n}$)— in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S—, or —NH—;

R$^{10}$ is hydrogen, alkyl of to 8 carbon atoms, or phenyl.

Other representative compounds are of formula:

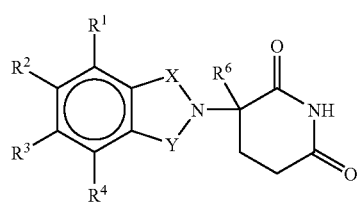

in which one of X and Y is C=O and the other of X and Y is C=O or CH$_2$;

each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and R$^6$ is hydrogen, alkyl of 1 to 8 carbon atoms, benzo, chloro, or fluoro.

Other representative compounds are of formula:

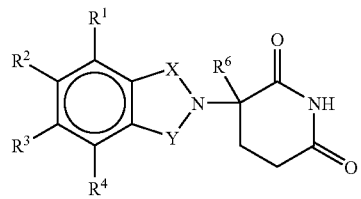

in which:

one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and R$^6$ is alkyl of 1 to 8 carbon atoms, benzo, chloro, or fluoro.

Specific examples of the compounds are of formula:

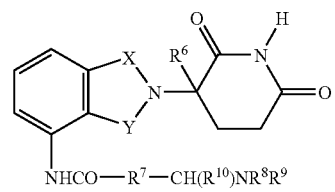

in which:

one of X and Y is C=O and the other of X and Y is C=O or CH$_2$;

R$^6$ is hydrogen, alkyl of 1 to 8 carbon atoms, benzyl, chloro, or fluoro;

R$^7$ is m-phenylene, p-phenylene or —(C$_n$H$_{2n}$)— in which n has a value of 0 to 4;

each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and R$^{10}$ is hydrogen, alkyl of 1 to 8 carbon atoms, or phenyl.

Preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

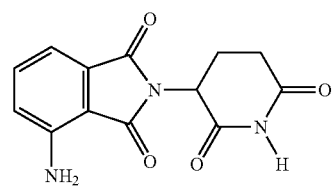

The compound 3-(4-amino-1-oxo-1,3-dihydro-isoindol-2-yl)-piperidine-2,6-dione has the following chemical structure:

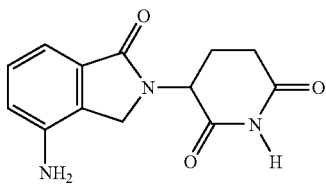

In another embodiment, specific immunomodulatory compounds of the invention encompass polymorphic forms of 3-(4-amino-1-oxo-1,3 dihydro-isoindol-2-yl)-piperidene-2,6-dione such as Form A, B, C, D, E, F, G and H, disclosed in U.S. provisional application No. 60/499,723 filed on Sep. 4, 2003, and the corresponding U.S. non-provisional application, filed Sep. 3, 2004, both of which are incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C. Form A is weakly or not hygroscopic and appears to be the most thermodynamically stable anhydrous polymorph of 3-(4-amino-1-oxo-1,3 dihydro-isoindol-2-yl)-piperidine-2,6-dione discovered thus far.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has endotherms from DSC curve of about 146 and 268° C., which are identified dehydration and melting by hot stage microscopy experiments. Interconversion studies show that Form B converts to Form E in aqueous solvent systems, and converts to other forms in acetone and other anhydrous systems.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C. Form C is not hygroscopic below about 85% RH, but can convert to Form B at higher relative humidities.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C. Form D is either weakly or not hygroscopic, but will typically convert to Form B when stressed at higher relative humidities.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C. Form E can convert to Form C in an acetone solvent system and to Form G in a THF solvent system. In aqueous solvent systems, Form E appears to be the most stable form. Desolvation experiments performed on Form E show that upon heating at about 125° C. for about five minutes, Form E can convert to Form B. Upon heating at 175° C. for about five minutes, Form B can convert to Form F.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated (about 0.25 moles) crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds of the invention include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

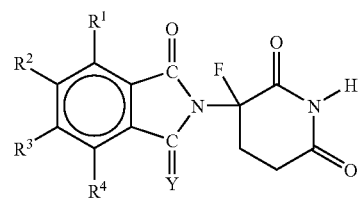

wherein Y is oxygen or $H^2$ and each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds of the invention include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

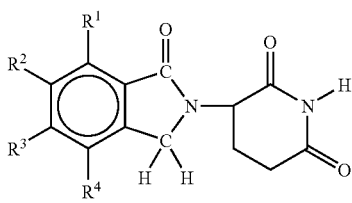

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds of the invention include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

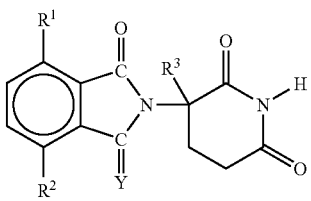

in which:

Y is oxygen or $H_2$, a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

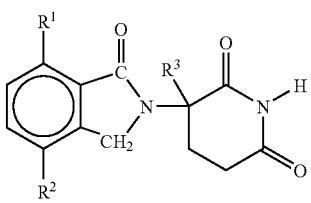

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl.

Specific examples include, but are not limited to, 1-oxo-2-(2,6-dioxopiperidin-3-yl)-4-methylisoindoline.

Other representative compounds are of formula:

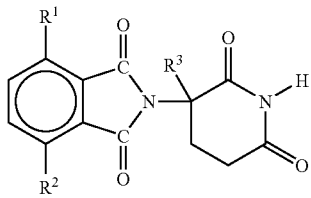

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and $R^3$ is hydrogen, alkyl of from 1 to 4 carbon atoms, or benzyl.

Specific examples include, but are not limited to, 1-oxo-2-(2,6-dioxopiperidin-3-yl)-4-methylisoindoline.

Other specific immunomodulatory compounds include, but are not limited to, 1-oxo and 1,3-dioxoisoindolines substituted in the 4- or 5-position of the indoline ring described in U.S. Pat. No. 6,380,239 and co-pending U.S. application Ser. No. 10/900,270, filed Jul. 28, 2004, which are incorporated herein by reference. Representative compounds are of formula:

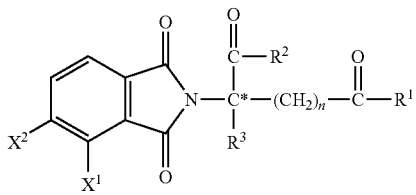

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

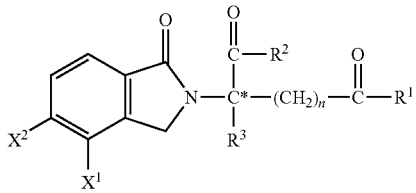

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and R² independent of the other, is hydroxy or NH—Z; R³ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-cabamoyl-butyric acid, which have the following structures, respectively, and pharmaceutically acceptable salts, solvates, prodrugs, and stereoisomers thereof:

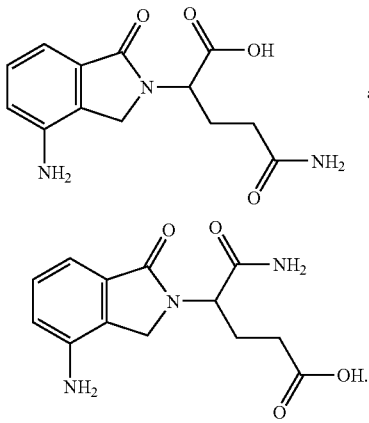

and

Other representative compounds are of formula:

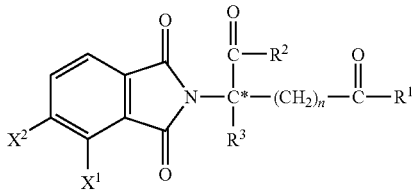

in which the carbon atom designated C* constitutes a center of chirality when n is not zero and R¹ is not R²; one of X¹ and X² is amino, nitro, alkyl of one to six carbons, or NH—Z, and the other of X¹ or X² is hydrogen; each of R¹ and R² independent of the other, is hydroxy or NH—Z; R³ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

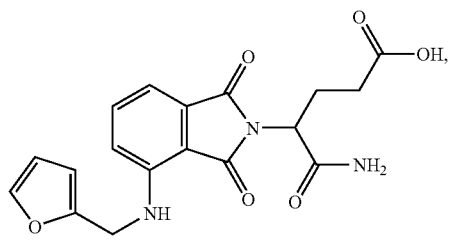

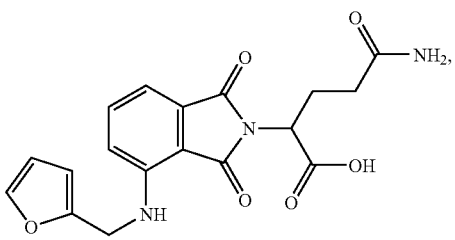

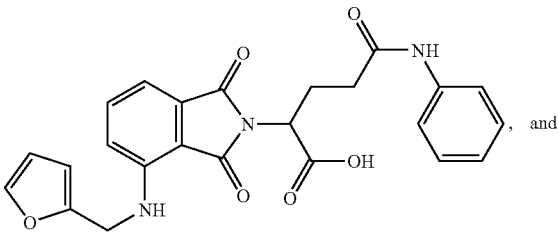

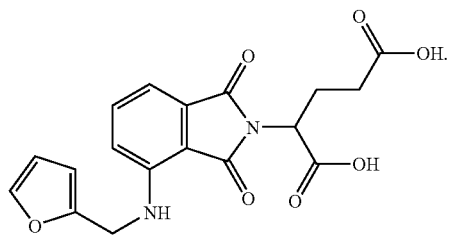

Other specific examples of the compounds are of formula:

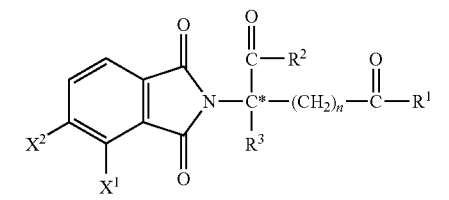

wherein one of X¹ and X² is nitro, or NH—Z, and the other of X¹ or X² is hydrogen;

each of R¹ and R², independent of the other, is hydroxy or NH—Z;

R³ is alkyl of one to six carbons, halo, or hydrogen;

Z is hydrogen, phenyl, an acyl of one to six carbons, or an alkyl of one to six carbons; and n has a value of 0, 1, or 2;

provided that if one of X¹ and X² is nitro, and n is 1 or 2, then R¹ and R² are other than hydroxy; and if —COR² and —(CH₂)ₙCOR¹ are different, the carbon atom designated C* constitutes a center of chirality.

Other representative compounds are of formula:

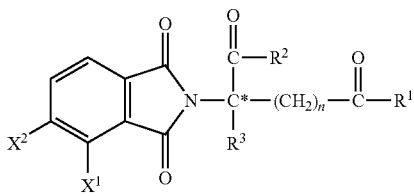

wherein one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_aCOR^1$ are different, the carbon atom designated C* constitutes a center of chirality.

Still other specific immunomodulatory compounds of the invention include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

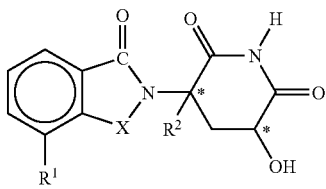

wherein:
the carbon atoms designated * constitute centers of chirality;
X is —C(O)— or —$CH_2$—;
$R^1$ is alkyl of 1 to 8 carbon atoms or —$NHR^3$;
$R^2$ is hydrogen, alkyl of 1 to 8 carbon atoms, or halogen; and
$R^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which
$R^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

Compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

The composition of the invention may also comprise an immunomodulatory compound as described in United States Application Publication No. 2003/0235909, which is incorporated here by reference in its entirety.

5.1.4 Vasodilators

In another embodiment, the stem cell collection composition of the invention comprises a vasodilator. The stem cell collection composition comprising a vasodilator is particularly useful for the collection placenta-derived stem cells by perfusion of the mammalian placenta. The vasodilator may be any vasodilator known in the art, including naturally-occurring vasodilators and artificial vasodilators. In one embodiment, the vasodilator is an antihypertensive drug. Such an antihypertensive drug can be a drug that activates guanylyl cyclase, ADP-ribosyl transferase or cyclooxygenase, or all three, and/or inhibits lipoxygenase. The vasodilator can be an organic or inorganic compound, e.g., atrial natriuretic peptide (ANP), adrenocorticotropin, corticotropin-releasing hormone, sodium nitroprusside, hydralazine, adenosine triphosphate, adenosine, indomethacin or magnesium sulfate, and the like. In other embodiment, the vasodilator is a phosphodiesterase inhibitor (e.g., dibutyryl adenosine, isobutylmethylxanthine, indolidan, rolipram, 2-o-propoxyphenyl-8-azapurin-6-one, trequensin, aminone, milrinon, aminophylline or dipyridamole).

For stem cell collection by perfusion, hydralazine can be used in a concentration of from about 0.1 mM to about 10 mM. Likewise, adenosine can be used at a concentration of about 0.001 mM to about 10.0 mM; adenosine triphosphate can be used at a concentration of about 0.1 mM to about 1000 mM; indomethacin can be used at a concentration of about 1 mg/kg to about 20 mg/kg, wherein "kg" is the weight of an organ, e.g., placenta; or magnesium sulfate can be used at a concentration of about 0.1 mM to about 20 mM.

5.1.5 Inhibitors of Necrosis

The invention further provides a stem cell collection composition that comprises an inhibitor of necrosis. The inhibitor of necrosis can be any physiologically-acceptable necrosis inhibitor known in the art.

Thus, in one embodiment, the invention provides a stem cell collection composition comprising, in a physiologically-acceptable solution, an inhibitor of necrosis. In another embodiment, the invention provides a stem cell collection composition comprising, in a physiologically-acceptable solution, an inhibitor of necrosis and an inhibitor of apoptosis. In a specific embodiment, the inhibitor of necrosis is 2-(1H-Indol-3-yl)-3-pentylamino-maleimide, pyrrolidine dithiocarbamate, or clonazepam. In other specific embodiments, the stem cell collection composition comprising a necrosis inhibitor, or an inhibitor of necrosis and an inhibitor of apoptosis, can comprise one or more enzymes, e.g., one or more of the enzymes described in Section 5.1.1, above; an inhibitor of apoptosis described in Section 5.1.2, above; an immunomodulatory compound, e.g., an immunomodulatory compound described in Section 5.1.3, above; a vasodilator, e.g., a vasodilator described in Section 5.1.4, above, or an oxygen-carrying perfluorocarbon, e.g., an oxygen-carrying perfluorocarbon described in Section 5.1.6, below.

In one embodiment, the invention provides a method of isolating a stem cell, comprising contacting said stem cell with a solution comprising an inhibitor of necrosis, and isolating said stem cell. In another embodiment, the invention provides a method of isolating a stem cell comprising contacting said stem cell with a solution comprising an inhibitor of necrosis and an inhibitor of apoptosis, and isolating said stem cell. In specific embodiments, the inhibitor of necrosis is 2-(1H-Indol-3-yl)-3-pentylamino-maleimide, pyrrolidine dithiocarbamate, clonazepam, and the like.

5.1.6 Oxygen-Carrying Perfluorocarbons

The stem cell collection composition of the invention can further comprise one or more oxygen-carrying perfluorocarbons. Generally, oxygen-carrying perfluorocarbons are not water miscible, and the stem cell collection composition is otherwise generally a physiologically-acceptable aqueous solution. The stem cell collection composition comprising an oxygen-carrying perfluorocarbon therefore can comprise separate aqueous and perfluorocarbon phases, or can comprise both phases as an emulsion. Stem cells may be contacted during collection with either a two-phase or an emulsified composition, or may be collected with the aqueous phase followed by contact with the perfluorocarbon phase. For example, stem cells in an organ, e.g., a placenta, can be contacted during perfusion or tissue disruption, e.g., enzymatic digestion, with a physiologically-acceptable aqueous solution comprising an inhibitor of apoptosis, e.g., a JNK inhibitor, and the resulting cell suspension combined with a perfluorocarbon. The physiologically acceptable solution comprising an apoptosis inhibitor and the perfluorocarbon may also be mixed, e.g., emulsified, prior to collection of stem cells. The emulsion can then be used, e.g., as a perfusion solution, or a solution into which cells from a disrupted organ, or portion thereof, can be suspended.

Thus, in one embodiment, said apoptosis inhibitor and said perfluorocarbon are contained within a single solution, e.g., an emulsion, prior to contacting stem cells to be preserved. In another embodiment, said apoptosis inhibitor is contained within a first solution, and said perfluorocarbon is contained within a second solution, prior to said contacting.

The oxygen-carrying perfluorocarbon can comprise a single species of perfluorocarbon, or can comprise a plurality of species. For example, the oxygen-carrying perfluorocarbon can comprise a perfluoroalkyl or perfluoroether. In specific embodiments, the oxygen-carrying perfluorocarbon can comprise one or more of an aliphatic perfluorocarbon of the general structure $C_nF_{2n+1}R$ or $C_nF_{2n}R_2$, where n is an integer from 8 to 12 and R is a lipophilic moiety; a perfluoroether of the general structure $C_nF_{2n}+1$-O-$C_nF_{2n+1}$; perfluorooctylethane, perfluorooctyldecane, perfluorodecalin, perfluoromethylbicyclo [3.3.1]-nonane, perfluorodimethyl bicyclononane, perfluoro-2,2,4,4-tetramethylpentane, perfluorotripropylamine, bis(F-butyl)ethene, (F-isopropyl) (F-hexyl)ethene, perfluoromethyladamantane, perfluorodimethyladamantane, F—N-methyldecahydroisoquinoline, F-4-methyloctahydroquinolidizine, perfluorooctyl bromide, perfluorodecyl bromide, α,ω-dichloro-F-decane, α,ω-dibromo-F-decane, $C_{10}F_{21}CH=CH_2$, $C_{10}F_{21}CH_2CH_3$, and the like.

The oxygen-carrying perfluorocarbon may be present in the stem cell collection composition may be present in an emulsion in an amount representing about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, or about 125% weight/volume of the emulsion. Preferably, the stem cell collection composition comprising an oxygen-carrying perfluorocarbon additionally comprises an emulsifier (e.g., a surfactant). Such an emulsifier can be any physiologically-acceptable emulsifier, and is preferably lecithin. The emulsifier can be present in an amount of about 0.1% to about 7% (w/v).

In a preferred embodiment, the stem cell collection composition comprises a first perfluorocarbon and a second perfluorocarbon having a higher molecular weight than the first perfluorocarbon. Typically, the total volume of perfluorocarbon comprises about 50% to about 99.9% of the first perfluorocarbon, and about 0.1% to about 50% of the second perfluorocarbon. In one embodiment, the first perfluorocarbon is perfluorooctyl bromide, and the second perfluorocarbon is perfluorodecyl bromide.

The oxygen-carrying perfluorocarbon and aqueous portion of the stem cell collection composition can be emulsified using standard emulsification techniques, e.g., high-pressure homogenization as described in U.S. Pat. No. 4,987,154; shaking in a flask; mechanical or ultrasonic emulsification of an emulsion formulation in a Manton-Gaulin mixer or Microfluidizer (Microfluidics Corp., Newton, Mass.); etc. Where the stem cell collection composition comprises two or more distinct species of oxygen-carrying perfluorocarbon, the species can be combined with the aqueous phase in the desired ratio, together with the emulsifier. Usually, a preemulsion mixture is prepared by simple mixing or blending of the various components. This preemulsion is then emulsified in the desired emulsification apparatus. The emulsification technique, where the stem cells are collected in a two-phase solution, is preferably selected so as to minimize damage to the stem cells.

Apart from inclusion within a stem cell collection composition, oxygen-carrying perfluorocarbons can also be used in the preservation of a placenta during transport from the site of placental collection (e.g., delivery room) to the site of stem cell collection. In one embodiment, a placenta, from which stem cells are to be collected, is contacted with a composition comprising one or more oxygen-carrying perfluorocarbons for at least part of the time between placental collection and stem cell collection. Preferably, the placenta is kept in contact with the oxygen-carrying perfluorocarbon for a majority of the time between placental collection and stem cell collection. In another embodiment, the placenta is contacted with a composition comprising one or more oxygen-carrying perfluorocarbons and one or more organ preservation media (e.g., UW solution; see Section 5.3, below) for at least part of the time between placental collection and stem cell collection.

5.1.7 Other Components

The stem cell collection composition can comprise other components that can reduce injury to the cell caused by an aspect of collection or storage, organismal contamination, etc., or that can facilitate the collection of the stem cells.

The stem cell collection composition can comprise a stem cell mobilizer and/or stimulator of hematopoiesis, such as a VLA-4 (Very Late Antigen) antagonist (e.g., an alpha-4 integrin antagonist, such as an antibody, e.g., Natalizumab or Anti-phospho-Integrin (Ser988), clone 6.33 (Upstate Cell Signaling Solutions), or a peptide (e.g., phenylacetyl-leu-asp-phe-D-prolineamide (Cytel Corp., San Diego Calif.))) at, e.g., 1-10 mg/kg of placenta weight, a CXCR-4 agonist (e.g., MOZOBIL™ (also known as AMD3100; AnorMED, Langley, BC, Canada) at, e.g., 0.01-10 mg/kg, alone or with G-CSF; SDF-1 (stromal cell-derived factor) analogs (e.g., CTCE-0214 from Chemokine Therapeutics Corp.) or an anti-SDF-1 antibody at, e.g., 0.01-10 mg/kg, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, etc. In a particular embodiments, the antibiotic is active against Gram(+) and/or Gram(-) bacteria, e.g., *Pseudomonas aeruginosa, Staphylococcus aureus*, and the like.

The stem cell collection composition can comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.2 Methods of Collecting Stem Cells Using the Compositions of the Invention

The invention further provides methods of collecting and isolating placental stem cells using the stem cell collection composition described above.

In one embodiment, the invention provides a method of isolating a stem cell, comprising contacting said stem cell with a solution comprising an inhibitor of necrosis, e.g., an inhibitor of necrosis described in Section 5.1.5, above, and isolating said stem cell. In another embodiment, the invention provides a method of isolating a stem cell, comprising contacting said stem cell with a solution comprising an inhibitor of apoptosis, e.g., an inhibitor of apoptosis described in Section 5.1.2, above, and isolating said stem cell. In another embodiment, the invention provides a method of isolating a stem cell comprising contacting said stem cell with a solution comprising an inhibitor of necrosis e.g., an inhibitor of necrosis described in Section 5.1.5, above and an inhibitor of apoptosis, e.g., an inhibitor of apoptosis described in Section 5.1.2, above, and isolating said stem cell. In specific embodiments, the inhibitor of necrosis is 2-(1H-Indol-3-yl)-3-pentylamino-maleimide, pyrrolidine dithiocarbamate, clonazepam, and the like. In a specific embodiment, the inhibitor of apoptosis is a caspase inhibitor or a c-Jun N-terminal kinase (JNK) inhibitor. In another specific embodiment, the JNK inhibitor does not modulate the differentiation or proliferation of said stem cell prior to said isolation; that is, the JNK inhibitor does not detectably alter the differentiation or proliferation of the stem cell during contact with the JNK inhibitor. The stem cell in the method can be isolated from mammalian placenta, umbilical cord, placental blood or umbilical cord blood. The method also encompasses contacting the stem cell with an oxygen-carrying perfluorocarbon, e.g., an oxygen-carrying perfluorocarbon described in Section 5.1.6. In another embodiment, the method comprises contacting said stem cell with an enzyme, e.g., a protease. The protease can be, e.g., a matrix metalloprotease or a neutral protease, and can be, for example, collagenase, thermolysin or dispase. The stem cells can, in another embodiment, be contacted with a mucolytic enzyme, such as hyaluronidase.

The stem cell collection composition used in the method can comprise a solution, for example, a saline solution or culture medium. In some embodiments, the solution comprises hydroxyethyl starch, lactobionic anion and raffinose, and/or UW solution.

In preferred embodiments, the stem cell is not exposed to hypoxic or shear stress during isolation, or such stresses are minimized to the extent possible. For example, in one embodiment, the stem cell is exposed during isolation to a hypoxic condition for less than six hours, less than two hours, less than one hour, or less than thirty minutes during said isolation, wherein a hypoxic condition is a concentration of oxygen that is less than normal blood oxygen concentration.

5.2.1 Physical Disruption

In one embodiment, stem cells are collected from a mammalian organ, e.g. placenta, by physical disruption, e.g., enzymatic digestion, of the organ. For example, the organ, or a portion thereof, may be, e.g., crushed, sheared, minced, diced, chopped, macerated or the like, while in contact with the stem cell collection composition of the invention, and the tissue subsequently digested with one or more enzymes. The organ, or a portion thereof, may also be physically disrupted and digested with one or more enzymes, and the resulting material then immersed in, or mixed into, the stem cell collection composition of the invention. The stem cell collection composition of the invention can comprise the enzyme(s). Any method of physical disruption can be used, provided that the method of disruption leaves a plurality, preferably a majority, preferably at least 50%, 60%, 70%, 80%, 90%, 95%, 98%, or 99% of the cells in said organ viable, as determined by, e.g., trypan blue exclusion. Preferably, the method of disruption leaves a plurality, preferably a majority, preferably at least 50%, 60%, 70%, 80%, 90%, 95%, 98%, or 99% of the stem cells in said organ viable, as determined by, e.g., trypan blue exclusion.

Any combination of enzymes can be used, e.g., one or more of the proteases and/or mucolytic enzymes disclosed in Section 5.1.1, above. For example, placental tissue may be digested using collagenase (e.g., collagenase I, II, III or IV), dispase, elastase, trypsin etc. alone, or any combination thereof. Typical concentrations for tissue digestion enzymes include, e.g., 50-200 u/mL for collagenase I and collagenase IV, 1-10 u/mL for dispase, and 10-100 u/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

5.2.2 Perfusion

Cells, e.g., stem cells, can be collected from an organ, e.g., a mammalian placenta, by perfusion, e.g., through the placental vasculature, using the stem cell collection composition of the invention as a perfusion solution. In one embodiment, a mammalian placenta is perfused by passage of perfusion solution through either or both of the umbilical artery and umbilical vein (FIG. 1, FIGS. 2A-2D). The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold, as shown in FIG. 3.

Perfusion can also be aided by the use of a pressure chamber, e.g., a chamber in which the pressure of the atmosphere surrounding the placenta during perfusion is greater than atmospheric pressure. In one embodiment, the pressure chamber, or tank, comprises a plurality of ports that allow ingress and egress of a plurality of tubes. Such tubes can be connected to placental veins and arteries so as to facilitate perfusion by collection of exudate of perfusate from the placenta, or of perfusate that has been circulated only through the placental vasculature. The tank also comprises a port, connected to a pump that controls the atmospheric pressure inside the tank. In a specific example, perfusion fluid is pumped into the placental (fetal) vasculature using one pump, and a second pump is used to control atmospheric pressure against the placenta to, for example, apply pressure to aid in collecting perfusate, or to mimic the natural pressure against the placenta as when the placenta is carried in vivo.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition of the invention, through the placental vasculature, or through the placental vasculature and surrounding tissue. Perfusion solution can be passed through any of the umbilical vessels, in any combination. Perfusion solution can be passed through the placental vasculature in either direction (that is, perfusion solution can be perfused into a placental artery or into a placental vein, or collected from a placental artery or a placental vein, or from seepage from placental tissue). In one embodiment, the umbilical artery and the umbilical vein are connected simultaneously, as shown in FIG. 1, to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid, e.g., stem cell collection composition of the invention, from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination. Because the invention contemplated the perfusion of any mammalian placenta, the placenta can be perfused with at least, or no more than, 1.0 mL, 2.0 mL, 3.0 mL, 4.0 mL, 5.0 mL, 6.0 mL, 7.0 mL, 8.0 mL, 9.0 mL, 10 mL, 15 mL, 20 mL, 25 mL, 30 mL, 35 mL, 40 mL, 45 mL, 50 mL, 55 mL, 60 mL, 65 mL, 70 mL, 75 mL, 80 mL, 85 mL 90 mL, 95 mL, 100 mL, 200 mL, 300 mL, 400 mL, 500 mL 600 mL, 700 mL, 800 mL, 900 mL, 1000 mL, 1500 mL, 2000 mL, 2500 mL, 3000 mL, 3500 mL, 4000 mL, 4500 mL, 5000 mL, 5500 mL, 6000 mL, 6500 mL, 7000 mL, 7500 mL, 8000 mL, 8500 mL, 9000 mL, 9500 mL, or 10,000 mL of perfusion liquid to collect placenta-derived stem cells.

The organ, e.g. placenta, can be perfused a plurality of times over the course of several hours or several days. Where the organ is to be perfused a plurality of times, it may be maintained or cultured under aseptic conditions in a container or other suitable vessel, and perfused with the stem cell collection composition of the invention, or a standard perfusion solution (e.g., a normal saline solution such as phosphate buffered saline ("PBS")) with or without an anticoagulant (e.g., heparin, warfarin sodium, coumarin, bishydroxycoumarin, citrate, citrate phosphate dextrose adenine (CPDA-1)), and/or with or without an antimicrobial agent (e.g., antibiotics such as streptomycin (e.g., at 40-100 µg/ml), penicillin (e.g., at 40 U/ml), amphotericin B (e.g., at 0.5 µg/ml). In one embodiment, an isolated organ, e.g. placenta, is maintained or cultured for a period of time without collecting the perfusate, such that the organ is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused organ may be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The organ, e.g., placenta, may be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled.

The placenta can optionally be cultured in one or more of the stem cell collection compositions described herein, wherein the stem cell collection composition, rather than being immediately collected, is allowed to remain in the placental vasculature for a time prior to collection of placenta-derived stem cells. For example, in one embodiment, a placenta can be perfused with enough of a stem cell collection composition to fill the placental vasculature, wherein the stem cell collection composition comprises, e.g., a vasodilator, which can facilitate subsequent collection of stem cells. In another embodiment, a placenta is perfused with a stem cell collection composition comprising, e.g., one or more proteases. The placenta is cultured with the stem cell collection composition for a time sufficient for the one or more proteases to begin digestion of the placenta tissue, e.g., 1-5 hours, whereupon the stem cells are collected by further perfusion.

The placenta can, as well, be perfused using different stem cell collection compositions. For example, a placenta can first be perfused with a stem cell collection composition comprising a vasodilator for a time sufficient for the vasodilator to dilate placental vessels. Preferably, only as much of the stem cell collection composition as needed to fill the placental vasculature is used. The placenta can optionally be cultured in the stem cell collection composition for a time prior to stem cell collection, as described above. The placenta is then perfused with a second stem cell collection composition comprising one or more proteases. The placenta can optionally be cultured for a time with this stem cell collection composition for a time sufficient for the protease(s) to begin digestion of the placental tissue. The placenta can then be perfused with additional stem cell collection composition, or with a third stem cell collection composition, e.g., a stem cell collection composition comprising one or more apoptosis and/or necrosis inhibitors. Other sequential combinations of different stem cell collection compositions will be easily appreciated by those of skill in the art.

In one embodiment, for spontaneous vaginal delivery (SVD), the placental vasculature is filled with the collection composition of the invention, and the placenta is bathed (e.g., immersed) in the solution, and stem cells are collected, e.g., by perfusion, at from about 20 to about 24 hours after delivery. In another embodiment, the placenta is immersed in the collection composition for at least part of the time between delivery and stem cell collection. In another embodiment, the vasculature of the placenta is filled with the collection composition for at least part of the time between delivery and stem cell collection. In another embodiment, the placenta is refrigerated (e.g., at about 0° C. to about 5° C. immediately after delivery up to the time of collection of stem cells, e.g., by perfusion, enzymatic digestion, or culture of placental tissue. In a specific embodiment, stem cells are collected from the refrigerated placenta at from about 20 to about 24 hours after delivery.

Without wishing to be bound by any theory, after exsanguination and a sufficient time of perfusion of the placenta, placental stem cells are believed to migrate into the exsanguinated and perfused microcirculation of the placenta where, according to the methods of the invention, they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion according to the methods of the invention results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion according to the methods of the invention yields significantly more placental stem cells than, e.g., the number of placental stem cells obtainable from culture medium in which a placenta, or portion thereof, has been cultured.

Stem cells may be isolated from, e.g., placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition of the invention.

5.2.3 Isolation, Sorting and Characterization of Stem Cells

Cells from an organ, e.g., mammalian placenta, whether obtained by perfusion or enyzmatic digestion, can initially be purified from other cells (i.e., isolated) by Ficoll gradient centrifugation. Such centrifugation can follow any standard protocol for centrifugation speed, etc. In one embodiment, cells collected from the organ, e.g., placenta, are recovered from perfusate by centrifugation at about 400 to about 1000× g for about 10-30 minutes at room temperature. In another embodiment, perfusate is concentrated to about 200 ml, gently layered over, e.g., a Ficoll, Percoll or hetastarch gradient, and centrifuged at about, e.g., 400-3000× g for 20 minutes at 22° C., and the low-density interface layer of cells is collected for further processing. In another embodiment, hetastarch is mixed with placental cells, and is allowed to settle by gravity; the supernatant is removed and the hetastarch and cells are collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY), DMEM, or the like. In one embodiment, placental cells obtained by perfusion or disruption e.g., enzymatic digestion, can be selected in medium composed of, e.g., DMEM-LG, MCDB-201, (ITS (insulin, transferrin, selenium), LA-BSA (linoleic acid-bovine serum albumin), dexamethasone, EGF (epidermal growth factor, PDGF (platelet-derived growth factor), and antibiotics, e.g., penicillin and/or streptomycin. The total mononuclear cell fraction can be isolated, e.g., using Lymphoprep (Nycomed Pharma, Oslo, Norway) according to the manufacturer's recommended procedure and the mononuclear cell fraction was resuspended. The stem cell composition, or medium, in which the stem cells are resuspended preferably comprises a stem cell-compatible protein, e.g., albumin, for example, human albumin.

As used herein, "isolating stem cells" means removing at least 50% of the cells with which the stem cells are normally associated with in the intact organ, e.g., placenta. A stem cell from an organ is "isolated" when it is present, with other stem cells from the organ, in a population of cells that comprises fewer than 50% of the cells with which the stem cell is normally associated in the intact organ.

Placental cells obtained by perfusion or digestion can be further, or initially, isolated by differential trypsinization using, e.g., a solution of 0.05% trypsin with 0.2% EDTA (Sigma, St. Louis Mo.). Differential trypsinization is possible because fibroblastoid cells collected from, e.g., placenta, typically detach from plastic surfaces within about five minutes whereas other adherent populations typically require more than 20-30 minutes incubation. The detached fibroblastoid cells can be harvested following trypsinization and trypsin neutralization, using, e.g., Trypsin Neutralizing Solution (TNS, Cambrex). In one embodiment of isolation of adherent cells, aliquots of, for example, about $5-10 \times 10^6$ cells are placed in each of several T-75 flasks, preferably fibronectin-coated T75 flasks. The cells are cultured with commercially available Mesenchymal Stem Cell Growth Medium (MSCGM) Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from an organ, e.g., placenta, can easily be monitored by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, or by measuring changes in gene expression using techniques well known in the art, such as PCR and gene expression profiling. Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers AC133, CD34, CD38, CD90, CD117, HLA-DR, CD10, CD4, CD71, CD38, CD45 and CD61 as shown in FIG. 4. In another embodiment, cells from placenta are based on their expression of markers CD200 and/or HLA-G; in one embodiment, cells displaying either of these markers are isolated for further use. Cells that express, e.g., CD200 and/or HLA-G can, in a specific embodiment, be further sorted based on their expression of CD73 or CD105, or epitopes recognized by antibodies SH2, SH3 or SH4, or lack of expression of CD34, CD38 or CD45. For example, in one embodiment, placental cells are sorted by their expression, or lack thereof, of CD200, HLA-G, CD73, CD105, CD34, CD38 and CD45, and placental cells that are $CD200^+$, $HLA-G^+$, $CD73^+$, $CD105^+$, $CD34^-$, $CD38^-$ and $CD45^-$ are isolated from other placental cells for further use.

In another embodiment, magnetic beads can be used to separate cells. The cells may be sorted using a magnetic activated cell sorting (MACS) technique, a method for separating particles based on their ability to bind magnetic beads (0.5-100 µm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental cells, e.g., placental stem cells, can also be characterized and/or sorted based on cell morphology and growth characteristics. For example, placental cells can be characterized as having, and/or selected on the basis of, e.g., a cobblestone or fibroblastoid appearance in culture. Placental cells can also be characterized as having, and/or selected on the basis of, e.g., their ability or inability to form embryoid bodies. In one embodiment, for example, placental cells that are fibroblastoid in shape, express CD73 and CD105, and produce one or more embryoid bodies in culture are isolated from other placental cells. In another embodiment, $OCT-4^+$ placental cells that produce one or more embryoid bodies in culture are isolated from other placental cells.

In another embodiment, placental stem cells can be identified and characterized by a colony forming unit assay. Colony forming units assays are commonly known in the art, such as Mesen Cult™ medium (Stem Cell Technologies, Inc., Vancouver British Columbia)

Stem cells, e.g., placental stem cells, may be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

5.2.4 Stem Cell Storage

In other embodiments, the cells collected from the placenta are cryopreserved for use at a later time. Methods for cryopreservation of cells, such as stem cells, are well known in the art, for example, Hu et al. (WO 00/73421, published Dec. 7, 2000).

5.2.5 Assessing Potency of Stem Cell Populations

A placenta-derived stem cell population, or population of isolated cells comprising placenta-derived stem cells, as described herein can be assessed for potency, that is, the number of viable cells, using a colony-forming unit assay. In a preferred embodiment, the colony-forming unit assay is used to assess the potency of a placental stem cell population contained within an initial perfusate of a placenta, or an initial enzyme digestion of placental tissue. A colony-forming unit assay can also be performed on placenta-derived stem cell populations, or populations of isolated placental cells comprising placenta-derived stem cells, that have been passaged at least once, at least five, ten, 15, 20 or more times in culture. Any standard colony-forming unit assay can be used, e.g., colony forming assays provided by StemCell Technologies, Inc. Such an assay may use, e.g., MESEN-CULT™ medium (Stem Cell Technologies, Inc., Vancouver British Columbia).

The colony-forming unit assay can be performed on individual populations (e.g., individual units of perfusate or digestate) of placenta-derived stem cells, or populations of isolated placental cells comprising placenta-derived stem cells, to assess the potency of the populations. For example, the colony-forming unit assay can be used, alone or with other tests, such as viability tests, to determine the number of useful cells in a population of placenta-derived cells. Typically, the colony-forming unit assay would be performed on a small sample cells from of a population, and the results extrapolated to the remaining population.

The colony-forming unit assay described above can be used to assess the efficacy of various formulations of the stem cell collection compositions, that is, can be used to identify stem cell collection formulations that improve, or are optimal, for stem cell collection under varying circumstances. Such circumstances can include, for example, methods of obtaining, transporting, culturing or handling a placenta prior to stem cell collection; methods of collection of stem cells, time from placental collection to stem cell collection, presence or absence of a placental culturing step as part of, or prior to, stem cell collection, and the like. In one embodiment, for example, the invention provide a method of assessing the potency of a placenta-derived stem cell population, or population of isolated placental cells comprising placenta-derived stem cells comprising contacting said population with a stem cell collection composition; determining a number of colony-forming units produced by said population in a colony-forming unit assay; wherein said number of colony-forming units is, or is correlated with, the potency of the population. In a specific embodiment, the number of colony-forming units can be compared to a control. For example, the control can be an absolute number of colony-forming units expected for a particular number of placenta-derived stem cells, e.g., a criterion for potency. In another example, the control can be the number of colony-forming units produced by an equivalent number of placenta-derived stem cells contacted with a second stem cell collection formulation; in this example, the method allows for the comparison of two different formulations to assess which is better at preserving, or producing higher numbers of viable, placenta-derived stem cells. In another specific embodiment, the control is the number, or average number, of colony-forming units obtainable under a particular method of transporting a placenta from site of delivery to site of stem cell collection. In another specific embodiment, said control is the number of colony-forming units obtainable under a particular method of handling the placenta at the site of stem cell collection.

In another embodiment, the invention provides a method of selecting a stem cell collection composition to preserve a population of placenta-derived stem cells, or population of isolated placental cells that comprises placenta-derived stem cells, comprising contacting a first population comprising a number of placenta-derived stem cells with a first stem cell collection composition, wherein said first population produces a first number of colony-forming units in a colony-forming unit assay, and a second population comprising said number of placenta-derived stem cells with a second stem cell collection composition, wherein said second population produces a second number of colony-forming units in a colony-forming unit assay, and comparing a first number of colony-forming units to said second number of colony-forming units, and selecting whichever of said first number or said second number is higher.

5.3 Stem Cell Preservation

In another aspect, the invention provides compositions and methods for preserving a population of stem cells. The invention encompasses the preservation of a population of stem cells whether a the population is a population of isolated stem cells or a population of stem cells in situ, in an organ or tissue, prior to, or during, the process of isolation and collection. For example, the methods and compositions of the invention can be used to preserve a population of isolated placental stem cells, or a population of placental stem cells in the placenta, e.g., while the placenta is in transport or is awaiting processing to isolate and collect placental stem cells.

The invention further provides methods of preserving a population of stem cells using a stem cell collection composition comprising an inhibitor of apoptosis and an oxygen-carrying perfluorocarbon, e.g., a perfluorocarbon as described in Section 5.1.5, above. In one embodiment, the invention provides a method of preserving a population of stem cells comprising contacting said population of stem cells with an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor, e.g., a JNK inhibitor described in Section 5.1.2.2, above. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In another embodiment, the invention provides a method of preserving a population of stem cells comprising contacting said population of stem cells, or an organ (e.g., placenta) comprising the stem cells, with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, the organ-preserving compound is UW solution (descried in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, said stem cells are contacted with said stem cell collection composition comprising an apoptosis inhibitor and oxygen-carrying perfluorocarbon, organ-preserving compound, or combination thereof, during perfusion. In another embodiment, said stem cells are contacted during a process of tissue dissociation. In another embodiment, said stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than 72 hours during said preservation, wherein a hypoxic condition is a concentration of oxygen that is less than normal blood oxygen concentration. In a more specific embodiment, said population of stem cells is exposed to said hypoxic condition for less than 48 hours during said preservation. In another more specific embodiment, said population of stem cells is exposed to said hypoxic condition for less than 24 hours, or less than 12, 6, or 2 hours, or is not exposed to a hypoxic condition, during collection, enrichment or isolation. In another specific embodiment, said population of stem cells is not exposed to shear stress during collection, enrichment or isolation.

5.4 Placental Handling

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be obtained commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

Typically, a placenta is transported from the delivery or birthing room to another location, e.g., a laboratory, for recovery of cord blood and collection of stem cells by, e.g., perfusion or tissue dissociation. In one embodiment, the placenta is preferably transported in a sterile, thermally insulated transport device (maintaining the temperature of the placenta between 20-28° C.), for example, by placing the placenta, with clamped proximal umbilical cord, in a sterile plastic bag, which is then placed in an insulated container. In another embodiment, the placenta is transported in a cord blood collection kit substantially as described in pending U.S. patent application Ser. No. 11/230,760, filed Sep. 19, 2005, which is incorporated herein by reference in its entirety. Preferably, the placenta is delivered to the laboratory four to twenty-four hours following delivery.

The placenta, prior to stem cell collection, can be stored under sterile conditions and at either room temperature or at a temperature of 5° C. to 25° C. (centigrade). The placenta may be stored for a period of longer than forty eight hours, and or for a period of, e.g., four to twenty-four hours prior to perfusing the placenta to remove any residual cord blood. The placenta is preferably stored in an anticoagulant solution at a temperature of 5° C. to 25° C. (centigrade). Suitable anticoagulant solutions are well known in the art. For example, a solution of heparin or warfarin sodium can be used. In a preferred embodiment, the anticoagulant solution comprises a solution of heparin (1% w/w in 1:1000 solution). The exsanguinated placenta is preferably stored for no more than 36 hours before placental stem cells are collected.

While the placenta is awaiting stem cell collection, the placenta can be contacted with a solution comprising one or more oxygen-carrying perfluorocarbons (e.g., delivery room) to the site of stem cell collection for at least part of the time between placental collection and stem cell collection. Preferably, the placenta is kept in contact with the oxygen-carrying perfluorocarbon for a majority of the time between placental collection and stem cell collection. The placenta can be contacted with a composition comprising one or more oxygen-carrying perfluorocarbons and one or more organ preservation media (e.g., UW solution; see Section 5.3, above) for at least part of the time between placental collection and stem cell collection.

5.5 Placental Stem Cells

Placental stem cells that can be obtained in accordance with the methods of the invention include pluripotent and multipotent cells, stem cells having one or more characteristics of embryonic stem cells, and committed progenitor cells.

Cord blood and placental blood contain predominantly $CD34^+CD38^+$ hematopoietic progenitor cells. Within the first twenty-four hours after exsanguination and removal of substantially all placental and umbilical cord blood, high numbers of $CD34^+CD38^-$ hematopoietic progenitor cells, relative to the number that may be found in cord blood or bone marrow, can be isolated from the placenta, along with high numbers of $CD34^-CD38^+$ hematopoietic progenitor cells. After about twenty-four hours of culture or maintenance in perfusion solution, high numbers of $CD34^-CD38^-$ cells, relative to the amount that can be obtained from, e.g., cord blood or bone marrow, can be isolated from the placenta along with the aforementioned cells.

In a preferred embodiment, placental stem cells obtained by the methods of the invention are viable, quiescent, multipotent or pluripotent stem cells At least one class of human placental stem cells is developmentally naive. For example, such stem cells are $SSEA3^-$ (stage-specific embryonic antigen 3), $SSEA4^-$, $OCT-4^+$ (a stem cell transcription factor) and $ABC-p^+$ (ATP-binding cassette (ABC) transporter protein), markers that are indicative of developmental naiveté. In a specific embodiment, the stem cells are non-embryonic and $SSEA3^- SSEA4^-OCT-4^+ABC-p^+$. In another embodiment, the human placental stem cells do not express MHC Class 2 antigens. In another embodiment, such stem cells are able to differentiate into endodermal, ectodermal, or mesodermal cells.

In one embodiment, placental stem cells obtained by the methods of the invention can be identified by the presence of the markers OCT-4 and ABC-p. Further, the invention encompasses the collection of placental stem cells displaying the markers CD10, CD29, CD44, CD54, CD90, CD105 (SH2), CD73 (SH3, SH4), OCT-4, and ABC-p, or lacking or not displaying the markers CD34, CD38, CD45, SSEA3, or SSEA4. In a specific embodiment, the placental stem cells are CD10$^+$, CD29$^+$, CD34$^-$, CD38$^-$, CD44$^+$, CD45-, CD54$^+$, CD73$^+$, CD90$^+$, CD105$^+$, SSEA3$^-$, SSEA4$^-$. OCT-4$^+$, and ABC-p$^+$. In another specific embodiment, the placental stem cells are CD200$^+$ and HLA-G$^+$. In another specific embodiment, the placental stem cells are CD73$^+$, CD105$^+$ and CD200$^+$. In another specific embodiment, the placental stem cells are CD200$^+$ and OCT-4$^+$. In another specific embodiment, the placental stem cells are CD73$^+$ and CD105$^+$, and a population of isolated placental cells comprising the placental stem cells forms embryoid bodies under conditions that allow the formation of embryoid bodies. In another specific embodiment, the placental stem cells are CD73$^+$, CD105$^+$ and HLA-G$^+$. In another specific embodiment, the placental stem cells are OCT-4$^+$ and form embryoid bodies under conditions that allow the formation of embryoid bodies.

Such cell surface markers are routinely detected according to methods well known in the art, e.g. by flow cytometry, followed by washing and staining with an anti-cell surface marker antibody. For example, to determine the presence of CD34 or CD38, cells may be washed in PBS and then double-stained with anti-CD34 phycoerythrin and anti-CD38 fluorescein isothiocyanate (Becton Dickinson, Mountain View, Calif.).

The placental stem cells that can be collected by the methods and compositions of the invention can be used for a wide variety of therapeutic protocols in which a tissue or organ of the body is augmented, repaired or replaced by the engraftment, transplantation or infusion of a desired cell population, such as a stem cell or progenitor cell population. The placental stem cells of the invention can be used to replace or augment existing tissues, to introduce new or altered tissues, or to join together biological tissues or structures. The placental stem cells of the invention can also be substituted for embryonic stem cells in therapeutic protocols in which embryonic stem cells would be typically be used.

6. EXAMPLES 6.1 Example 1: Stem Cell Collection Compositions

The following Example describes formulations of a stem cell collection composition. Other embodiments will be apparent to one of skill in the art.

6.1.1 Compositions Comprising an Apoptosis Inhibitor and a Protease

A perfusion solution is made comprising 0.9% NaCl, caspase inhibitor Ac-Val-Ala-Asp-CHO at a final concentration of 50-100 μM, and trypsin-EDTA at a final concentration of about 0.25%.

A perfusion solution is made comprising the modified Krebs solution shown in Example 1, caspase inhibitor Ac-Val-Ala-Asp-CHO at a final concentration of 50-100 μM, and trypsin-EDTA at a final concentration of about 0.25%.

A perfusion solution is made comprising the DMEM-based solution shown in Example 1, caspase inhibitor Ac-Val-Ala-Asp-CHO at a final concentration of 50-100 μM, and trypsin-EDTA at a final concentration of about 0.25%.

6.1.2 Compositions Comprising a Combination of Apoptosis Inhibitors and a Protease A perfusion solution is made comprising 0.9% NaCl, caspase inhibitor Ac-Val-Ala-Asp-CHO at a final concentration of 50-100 trypsin-EDTA at a final concentration of about 0.25%, and a JNK inhibitor having one of the following structures:

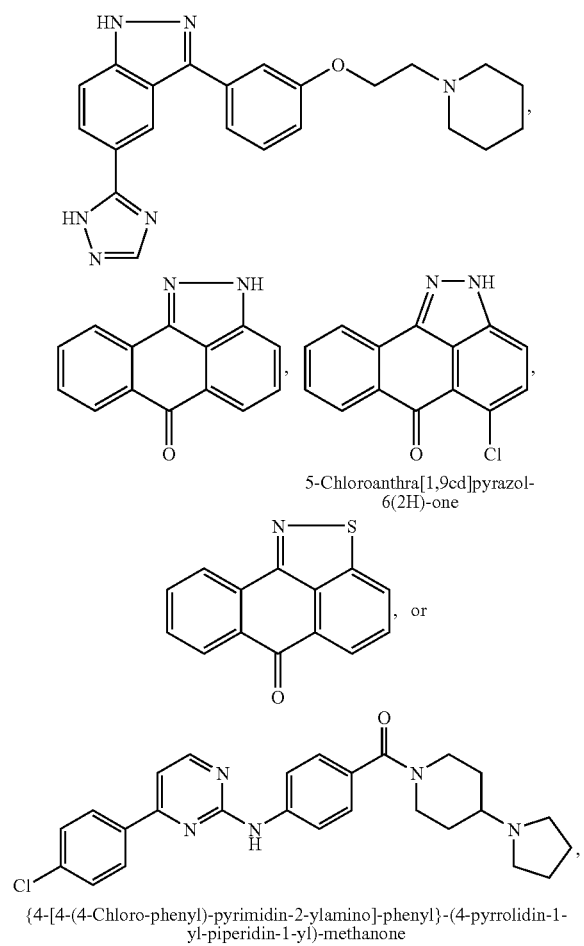

5-Chloroanthra[1,9cd]pyrazol-6(2H)-one

{4-[4-(4-Chloro-phenyl)-pyrimidin-2-ylamino]-phenyl}-(4-pyrrolidin-1-yl-piperidin-1-yl)-methanone wherein the JNK inhibitor is present at a concentration of about 0.5 μM to about 10 μM.

A perfusion solution is made comprising the DMEM-based solution shown in Example 1, caspase inhibitor Ac-Val-Ala-Asp-CHO at a final concentration of 50-100 μM, a JNK inhibitor as shown above in this Example, and trypsin-EDTA at a final concentration of about 0.25%.

A perfusion solution is made comprising the modified Krebs solution shown in Example 1, caspase inhibitor Ac-Val-Ala-Asp-CHO at a final concentration of 50-100 μM, a JNK inhibitor as shown above in this Example, and trypsin-EDTA at a final concentration of about 0.25%.

6.1.3 Compositions Comprising a JNK Inhibitor and a Combination of Proteases

A perfusion solution is made comprising 0.9% NaCl; a cocktail of proteases comprising elastase at a final concentration of about 1.0 mg/mL, collagenase I at a final concentration of about 1.0 mg/mL, collagenase IV at a final concentration of about 0.5 mg/mL, and dispase at a final concentration of about 0.1 mg/ml; and a JNK inhibitor having one of the following structures:

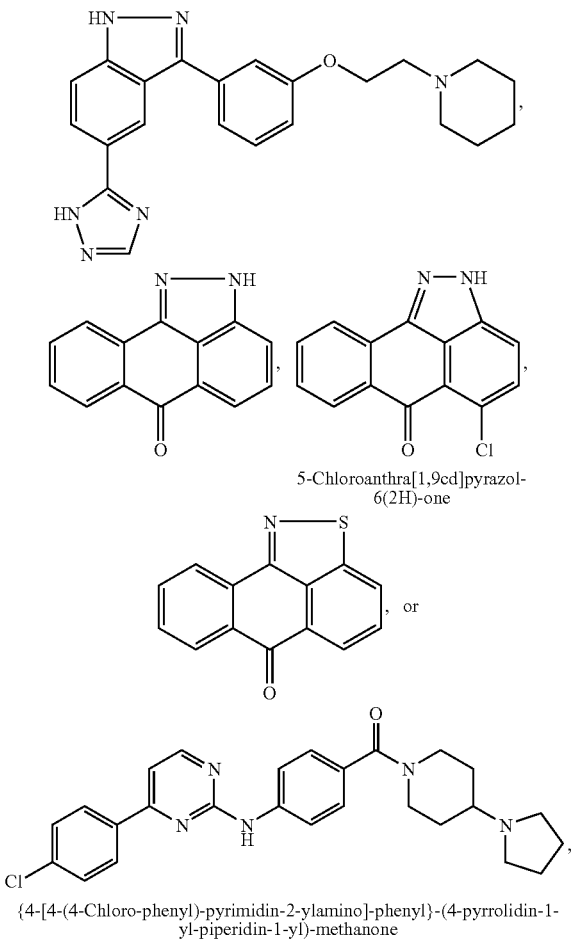

5-Chloroanthra[1,9cd]pyrazol-6(2H)-one

5-Chloroanthra[1,9cd]pyrazol-6(2H)-one

{4-[4-(4-Chloro-phenyl)-pyrimidin-2-ylamino]-phenyl}-(4-pyrrolidin-1-yl-piperidin-1-yl)-methanone {4-[4-(4-Chloro-phenyl)-pyrimidin-2-ylamino]-phenyl}-(4-pyrrolidin-1-yl-piperidin-1-yl)-methanone wherein the JNK inhibitor is present at a concentration of about 0.5 µM to about 10 µM.

A perfusion solution is made comprising the DMEM-based solution shown in Example 1; a cocktail of proteases comprising elastase at a final concentration of about 1.0 mg/mL, collagenase I at a final concentration of about 1.0 mg/mL, collagenase IV at a final concentration of about 0.5 mg/mL, and dispase at a final concentration of about 0.1 mg/mL; and a JNK inhibitor as shown above in this Example.

A perfusion solution is made comprising the modified Krebs solution shown in Example 1; a cocktail of proteases comprising elastase at a final concentration of about 1.0 mg/mL, collagenase I at a final concentration of about 1.0 mg/mL, collagenase IV at a final concentration of about 0.5 mg/mL, and dispase at a final concentration of about 0.1 mg/mL; and a JNK inhibitor as shown above in this Example.

6.1.4 Compositions Comprising a Combination of JNK Inhibitors and a Combination of Enzymes A perfusion solution is made comprising 0.9% NaCl; a cocktail of proteases comprising elastase at a final concentration of about 1.0 mg/mL, collagenase I at a final concentration of about 1.0 mg/mL, collagenase IV at a final concentration of about 0.5 mg/mL, dispase at a final concentration of about 0.1 mg/mL, and hyaluronidase at a concentration of about 0.1 to about 10.0 mg/mL; and two or more JNK inhibitors having one or more of the of the following structures:

wherein the JNK inhibitor is present at a concentration of about 0.5 µM to about 10 µM.

A perfusion solution is made comprising the DMEM-based solution shown in Example 1; a cocktail of proteases comprising elastase at a final concentration of about 1.0 mg/mL, collagenase I at a final concentration of about 1.0 mg/mL, collagenase IV at a final concentration of about 0.5 mg/mL, dispase at a final concentration of about 0.1 mg/mL, and hyaluronidase at a concentration of about 0.1 to about 10.0 mg/mL; and two or more of the JNK inhibitors as shown above in this Example.

A perfusion solution is made comprising the modified Krebs solution shown in Example 1; a cocktail of proteases comprising elastase at a final concentration of about 1.0 mg/mL, collagenase I at a final concentration of about 1.0 mg/mL, collagenase IV at a final concentration of about 0.5 mg/mL, dispase at a final concentration of about 0.1 mg/mL, and hyaluronidase at a concentration of about 0.1 to about 10.0 mg/mL; and two or more of the JNK inhibitors as shown above in this Example.

6.1.5 Compositions Comprising JNK Inhibitor, Protease and Vasodilator

A perfusion solution is made comprising 0.9% NaCl; trypsin-EDTA at a final concentration of about 0.25%; magnesium sulfate as a vasodilator at a concentration of about 0.15 mM to about 6 mM; and a JNK inhibitor having one of the following structures:

5-Chloroanthra[1,9cd]pyrazol-6(2H)-one

{4-[4-(4-Chloro-phenyl)-pyrimidin-2-ylamino]-phenyl}-(4-pyrrolidin-1-yl-piperidin-1-yl)-methanone wherein the JNK inhibitor is present at a concentration of about 0.5 µM to 10 µM.

A perfusion solution is made comprising the DMEM-based solution shown in Example 1; trypsin-EDTA at a final concentration of about 0.25%; magnesium sulfate as a vasodilator at a concentration of about 0.15 mM to about 6 mM; and a JNK inhibitor as shown above in this Example.

A perfusion solution is made comprising the modified Krebs solution shown in Example 1; trypsin-EDTA at a final concentration of about 0.25%; magnesium sulfate as a vasodilator at a concentration of about 0.15 mM to about 6 mM; and a JNK inhibitor as shown above in this Example.

6.1.6 Compositions Comprising JNK Inhibitor, Protease and Anti-Necrosis Agent

A perfusion solution is made comprising 0.9% NaCl; trypsin-EDTA at a final concentration of about 0.25%; 2-(1H-Indol-3-yl)-3-pentylamino-maleimide at a concentration of about 0.5 µM to about 100.0 µM; and a INK inhibitor having one of the following structures:

5-Chloroanthra[1,9cd]pyrazol-6(2H)-one

{4-[4-(4-Chloro-phenyl)-pyrimidin-2-ylamino]-phenyl}-(4-pyrrolidin-1-yl-piperidin-1-yl)-methanone wherein the JNK inhibitor is present at a concentration of about 0.5 µM to about 10.0 µM.

A perfusion solution is made comprising the DMEM-based solution shown in Example 1; trypsin-EDTA at a final concentration of 0.25%; 2-(1H-Indol-3-yl)-3-pentylamino-maleimide at a concentration of 0.5 µM to about 100.0 µM; and a JNK inhibitor as shown above in this Example.

A perfusion solution is made comprising the modified Krebs solution shown in Example 1; trypsin-EDTA at a final concentration of 0.25%; 2-(1H-Indol-3-yl)-3-pentylamino-maleimide at a concentration of 0.5 µM to about 100.0 µM; and a JNK inhibitor as shown above in this Example.

6.1.7 Compositions Comprising JNK Inhibitor, Protease and Oxygen-Carrying Perfluorocarbon A perfusion solution is made comprising 0.9% NaCl; trypsin-EDTA at a final concentration of 0.25%; and a JNK inhibitor having one of the following structures:

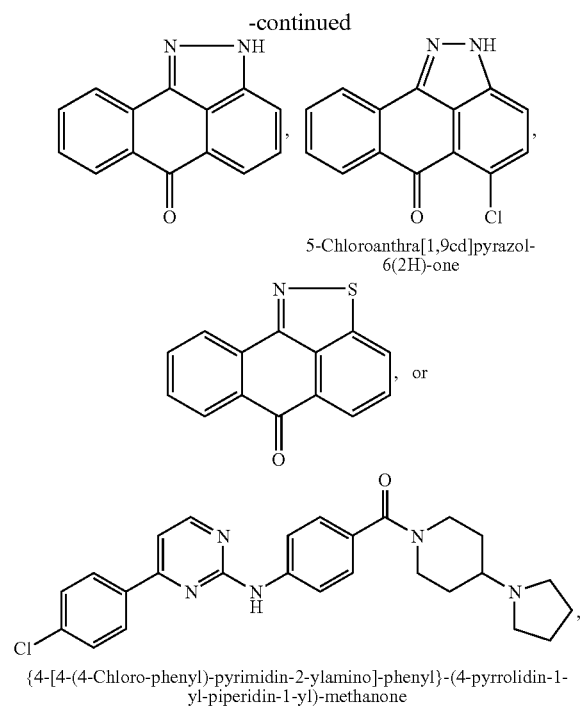

{4-[4-(4-Chloro-phenyl)-pyrimidin-2-ylamino]-phenyl}-(4-pyrrolidin-1-yl-piperidin-1-yl)-methanone wherein the JNK inhibitor is present at a concentration of about 0.5 µM to about 10.0 µM. The solution also comprises perfluorooctylbromide at 50%-100% weight to volume, perfluorodecylbromide at about 10% of the volume of perfluorooctylbromide and lecithin as an emulsifier at about 4% weight to volume. The solution is emulsified prior to use.

A perfusion solution is made as above, but comprising the DMEM-based solution shown in Example 1 in place of 0.9% NaCl. A perfusion solution is made as above, but comprising the modified Krebs solution shown in Example 1 in place of 0.9% NaCl.

6.2 Example 2: Placental Stem Cell Culture

Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

Placental Stem Cells Isolated by Perfusion

Cultures of placental stem cells from placental perfusate are established as follows. Cells from a Ficoll gradient are seeded in FN-coated T75 flasks, prepared as above, at 50-100×$10^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

Placental Stem Cells Isolated by Enzymatic Digestion

Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately 1×2×1 cm. This placenta tissue is then minced into approximately 1 mm³ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in about 130 ml culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells are quickly thawed in a 37° C. water bath. Placental stem cells are immediately removed from the cryovial with 10 ml warm medium and transferred to a 15 ml sterile tube. The cells are centrifuged at about 400× g for 5 minutes at room temperature. The cells are gently resuspended in 10 ml of warm culture medium by pipetting, and viable cell counts are determined by Trypan blue exclusion. Cells are then seeded at about 6000-7000 cells per cm² onto FN-coated flasks, prepared as above (approximately 5×$10^5$ cells per T-75 flask). The cells are incubated at 37° C., 5% $CO_2$ and 90% humidity. When the cells reached 75-85% confluency, all of the spent media is aseptically removed from the flasks and discarded. 3 ml of trypsin/EDTA solution, 0.25%, is added to cover the cell layer, and the cells are incubated at 37° C., 5% $CO^2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

Using the above methods, populations of adherent placental stem cells are identified that express markers CD105, CD117, CD33, CD73, CD29, CD44, CD10, CD90 and CD133. This population of cells did not express CD34 or CD45. Some, but not all cultures of these placental stem cells expressed HLA-ABC and/or HLA-DR.

6.3 Example 3: Differentiation of Placental Stem Cells 6.3.1 Induction of Differentiation into Neurons Neuronal differentiation of placental stem cells can be accomplished, for example, as follows:
1. Placental stem cells are grown for 24 hr in preinduction medium consisting of DMEM/20% FBS and 1 mM beta-mercaptoethanol.
2. The preinduction medium is removed and cells are washed with PBS.
3. Neuronal induction medium consisting of DMEM and 1-10 mM betamercaptoethanol is added to the cells. Alternatively, induction media consisting of DMEM/2% DMSO/200 µM butylated hydroxyanisole may be used.
4. In certain embodiments, morphologic and molecular changes may occur as early as 60 minutes after exposure to serum-free media and betamercaptoethanol. RT/PCR may be used to assess the expression of e.g., nerve growth factor receptor and neurofilament heavy chain genes.

6.3.2 Induction of Differentiation into Adipocytes

Adipogenic differentiation of placental stem cells can be accomplished, for example, as follows:
1. Placental stem cells are grown in MSCGM (Cambrex) or DMEM supplemented with 15% cord blood serum.
2. Three cycles of induction/maintenance are used. Each cycle consists of feeding the placental stem cells with Adipogenesis Induction Medium (Cambrex) and culturing the cells for 3 days (at 37° C., 5% $CO_2$), followed by 1-3 days of culture in Adipogenesis Maintenance Medium (Cambrex). An alternate induction medium that can be used contains 1 µM dexamethasone, 0.2 mM indomethacin, 0.01 mg/ml insulin, 0.5 mM IBMX, DMEM-high glucose, FBS, and antibiotics.
3. After 3 complete cycles of induction/maintenance, the cells are cultured for an additional 7 days in adipogenesis maintenance medium, replacing the medium every 2-3 days.
4. A hallmark of adipogenesis is the development of multiple intracytoplasmic lipid vesicles that can be easily observed using the lipophilic stain oil red O. Expression of lipase and/or fatty acid binding protein genes is confirmed by RT/PCR in placental stem cells that have begun to differentiate into adipocytes.

6.3.3 Induction of Differentiation into Chondrocytes

Chondrogenic differentiation of placental stem cells can be accomplished, for example, as follows:
1. Placental stem cells are maintained in MSCGM (Cambrex) or DMEM supplemented with 15% cord blood serum.
2. Placental stem cells are aliquoted into a sterile polypropylene tube. The cells are centrifuged (150× g for 5 minutes), and washed twice in Incomplete Chondrogenesis Medium (Cambrex).
3. After the last wash, the cells are resuspended in Complete Chondrogenesis Medium (Cambrex) containing 0.01 µg/ml TGF-beta-3 at a concentration of 5×10(5) cells/ml.
4. 0.5 ml of cells is aliquoted into a 15 ml polypropylene culture tube. The cells are pelleted at 150× g for 5 minutes. The pellet is left intact in the medium.
5. Loosely capped tubes are incubated at 37° C., 5% $CO^2$ for 24 hours.
6. The cell pellets are fed every 2-3 days with freshly prepared complete chondrogenesis medium.
7. Pellets are maintained suspended in medium by daily agitation using a low speed vortex.
8. Chondrogenic cell pellets are harvested after 14-28 days in culture.
9. Chondrogenesis is characterized by e.g., observation of production of esoinophilic ground substance, assessing cell morphology, an/or RT/PCR confirmation of collagen 2 and collagen 9 gene expression.

6.3.4 Induction of Differentiation into Osteocytes

Osteogenic differentiation can be accomplished, for example, as follows:
1. Adherent cultures of placental stem cells are cultured in MSCGM (Cambrex) or DMEM supplemented with 15% cord blood serum.
2. Cultures are cultured for 24 hours in tissue culture flasks.
3. Osteogenic differentiation is induced by replacing MSCGM with Osteogenic Induction Medium (Cambrex) containing 0.1 µM dexamethasone, 0.05 mM ascorbic acid-2-phosphate, 10 mM beta glycerophosphate.
4. Cells are fed every 3-4 days for 2-3 weeks with Osteogenic Induction Medium.
5. Differentiation is assayed using a calcium-specific stain and RT/PCR for alkaline phosphatase and osteopontin gene expression.

6.3.5 Induction of Differentiation into Pancreatic Cells

Pancreatic differentiation can be accomplished, for example, as follows:
1. Placental stem cells are cultured in DMEM/20% CBS, supplemented with basic fibroblast growth factor (10 ng/ml), nicotinamide (10 mM), B27 (1×), N2 (1×), and transforming growth factor beta-1, 2 ng/ml. KnockOut Serum Replacement may be used in lieu of CBS.
2. Conditioned media from nestin-positive neuronal cell cultures is added to media at a 50/50 concentration.
3. Cells are cultured for 14-28 days, refeeding every 3-4 days.
4. Differentiation is characterized by assaying for insulin protein or insulin gene expression by RT/PCR.

6.3.6 Induction of Differentiation into Cardiac Cells

Myogenic (cardiogenic) differentiation can be accomplished, for example, as follows:
1. Placental stem cells are cultured in DMEM/20% CBS, supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement (Invitrogen, Carlsbad, Calif.) may be used in lieu of CBS.
2. Alternatively, placental stem cells are cultured in DMEM/20% CBS supplemented with 50 ng/ml Cardiotropin-1 for 24 hours.
3. Alternatively, placental stem cells are maintained in protein-free media for 5-7 days, then stimulated with human myocardium extract (escalating dose analysis). Myocardium extract is produced by homogenizing 1 gm human myocardium in 1% HEPES buffer supplemented with 1% cord blood serum. The suspension is incubated for 60 minutes, then centrifuged and the supernatant collected.
4. Cells are cultured for 10-14 days, refeeding every 3-4 days.
5. Differentiation is confirmed by demonstration of cardiac actin gene expression by RT/PCR.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method of isolating stem cells, the method comprising contacting said stem cells with a solution comprising a caspase inhibitor, a JNK inhibitor, a protease, and either pyrrolidine dithiocarbamate or clonazepam,
   wherein the JNK inhibitor is an inhibitor of apoptosis, said JNK inhibitor represented by the structure wherein:
A is a direct bond, —$(CH_2)_a$—, —$(CH_2)_b$CH═CH$(CH_2)_c$—, or —$(CH_2)_b$C≡C$(CH_2)_c$—;
$R_1$ is aryl, heteroaryl or heterocycle fused to phenyl, each being optionally substituted with one to four substituents independently selected from $R_3$;
$R_2$ is —$R_3$, —$R_4$, —$(CH_2)_bC(═O)R_5$, —$(CH_2)_bC(═O)OR_5$, —$(CH_2)_bC(═O)NR_5R_6$, —$(CH_2)_bC(═O)NR_5(CH_2)_cC(═O)R_6$, —$(CH_2)_bNR_5C(═O)R_6$, —$(CH_2)_bNR_5C(═O)NR_6R_7$, —$(CH_2)_bNR_5R_6$, —$(CH_2)_bOR_5$, —$(CH_2)_bSO_dR_5$ or —$(CH_2)_bSO_2NR_5R_6$;
a is 1, 2, 3, 4, 5 or 6;
b and c are the same or different and at each occurrence independently selected from 0, 1, 2, 3 or 4;
d is at each occurrence 0, 1 or 2;
$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —$C(═O)OR_8$, —$OC(═O)R_8$, —$C(═O)NR_8R_9$, —$C(═O)NR_8OR_9$, —$SO_2NR_8R_9$, —$NR_8SO_2R_9$, —CN, —$NO_2$, —$NR_8R_9$, —$NR_8C(═O)R_9$, —$NR_8C(═O)(CH_2)_bOR_9$, —$NR_8C(═O)(CH_2)_bR_9$, —$O(CH_2)_bNR_8R_9$, or heterocycle fused to phenyl;
$R_4$ is alkyl, aryl, arylalkyl, heterocycle or heterocycloalkyl, each being optionally substituted with one to four substituents independently selected from $R_3$, or $R_4$ is halogen or hydroxy;
$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and
$R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$;
or a pharmaceutically acceptable salt, hydrate, solvate, clathrate, enantiomer, diastereomer, racemate, or mixture of stereoisomers thereof;
and wherein said method of isolating further comprises isolating the stem cells subsequent to said contacting step; wherein said stem cells are isolated from a mammalian placenta, and said contacting is performed during perfusion of said mammalian placenta with a perfusion solution comprising said caspase inhibitor, said JNK inhibitor, said protease, and said pyrrolidine dithiocarbamate or clonazepam.

2. The method of claim 1, wherein the JNK inhibitor is 3-(4-fluoro-phenyl)-1H-indazole-5-carboxylic acid amide.

3. The method of claim 1, additionally comprising contacting said stem cells with an oxygen-carrying perfluorocarbon.

4. The method of claim 1, wherein said solution is a saline solution.

5. The method of claim 1, wherein said solution additionally comprises hydroxyethyl starch, lactobionic anion and raffinose.

6. The method of claim 1, wherein said solution comprises UW solution.

7. The method of claim 1, wherein said perfusion is performed by passing said perfusion solution into one or both of the umbilical artery and umbilical vein of said placenta.

8. The method of claim 1, wherein said perfusion solution comprises 0.9% NaCl solution or phosphate buffered saline.

9. The method of claim 1, wherein said perfusion uses from about 100 mL to about 10,000 mL of said perfusion solution.

10. The method of claim 1, said method comprising isolating said stem cells, wherein said stem cells are exposed to a hypoxic condition for less than 24 hours during said isolation, wherein a hypoxic condition is a concentration of oxygen that is less than normal blood oxygen concentration.

11. The method of claim 1, additionally comprising contacting the stem cells with an amino-substituted isoindoline.

12. The method of claim 11, wherein said amino-substituted isoindoline is a compound represented by the structure wherein:
one of X and Y is C═O and the other is $CH_2$ or C═O;
R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons;

$R^6$ is hydrogen, alkyl of 1 to 8 carbon atoms, benzo, chloro, or fluoro;

$R'$ is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center;

or a pharmaceutically acceptable salt, hydrate, solvate, clathrate, enantiomer, diastereomer, racemate, or mixture of stereoisomers thereof.

13. The method of claim 11, wherein said substituted isoindoline is 3-(4-amino-1-oxo-1,3-dihydroisoindol-2-yl)-piperidine-2,6-dione, or 4-(Amino)-2-(2,6-dioxo(3-piperidyl))-isoindoline-1,3-dione.

14. The method of claim 1, wherein said solution additionally comprises a vasodilator.

15. The method of claim 14, wherein said vasodilator is atrial natriuretic peptide (ANP), adrenocorticotropin, corticotropin-releasing hormone, sodium nitroprusside, hydralazine, adenosine triphosphate, adenosine, indomethacin or magnesium sulfate.

16. The method of claim 1, wherein said stem cells are CD34+ stem cells.

17. The method of claim 1, wherein said stem cells are tissue culture plastic-adherent CD34$^-$, CD10$^+$, CD105$^+$, CD200$^+$ placental stem cells.

18. The method of claim 1, wherein said solution is culture medium.

* * * * *